(12) United States Patent
Foxwell et al.

(10) Patent No.: US 7,915,009 B2
(45) Date of Patent: Mar. 29, 2011

(54) ACTIVATION AND INHIBITION OF THE IMMUNE SYSTEM

(75) Inventors: Brian Foxwell, London (GB); Marc Feldmann, London (GB)

(73) Assignee: The Mathilda and Terence Kennedy Institute of Rheumatology Trust, London (GB)

( * ) Notice: Subject to any disclaimer, the term of this patent is extended or adjusted under 35 U.S.C. 154(b) by 613 days.

(21) Appl. No.: 10/168,805

(22) PCT Filed: Dec. 22, 2000

(86) PCT No.: PCT/GB00/04925
§ 371 (c)(1),
(2), (4) Date: Jan. 31, 2003

(87) PCT Pub. No.: WO01/47543
PCT Pub. Date: Jul. 5, 2001

(65) Prior Publication Data
US 2003/0153518 A1    Aug. 14, 2003

(30) Foreign Application Priority Data

Dec. 24, 1999 (GB) .................... 9930616.9

(51) Int. Cl.
C12P 21/02 (2006.01)
C12P 21/06 (2006.01)
C12N 15/09 (2006.01)
C12N 1/20 (2006.01)
C12N 15/00 (2006.01)

(52) U.S. Cl. ............... 435/69.1; 435/69.2; 435/252.3; 435/320.1; 435/325

(58) Field of Classification Search ............ 435/6, 91.1, 435/91.2, 69.1, 69.2, 70.4, 252.3, 320.1, 435/325
See application file for complete search history.

(56) References Cited

U.S. PATENT DOCUMENTS

| | | | |
|---|---|---|---|
| 4,987,071 A | 1/1991 | Cech et al. | |
| 5,093,246 A | 3/1992 | Cech et al. | |
| 5,116,742 A | 5/1992 | Cech et al. | |
| 5,149,796 A | 9/1992 | Rossi et al. | |
| 5,168,053 A | 12/1992 | Altman et al. | |
| 5,180,818 A | 1/1993 | Cech et al. | |
| 5,854,043 A | 12/1998 | Johnson | |
| 5,891,924 A | 4/1999 | Aggarwal | |
| 5,951,988 A | 9/1999 | Littel-van den Hurk et al. | |
| 6,294,378 B1 | 9/2001 | Houghton et al. | |
| 6,410,516 B1 | 6/2002 | Baltimore et al. | |
| 6,503,184 B1 * | 1/2003 | Ni et al. ............ | 514/12 |
| 6,528,482 B1 * | 3/2003 | Anderson et al. ......... | 514/2 |
| 2003/0125235 A1 | 7/2003 | Foxwell et al. | |
| 2003/0153518 A1 | 8/2003 | Foxwell et al. | |
| 2004/0086516 A1 | 5/2004 | Foxwell et al. | |
| 2004/0241152 A1 | 12/2004 | Foxwell et al. | |
| 2006/0063697 A1 * | 3/2006 | Gabrilovich et al. ............ | 514/1 |

FOREIGN PATENT DOCUMENTS

| | | |
|---|---|---|
| EP | 0 779 361 A | 6/1997 |
| EP | 0779361 | 6/1997 |
| EP | 0 894 855 A | 2/1999 |
| EP | 0 897 009 A | 2/1999 |
| EP | 0894855 | 2/1999 |
| EP | 0897009 | 2/1999 |
| JP | 06-209778 * | 8/1994 |
| JP | 11-071278 * | 3/1999 |
| JP | 2002-513552 * | 5/2002 |
| WO | WO 91/06571 | 5/1991 |
| WO | WO 92/07573 | 5/1992 |
| WO | WO 94/24281 | 10/1994 |
| WO | WO 95/31483 | 11/1995 |
| WO | WO 96/03144 | 2/1996 |
| WO | 96/25666 | 8/1996 |
| WO | 97/01340 | 1/1997 |
| WO | 97/37016 | 10/1997 |
| WO | 98/06692 | 2/1998 |
| WO | 98/08955 | 3/1998 |
| WO | 98/28424 | 7/1998 |
| WO | 99/57133 * | 1/1999 |
| WO | 99/06009 | 2/1999 |
| WO | WO 99/13064 | 3/1999 |
| WO | 99/27112 | 6/1999 |
| WO | 99/42137 | 8/1999 |
| WO | 99/65449 | 12/1999 |
| WO | WO 00/26249 | 5/2000 |

OTHER PUBLICATIONS

Pettit et al., Nuclear localization of RelB is associated with effective antigen-presenting cell function. J Immunol. Oct. 15, 1997;159(8):3681-91.*
Foxwell et al.,Efficient adenoviral infection with IkappaB alpha reveals that macrophage tumor necrosis factor alpha production in rheumatoid arthritis is NF-kappaB dependent. Proc Natl Acad Sci U S A. Jul. 7, 1998;95(14):8211-5.*
Calder et al., Antigen-specific T-cell downregulation by human dendritic cells following blockade of NF-kappaB.Scand J Immunol. Mar. 2003;57(3):261-70. Abstract PMID 12641655.*
Yoshimura et al., Antigen presentation by murine dendritic cells is nuclear factor-kappa B dependent both in vitro and in vivo.Scand J Immunol. Aug. 2003;58(2):165-72.*
Foxwell et al., High efficient gene transfer is an efficient way of defining therapeutic targets:a functional genomics approach. 2001, Ann Rhem Dis. 60:iii13-iii17.*
Karin et al., hosphorylation meets ubiquitination: the control of NF-[kappa]B activity. Annu Rev Immunol. 2000;18:621-63. Review.*
Goodman and Gilman's The Pharmacological Basis of Therapeutics. Ninth Edition McGraw-Hill 1996 pp. 77-101.*

(Continued)

Primary Examiner — Maria Leavitt
(74) Attorney, Agent, or Firm — Nixon & Vanderhye P.C.

(57) ABSTRACT

Activation of the immune response by NF-kB inducers, induction of an anergic response by NF-kB inhibitors and the inhibition and activation of immune response by the administration of an activator or inhibitor of NF-kB is disclosed. Examples of NF-kB inhibitors include IkBα, PSI, a nucleotide sequence encoding IkBα anti-sense nucleic acid encoding an NF-kB sequence, such as Rel B, and anti-NF-kB antibodies. Examples of NF-kB inducers include NIK, MEKK, IKK2, TFRRF2, and Rel B. Also disclosed are vectors encoding inducers and inhibitors of NF-kB, for example adenoviral vectors.

7 Claims, 26 Drawing Sheets

OTHER PUBLICATIONS

Sharma et al., Multicomponent gene therapy vaccines for lung cancer: effective eradication of established murine tumors in vivo with interleukin-7/herpes simplex thymidine kinase-transduced autologous tumor and . Gene Ther. 1997 4:1361-70.*
Report and Recommendations of the Panel to Assess the NIH Investment in Research on Gene Therapy, Dec. 1995 p. 24.*
Gene Therapy's Growin Pains, Science. 1995, 25:1050, 1052-5.*
Scientific Considerations Related to Developing Follo-On Protein Products. Division of Dockets Management U.S. Food and Drug Administration Nov. 12, 2004, pp. 1-12.*
Wang et al., Dendritic cells transduced with an adenoviral vector encoding a model tumor-associated antigen for tumor vaccination. Hum Gene Ther. Jul. 20, 1997;8(11):1355-63.*
Rothe M Activation of NF-κB by inflammatory Cytokines, 1999, Sympsium in Immunology VIII, pp. 31-42.*
Tsatsanis et al., Tpl-2 induces IL-2 expression in T-cell lines by triggering multiple signaling pathways that activate NFAT and NF-kappaB. Oncogene. Nov. 19, 1998;17(20):2609-18.*
Guo et al., Antisense IRAK-2 oligonucleotide blocks IL-1-stimulated NF-kappaB activation and ICAM-1 expression in cultured endothelial Inflammation. Dec. 1999;23(6):535-43 cells.*
Zhang et al., Bacterial lipopolysaccharide activates nuclear factor-kappaB through interleukin-1 signaling mediators in cultured human dermal endothelial cells and mononuclear phagocytes.J Biol Chem. Mar. 19, 1999;274(12):7611-4.*
Granelli-Piperno A, et al., Coexpression of NF-kappa B/Rel and Sp1 transcription factors in human immunodeficiency virus 1-induced, dendritic cell-T-cell syncytia Proc Natl Acad Sci U S A. Nov. 21, 1995;92(24):10944-8.*
Tillman et al., Maturation of Dendritic Cells Accompanies High-Efficiency Gene Transfer by a CD40-Targeted Adenoviral Vector The Journal of Immunology, 1999, 162: 6378-6383.*
Foxwell et al.,High efficiency gene transfer is an efficient way of defining therapeutic targets: a functional genomics approach Ann Rheum Dis 2001;60:iii13-iii17.*
Lee et al., Cyclosporine a Inhibits the Expression of Costimulatory Molecules on in Vitro-Generated Dendritic Cells: Association with Reduced Nuclear Translocation of NuclearTransplantation, Nov. 15, 1999; 68 (9): 1255-63.*
Brown MD, Schatzlein AG, Uchegbu IF.Gene delivery with synthetic (non viral) carriers. Int J Pharm. Oct. 23, 2001;229(1-2):1-21.*
Eck et al., 1996 Goodman & Gilman's The Pharmacological Basis of Therapeutics, McGraw-Hill, New York, p. 77-101.*
Gorecki et al., 2001, Prospects and problems of gene therapy: an update Expert. Opin. Emerging Drugs, 6: 187-198.*
Banchereau et al., Dendritic cells and the control of immunity Nature, 1998 pp. 245-252.*
Ashley et al. "Bone marrow-generated dendritic cells pulsed with tumor extracts or tumor RNA induce antitumor immunity against central nervous system tumors" J. Exp. Med. 186:1177-1182 (1997).
Baeuerle & Baltimore "NF-κB: Ten years after" Cell 87:13-20 (1996).
Baeuerle & Henkel "Function and activation of NF-κB in the immune system" Ann. Rev. Immunol. 12:141-179 (1994).
Beauparlant & Hiscott "Biological and biochemical Inhibitors of the NF-κB/Rel proteins and cytokine synthesis" Cytokine & Growth Factor Reviews 7:175-190 (1996).
Bender et al. "Improved methods for the generation of dendritic cells from nonproliferation progenitors in human blood" J. Immunol. 196:121-135 (1996).
Bohl et al. "Control of erythropoietin delivery by doxycycline in mice after intramuscular injection of adeno-associated vector" Blood 92:1512-1517 (1998).
Boldin et al. "Self-association of the "death domains" of the p55 tumor necrosis factor (TNF) receptor and Fas/APO1 prompts signaling for TNF and Fas/APO1 effects" J. Biol. Chem. 270:387-391 (1995).
Bondeson et al. "Defining therapeutic targets by using adenovirus: Blocking NF-κB inhibits both inflammatory and destructive mechanisms in rheumatoid synovium but spares anti-inflammatory mediators" Proc. Natl. Acad. Sci. USA 96:5668-5673 (1999).

Bondeson et al. "Selective regulation of cytokine induction by adenoviral gene transfer of IκBα into human macrophages: Lipopolysaccharide-induced, but not zymosan-induced, proinflammatory cytokines are inhibited, but IL-10 is nuclear factor-κB independent" J. Immunol. 162:2939-2945 (1999).
Büeler "Adeno-associated viral vectors for gene transfer and gene therapy" Biol. Chem. 380:613-622 (1999).
Burns et al. "MyD88, an adapter protein involved in interleukin-1 signaling" J. Biol. Chem. 273:12203-12209 (1998).
Chow et al. "Toll-like receptor-4 mediates lipopolysaccharide-induced signal transduction" J. Biol. Chem. 274:10689-10692 (1999).
Delic et al. "The proteasome inhibitor lactacystin induces apoptosis and sensitizes chemo- and radioresistant human chronic lymphocytic leukaemia lymphocytes to TNF-α-initiated apoptosis" British J. Cancer 77:1103-1107 (1998).
Derossi et al. "Trojan peptides: The penetratin system for intracellular delivery" Trends Cell Biol. 8:84-87 (1998).
Feuillard et al. "Differential nuclear localization of p50, p52, and RelB proteins in human accessory cells of the immune response in situ" Eur. J. Immunol. 26:2547-2551 (1996).
Frankel et al. "Antisense oligonucleotide-induced inhibition of adrenocorticotropic hormone release from cultured human corticotrophs" J. Neurosurg. 91:261-267 (1999).
Girolomoni & Ricciardi-Castagnoli "Dendritic cells hold promise for immunotherapy" Immunol. Today 18:102-104 (1997).
Gong et al. "Induction of antigen-specific antitumor immunity with adenovirus-transduced dendritic cells" Gene Therapy 4:1023-1028 (1997).
Goodchild et al. "Inhibition of human immunodeficiency virus replication by antisense oligodeoxynucleotides" Proc. Natl. Acad. Sci. USA 85:5507-5511 (1988).
Goto et al. "Inhibitor effect of E3330, a novel quinone derivative able to supress tumor necrosis factor-α generation, on activation of nuclear factor-κB" Mol. Pharmacol. 49:860-873 (1996).
Grabbe et al. "Dendritic cells as initiators of tumor immune responses: A possible strategy for tumor immunotherapy?" Immunol. Today 16:117-121 (1995).
Granelli-Piperno et al. "Coexpression of NF-κB/Rel and Sp1 transcription factors in human immunodeficiency virus 1-induced, dendritic cell-T-cell syncytia" Proc. Natl. Acad. Sci. USA 92:10944-10948 (1995).
Griscavage et al. "Inhibitors of the proteasome pathway interfere with induction of nitric oxide synthase in macrophages by blocking activation of transcription factor NF-κB" Proc. Natl. Acad. Sci. USA 93:3308-3312 (1996).
Guijarro et al. "Lovastatin inhibits lipopolysaccharide-induced NF-κB activation in human mesangial cells" Nephrol. Dial. Transplant 11:990-996 (1996).
Haas et al. "Effect of proteasome inhibitors on monocytic IκB-α and β depletion, NF-κB activation, and cytokine production" J. Leukoc. Biol. 63:395-404 (1998).
Hart "Dendritic cells: Unique leuokocyte populations which control the primary immune response" Blood 90:3245-3287 (1997).
Hellerbrand et al. "Inhibition of NFκB in activated rat hepatic stellate cells by proteasome inhibitors and an IκB repressor" Hepatol. 27:1285-1295 (1998).
Hsu et al. "Vaccination of patients with B-cell lymphoma using autologous antigen-pulsed dendritic cells" Nature Medicine 2:52-58 (1996).
Huang et al. "NMR structure and mutagenesis of the Fas (APO-1/CD95) death domain" Nature 384:638-643 (1996).
Janeway et al. "Immunological tolerance: Danger—pathogen on the premises!" Curr. Biology 6:519-522 (1996).
Kazmi et al. "Suppression of NFκB activation and NFκB-dependent gene expression by tepoxalin, a dual inhibitor of cyclooxygenase and 5-lipoxygenase" J. Cell. Biochem. 57:299-310 (1995).
Kotake et al. "Inhibition of NF-κB, iNOS mRNA, COX2 mRNA, and COX catalytic activity by phenyl-N-tert-butylnitrone (PBN)" Biochem. Biophys. Acta 1446:77-84 (1998).
Kwak et al. "Transfer of myeloma idiotype-specific immunity from an actively immunised marrow donor" Lancet 345:1016-1020 (1995).

Lin et al. "(—)-Epigallocatechin-3-gallate blocks the induction of nitric oxide synthase by down-regulating lipopolysaccharide-induced activity of transcription factor nuclear factor-κB" Mol. Pharmacol. 52:465-472 (1997).

Lu et al. "Adenoviral delivery of CTLA4Ig into myeloid dendritic cells promotes their in vitro tolerogenicity and survival in allogeneic recipients" Gene Therapy 6:554-563 (1999).

Lum et al. "A new structural class of proteasome inhibitors that prevent NF-κB activation" Biochem. Pharmacol. 55:1391-1397 (1998).

Magari et al. "Pharmacologic control of a humanized gene therapy system implantend into nude mice" J. Clin. Invest. 100:2865-2872 (1997).

Martin & Papahadjopoulos "Irreversible coupling of immunoglobulin fragments to preformed vesicles" J. Biol. Chem. 257:286-288 (1982).

Matzinger "Tolerance, danger and the extended family" Annu. Rev. Immunol. 12:991-1045 (1994).

Méziére et al. "In vivo T helper cell response to retro-inverso peptidomimetics" J. Immunol. 159:3230-3237 (1997).

Murphy et al. "Phase I clinical trial: T-cell therapy for prostate cancer using autologous dendritic cells pulsed with HLA-A0201-specific peptides from prostate-specific membrane antigen" The Prostate 29:371-380 (1996).

Nagata "Mutations in the Fas antigen gene in *Ipr* mice" Immunol. 6:3-8 (1994).

Natarajan et al. "Caffeic acid phenethyl ester is a potent and specific inhibitor of activation of nuclear transcription factor NF-κB" Proc. Natl. Acad. Sci. USA 93:9090-9095 (1996).

Reddy et al. "A monocyte conditioned medium is more effective than defined cytokines in mediating the terminal maturation of human dendritic cells" Blood 90:3640-3646 (1997).

Rescigno et al. "Dendritic cell survival and maturation are regulated by different signaling pathways" J. Exp. Med. 188:2175-2180 (1998).

Rivera et al. "Long-term regulated expression of growth hormone in mice after intramuscular gene transfer" Proc. Natl. Acad. Sci. USA 96:8657-8662 (1999).

Romani et al. "Generation of mature dendritic cells from human blood an improved method with special regard to clinical applicability" J. Immunol. Meth. 196:137-151 (1996).

Roth & Spiegelberg "Activation of cloned human CD4 $Th_1$ and $Th_2$ cells by blood dendritic cells" Scand. J. Immunol. 43:646-651 (1996).

Rosenfeld et al. "Adenovirus-mediated transfer of a recombinant α-1-antitrypsin gene to the lung epithelium in vivo" Sciene 252:431-434 (1991).

Sato et al. "Quercetin, a bioflavonoid, inhibits the induction of interleukin 8 and monocyte chemoattractant protein-1 expression by tumor necrosis factor-α in cultured human synovial cells" J. Rheumatol. 24:1680-1684 (1997).

Schreck et al. "Dithiocarbamates as potent inhibitors of nuclear factor κB activation in Intact cells" J. Exp. Med. 175:1181-1194 (1992).

Sherman and Spatola "Compatibility of thioamides with reverse turn features: Synthesis and conformational analysis of two model cyclic pseudopeptides containing thioamides as backbone modifications" J. Am. Chem. Soc. 112:433-441 (1990).

Smith et al. "Anti-class II MHC antibodies prevent and treat EAE without APC depletion" Immunol. 83:1-8 (1994).

Specht et al. "Dendritic cells retrovirally transduced with a model antigen gene are therapeutically effective against established pulmonary metastases" J. Exp. Med. 186:1213-1221 (1997).

Steinman and Cohn "Identification of a novel cell type in peripheral lymphoid organs of mice" J. of Exp. Med. 137:1142-1163 (1973).

Szabolcs et al. "Retrovirally transduced human dendritic cells express a normal phenotype and potent T-cell stimulatory capacity" Blood 90:2160-2167 (1997).

Szabolcs et al. "Expansion of immunostimulatory dendritic cells among the myeloid progeny of human CD34 bone marrow precursors cultured with c-kit ligand, granulocyte-macrophage colony-stimulating factor, and TNF-α" J. Immunol. 154:5851-5861 (1995).

Tepper et al. "Deoxyspergualin inhibits k light chain expression in 70Z/3 pre-B cells by blocking lipopolysaccharide-induced NF-κB activation" J. Immunol. 155:2427-2436 (1995).

Thomson et al. "Recombinant polyepitope vaccines for the delivery of multiple CD8 cytotoxic T cell epitopes" J. Immunol. 157:822-826 (1996).

Thorsett et al. "Dipeptide mimics, conformationally restricted inhibitors of angiotensin-converting enzyme" Biochem. Biophys. Res. Comm. 111:166-171 (1993).

Tjoa et al. "Follow-up evaluation of prostate cancer patients infused with autologous dendritic cells pulsed with PSMA peptides" The Protstate 32:272-278 (1997).

Traenckner et al. "A proteasome inhibitor prevents activation of NF-κB and stabilizes a newly phosphorylated form of IκB-α that is still bound to NF-κB" EMBO J. 13:5433-5441 (1994).

Traencker & Baeuerle "Appearance of apparently ubiquitin-conjugated IκB-α during its phosphorylation-induced degradation in intact cells" J. Cell Sci. Suppl. 19:79-84 (1995).

Tüting et al. "Genetically modified bone marrow-derived dendritic cells expression tumor-associated viral or "self" antigens induce antitumor immunity in vivo" Eur. J. Immunol. 27:2702-2707 (1997).

Van der Bruggen et al. "A gene encoding an antigen recognized by cytolytic T lymphocytes on a human melanoma" Science 254:1643-1647 (1991).

Veber et al. "Conformationally restricted bicyclic analogs of somatostatin" Proc. Natl. Acad. Sci. USA 75: 2636-2640 (1978).

Waldmann & Cobbold "How do monoclonal antibodies induce tolerance? A role for infectious tolerance?" Annu. Rev. Immunol. 16:619-644 (1998).

Wan et al. "Dendritic cells transduced with an adenoviral vector encoding a model tumor-associated antigen for tumor vaccination" Hum. Gene Therapy 8:1355-1363 (1997).

Walther and Stein "Cell type specific and inducible promoters for vectors in gene therapy as an approach for cell targeting" J. Mol. Med. 74:379-392 (1996).

Witters et al. "Antisense oligonucleotides tot eh epidermal growth factor receptor" Breast Cancer Res. Treatment 53:41-50 (1999).

Yoneda et al. "Suppression by azelastine hydrochloride of NF-κB activation involved in generation of cytokines and nitric oxide" J. Pharmacol. 73:145-153 (1997).

Zanders et al. "Tolerance of T-cell clones is associated with membrane antigen changes" Nature 303:625-627 (1983).

Zanders et al. "Biochemical events initiated by exposure of human T lymphocyte clones to immunogenic and tolerogenic concentrations of antigen" Eur. J. Immunol. 15:302-305 (1985).

Zhou & Tedder "A distinct pattern of cytokine gene expression by human CD83 blood dendritic cells" Blood 86:3295-3301 (1995).

Baeuerle et al; "Function and Activation of NF-$_κ$B in the Immune System"; Ann Rev Immunol 1994, 12: 141-179, XP 000612175.

Makarov et al.; "NF-$_κ$B as a Target for Anti-Inflammatory Gene Therapy: Suppression of Inflammatory Responses in Monocytic and Stromal Cells by Stable Gene Transfer of $I_κBα$ $_cDNA$"; Gene Therapy, 1997, 4: 846-852, XP 002098098.

Bonvin et al. "Role of the amino-terminal domains of MEKKs in the activation of NFκB and MAPK pathways and in the regulation of cell proliferation and apoptosis" Cell. Signalling 14:123-131 (2002).

Saccani et al. "Modulation of NF-κB activity by exhcnage of dimers" Mol. Cell 11:1563-1574 (2003).

Smith et al. "NF-κB inducing kinase is dispensable for activation of NF-κB in inflammatory settings but essential for lymphotoxin β receptor activation of NF-κB in primary human fibroblasts" Immunol. 167:5895-5903 (2001).

Woronicz et al. "IκB kinase-β: NF-κB activation and complex formation with IκB kinase-α and NIK" Science 278:866-869 (1997).

Fung-Leung et al. "Tepoxalin, a novel immunomodulatory compounds, synergizes with CSA in suppression of graft-versus-host reaction and allogeneic skin graft rejection" Transplantation 60:362-368 (1995).

Kobayashi et al. "Curcumin inhibition of *Dermatophagoides farinea*-induced interleukin-5 (IL-5) and granulocyte macrophage-colony stimulating factor (GM-CSF) production by lymphocytes from bronchial asthmatics" Biochem. Pharmacol. 54:819-824 (1997).

Lee et al. "Anti-allergic actions of the leaves of *Castanea crenata* and isolation of an active component responsible for the inhibition of mast cell degranulation" Arch. Pharm. Res. 22:320-323 (1999).

Noguchi et al. "Inhibition of DF-protease associated with allergic diseases by polyphenol" J. Agric. Food Chem. 47:2969-2972 (1999).

Nomura et al. "Effect of deoxyspergualin on acute and chronic rejection in renal transplantation" Transplant. Proc. 30:3580-3581 (1998).

Wu et al. "The effect of macrophage depletion on delayed xenograft rejection: Studies in the guinea pig-to-C6-deficient rat heart transplantation model" Xenotransplantation 6:262-270 (1999).

Partial Search Report for European Appln. No. 07014428.2 mailed Aug. 11, 2008.

Park, A., et al., "Systematic Mutational Analysis of the Death Domain of the Tumor Necrosis Factor Receptor 1-associated Protein TRADD", *The Journal of Biological Chemistry*, 271(16): 9858-9862 (1996).

Mercurio, F., B. W. Murray, A. Shevchenko, B.L. Bennett, D.B. Young, J.W. Li, G. Pascual, A. Motiwala, H. Zhu, M. Mann, and A.M. Manning, "Ikappab Kinase (IKK)-Associated Protein 1, A Common Component Of The Heterogeneous IKK Complex." *Mol Cell Biol*, 19:1526-1538 (1999).

Bressler, P., K. Brown, W. Timmer, V. Bours, U, Siebenlist, and A.S. Fauci, "Mutational Analysis Of The P50 Subunit of NF-Kappa B And Inhibition Of NF-Kappa B Activity by Trans-Dominant p50 Mutants." *J Virol* 67:288-293 (1993).

Ganchi, P.A., S.C. Sun, W.C. Greene, and D.W. Ballard, "I Kappa B/MAD-3 Masks The Nuclear Localization Signal Of NF-Kappa B P65 And Requires The Transactivation Domain To Inhibit NF-Kappa B p65 DNA Binding," *Mol Biol Cell*, 3:1339-1352 (1992).

Le Bail, O., R. Schmidt-Ullrich, and A. Israel, "Promoter Analysis Of The Gene Encoding The I Kappa B-Alpha/MAD3 Inhibitor Of NF-Kappa B: Positive Regulation by Members Of The Rel/NF-Kappa B Family." *EMBO J*, 12:5043-5049 (1993).

Perkins, N.D., R.M. Schmid, C.S. Duckett, K. Leung, N.R. Rice, and G.J. Nabel, "Distinct Combinations Of NF-Kappa B Subunits Determine The Specificity Of Transcriptional Activation." *Proc Natl Acad Sci USA*, 89:1529-1533 (1992).

Read, M.A., M.Z. Whitley, A.J. Williams, and T. Collins, "NF-Kappa B And I Kappa B Alpha: An Inducible Regulatory System In Endothelial Activation." *J Exp Med*, 179:503-512 (1994).

Knop, J., H. Wesche, D. Lang, and M.U. Martin, "Effects Of Overexpression Of IL-1 Receptor-Associated Kinase On Nfkappab Activation, IL-2 Production and Stress-Activated Protein Kinases In The Murine T Cell Line EL4." *Eur J Immonol* 28:3100-3109 (1998).

Maschera, B., K. Ray, K. Burns, and F. Volpe, "Overexpression Of An Enzymically Inactive Interleukin-1-Receptor-Associated Kinase Activates Nuclear Factor-Kappab."*Biochem J*, 339 ( Pt 2):227-231 (1999).

Thomassen, E., T.A. Bird, B.R. Renshaw, M.K. Kennedy, and J.E. Sims, "Binding of Interleukin-18 To The Interleukin-1 Receptor Homologous Receptor IL-1Rrp1 Leads to Activation Of Signaling Pathways Similar To Those Used By Interleukin-1," *J Interferon Cytokine Res*, 18:1077-1088 (1998).

Faure, E., O. Equils, P.A. Sieling, L. Thomas, F.X, Zhang, C.J. Kirschning, N. Polentarutti, M. Muzio, and M. Arditi, "Bacterial Lipopolysaccharide Activates NF-Kappab Through Toll-Like Receptor 4 (TLR-4) In Cultured Human Dermal Endothelial Cells. Differential Expression Of TLR-4 And TLR-2 In Endothelial Cells." *J Biol Chem*, 275:11058-11063 (2000).

Ninomiya-Tsuji, J., K. Kishimoto, A. Hiyama, J. Inoue, Z. Cao, and K. Matsumoto, "The Kinase TAK1 Can Activate The NIK-I Kappab As Well As The MAP Kinase Cascade In The IL-1 Signalling Pathway." *Nature*, 398;252-256 (1999).

Yoshimura et al. "Effective Antigen Presentation By Dendritic Cells Is NF-κb Dependent: Coordinate Regulation Of MHC, Co-Stimulatory Molecules And Cytokines," *Int Immunol*, 13(5): 675-683 (2001).

Poligone, B., D.J. Weaver, Jr., P. Sen, A.S. Baldwin, Jr., and R. Tisch, "Elevated NF-Kappab Activation in Nonobese Diabetic Mouse Dendritic Cells Results In Enhanced APC Function," J Immunol 168:188-196, (2002).

Sen, P., S. Bhattacharyya, M. Wallet, C.P. Wong, B. Poligone, M. Sen, A.S. Baldwin, Jr., and R. Tisch., "NF-Kappa B Hyperactivation Has Differential Effects On The APC Function Of Nonobese Diabetic Mouse Macrophages." *J Immunol* 170:1770-1780 (2003).

Miyazaki et al. "Reciprocal role of ERK and NF-κB pathways in survival and activation of osteoclasts" *J. Cell. Biol.* 148:333-342 (2000).*

Muzio et al. "The human toll signaling pathway: divergence of nuclear factor κB and JNK/SAPK activation upstream of tumor necrosis factor receptor-associated factor 6 (TRAF6)" *J. Exp. Med.* 187:2097-2101 (1998).*

Nabel & Verma "Proposed NF-κB / IκB nomenclature" Genes Dev. 7:2063 (1993).*

Neumann et al. "CD40, but not lipopolysaccharide and anti-IgM stimulation of primary B lymphocytes, leads to a persistent nuclear accumulation of RelB" *J. Immunol.* 157:4862-4869 (1996).*

O'Connell et al. "Role of IKK1 and IKK2 in lipopolysaccharide signaling in human monocytic cells" *J. Biol. Chem.* 273:30410-30414 (1998).*

Weih et al. "Multiorgan inflammation and hematopoietic abnormalities in mice with a targeted disruption of RelB, a member of the NF-κB/Rel family" *Cell* 80:331-340 (1995).*

Yoshimura et al. "Role of NF-κB in antigen presentation and development of regulatory T cells elucidated by treatment of dendritic cells with the proteasome inhibitor PSI" *Eur. J. Immunol.* 31:1883-1893 (2001).*

* cited by examiner

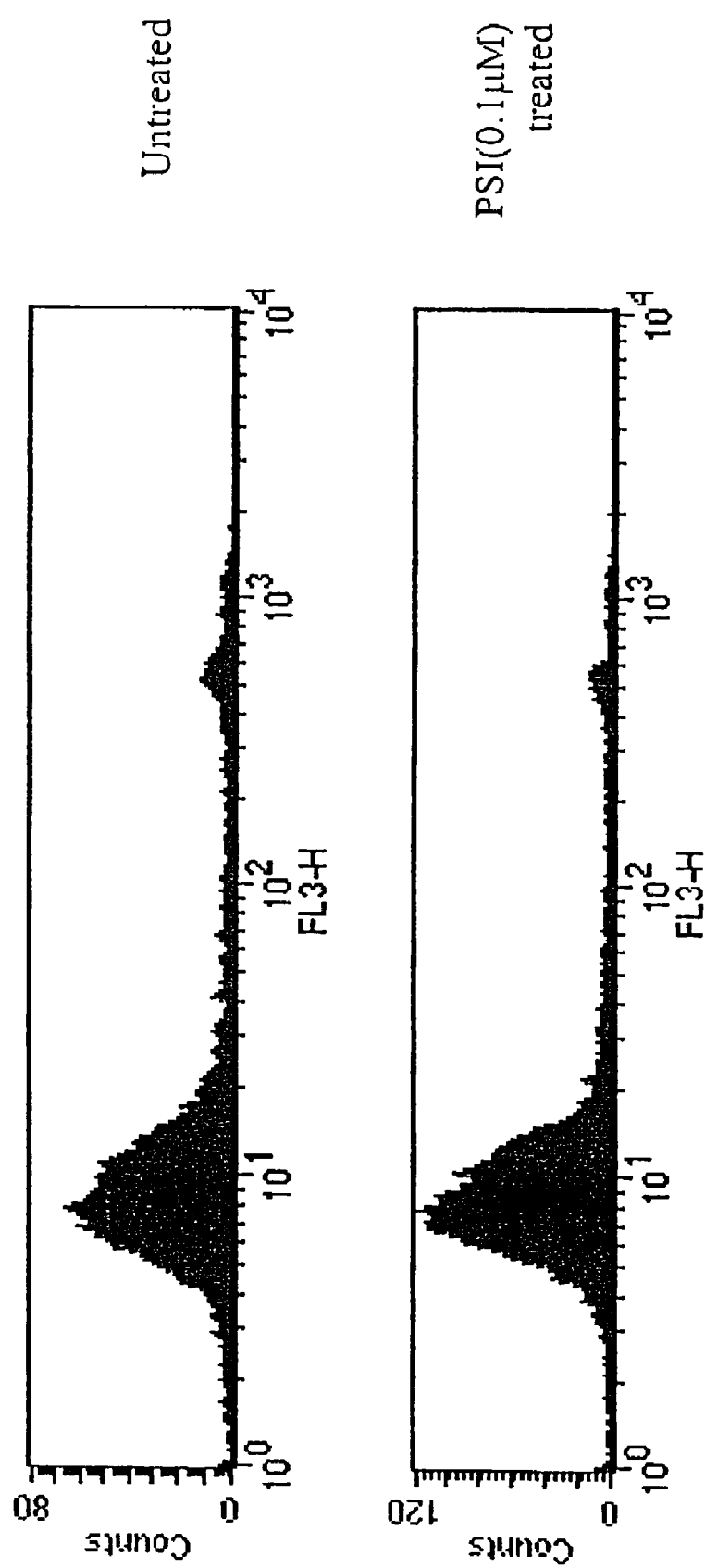
Figure 1 (page 1 of 2)

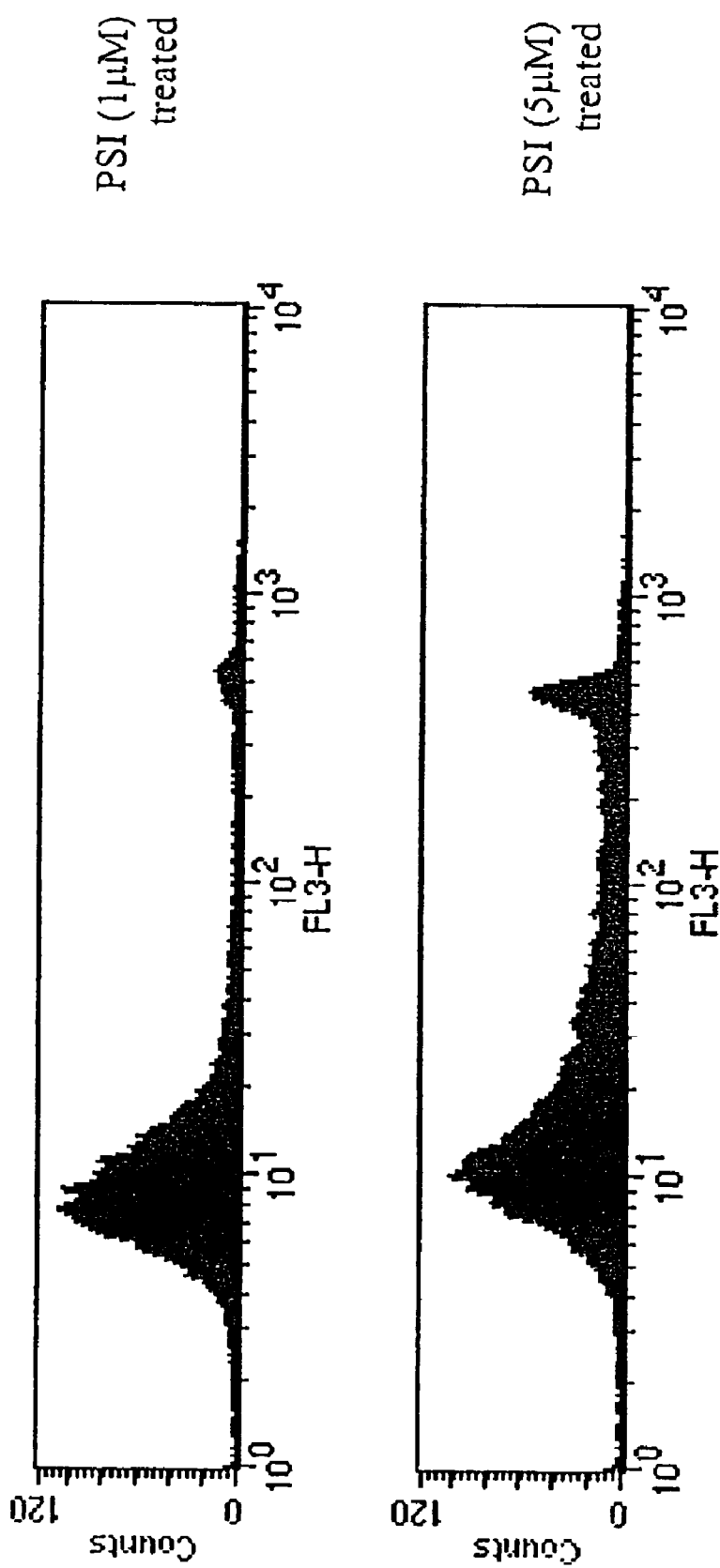
Figure 1 (page 2 of 2)

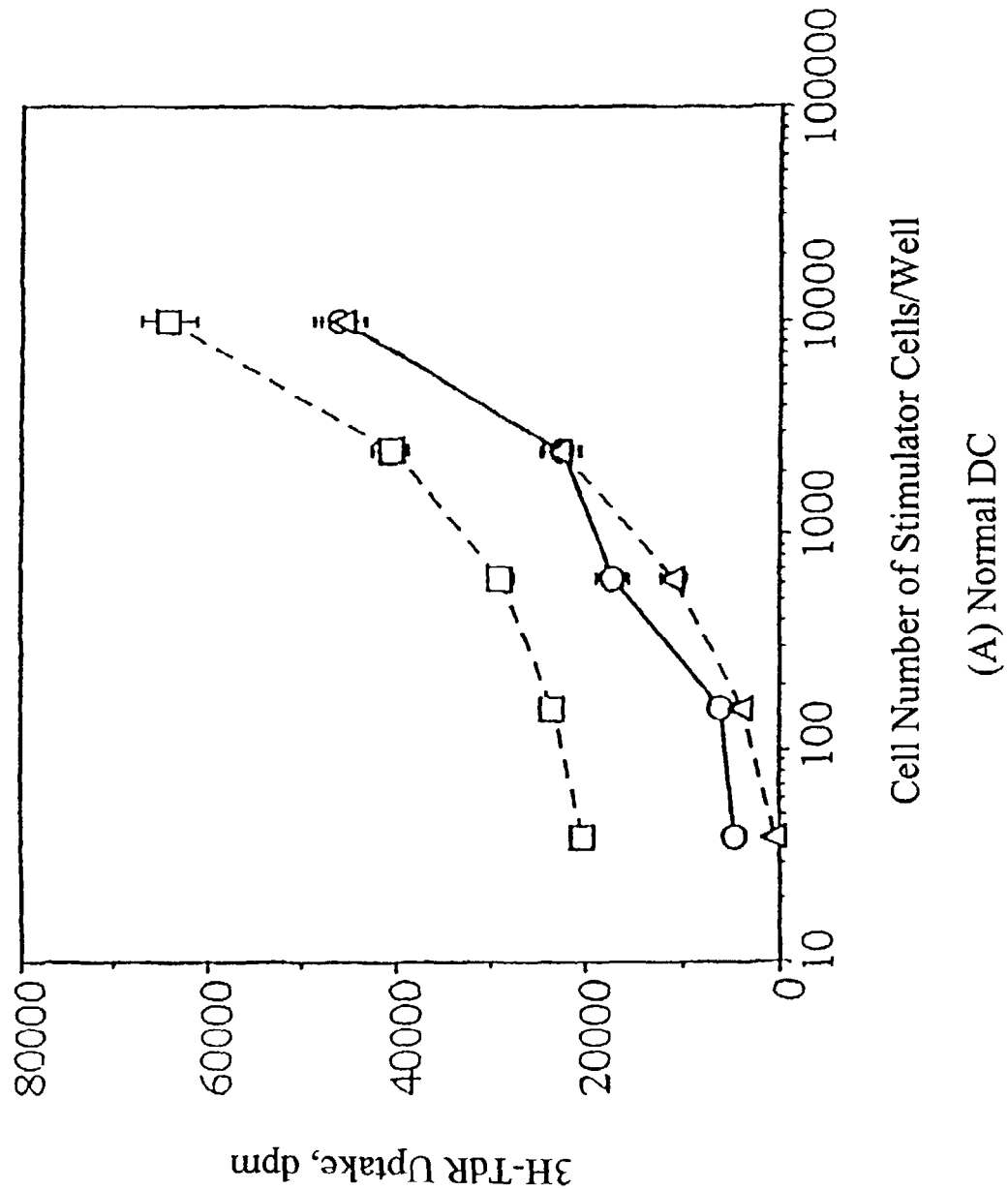
Figure 4 (page 1 of 2)
(A) Normal DC (page 2 of 2)

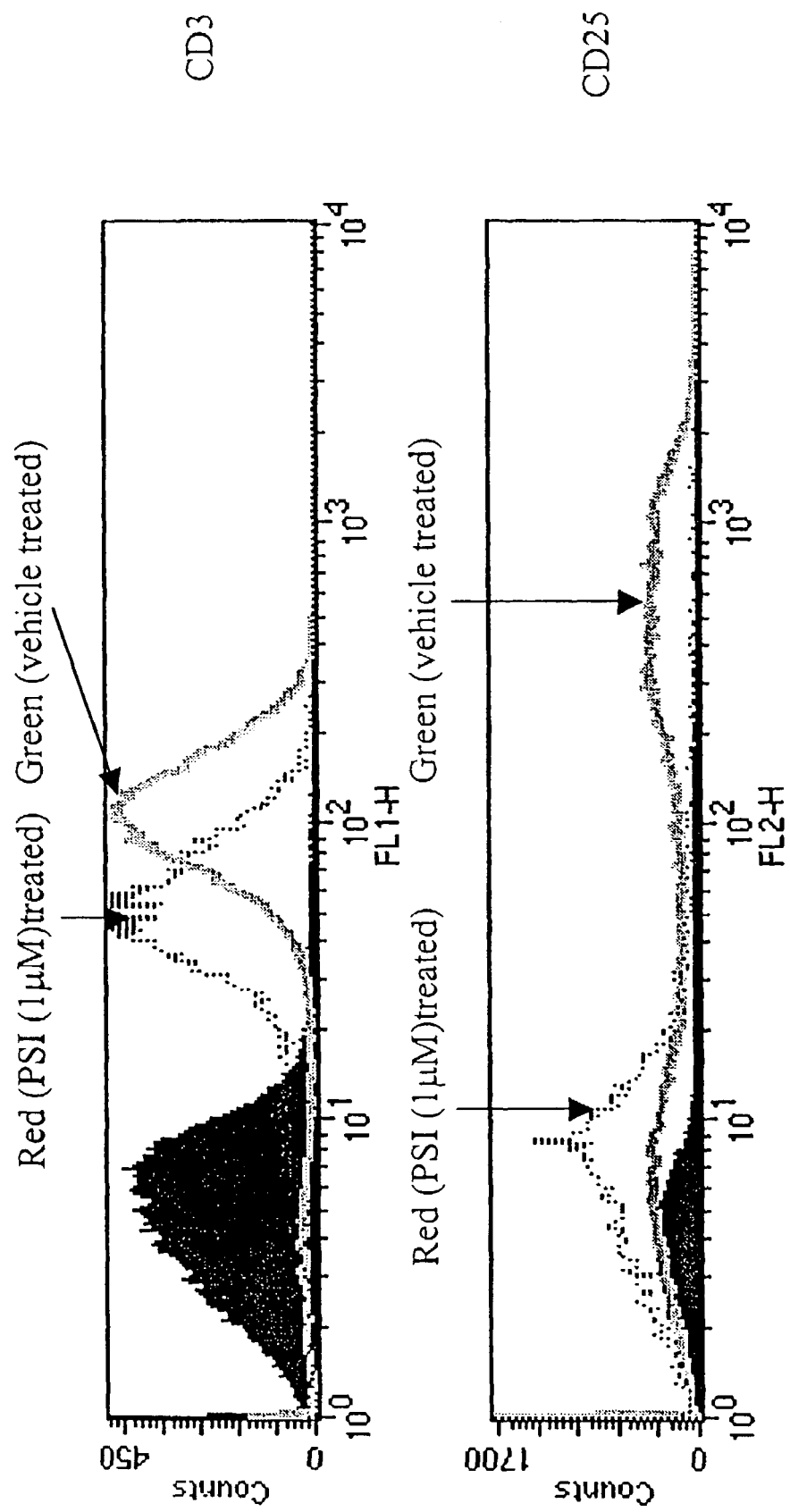
Figure 7 (page 1 of 2)

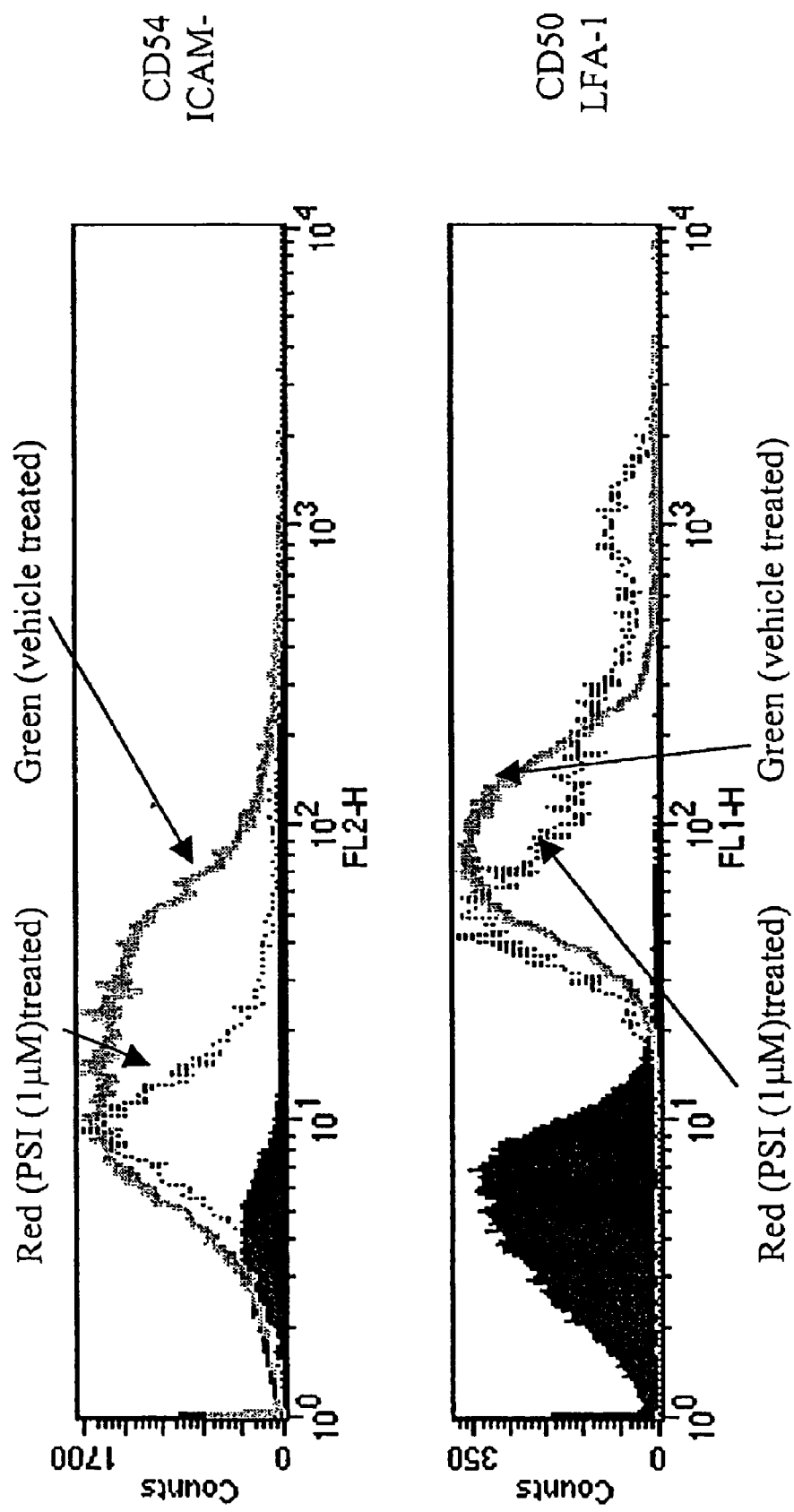
Figure 7 (page 2 of 2)
Reduced expression of surface antigens on allo-lymphocytes by PSI pre-treated DC

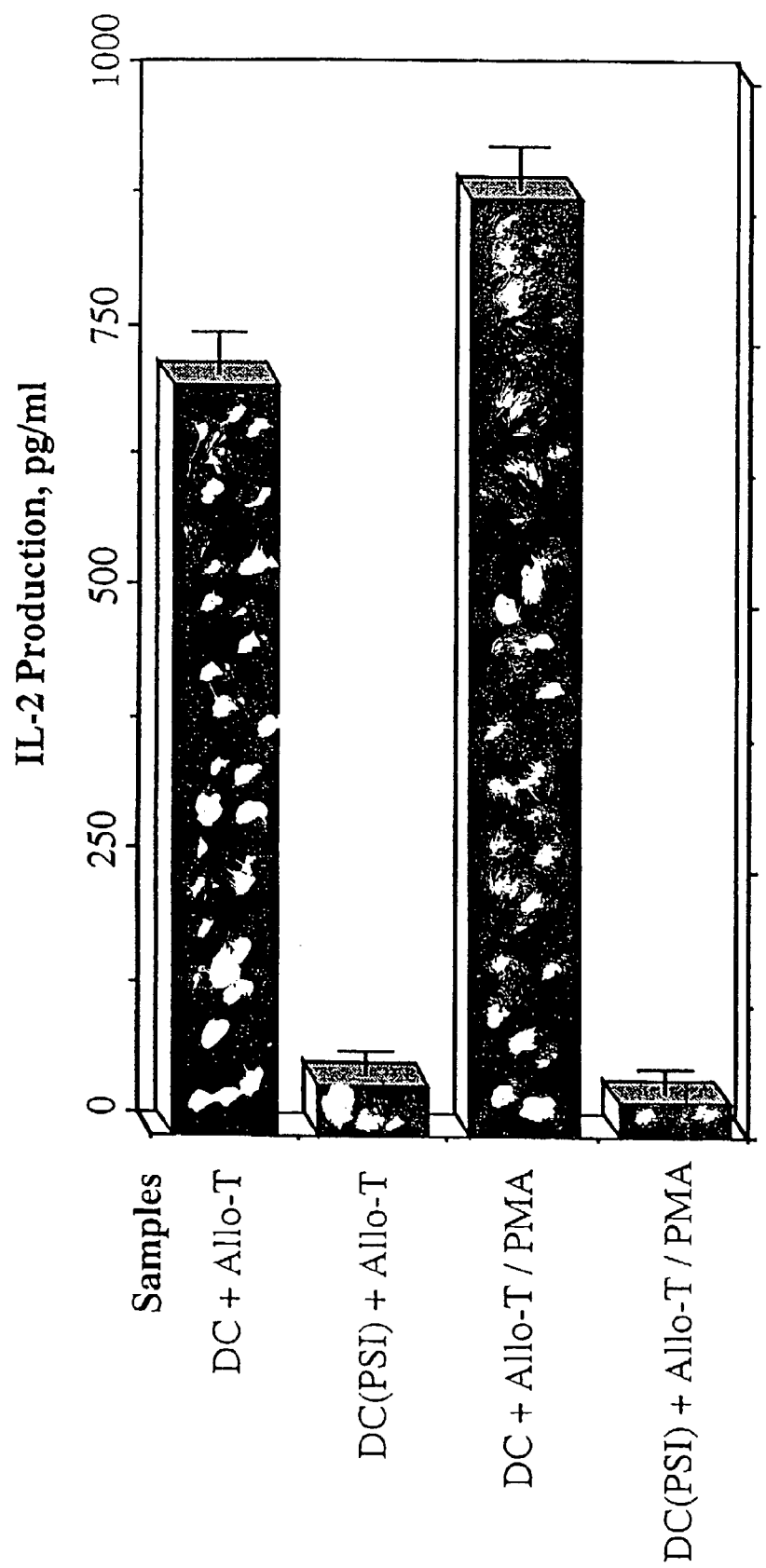
Figure 8 (page 1 of 3)

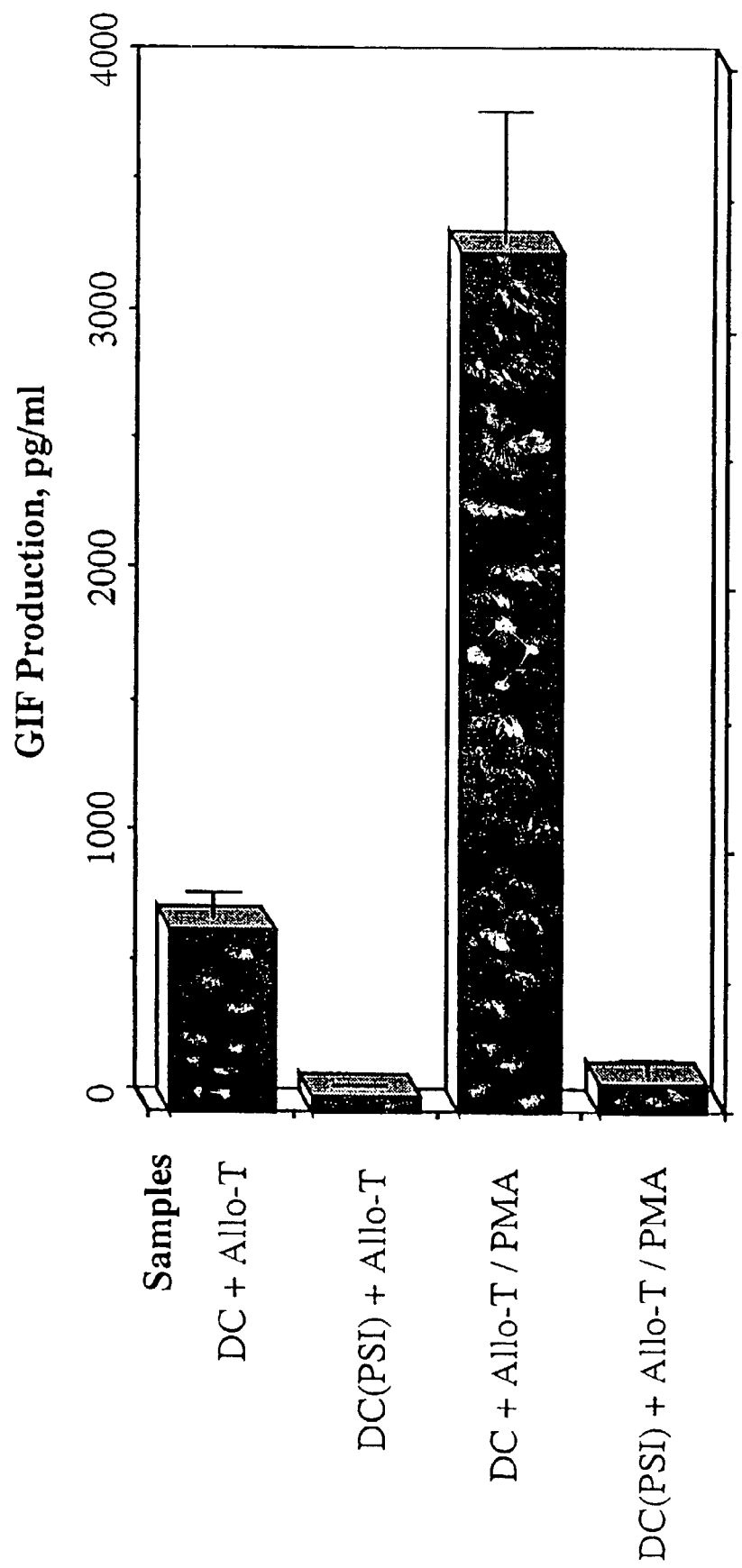
Figure 8 (page 2 of 3)

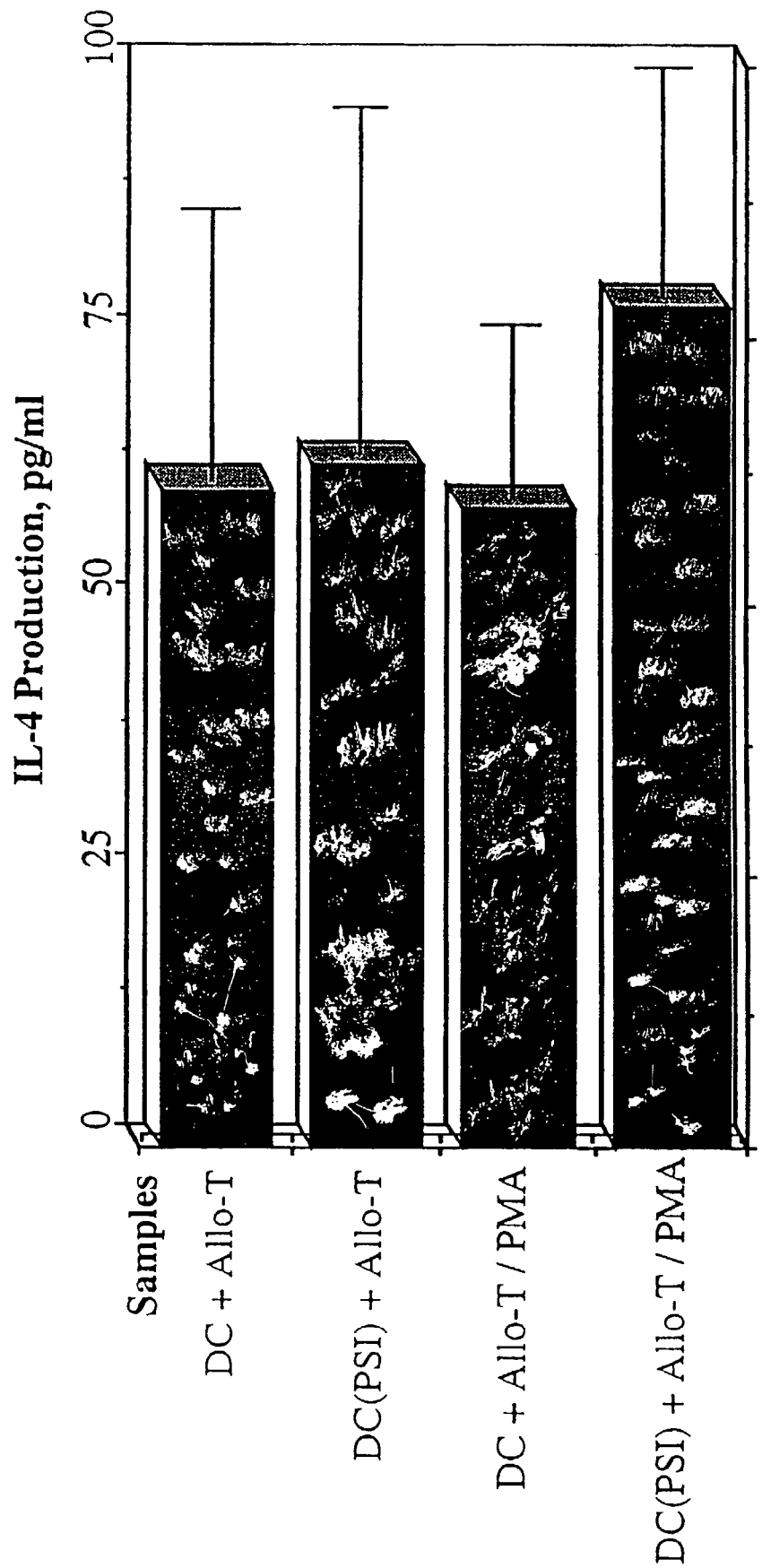
Figure 8 (page 3 of 3)

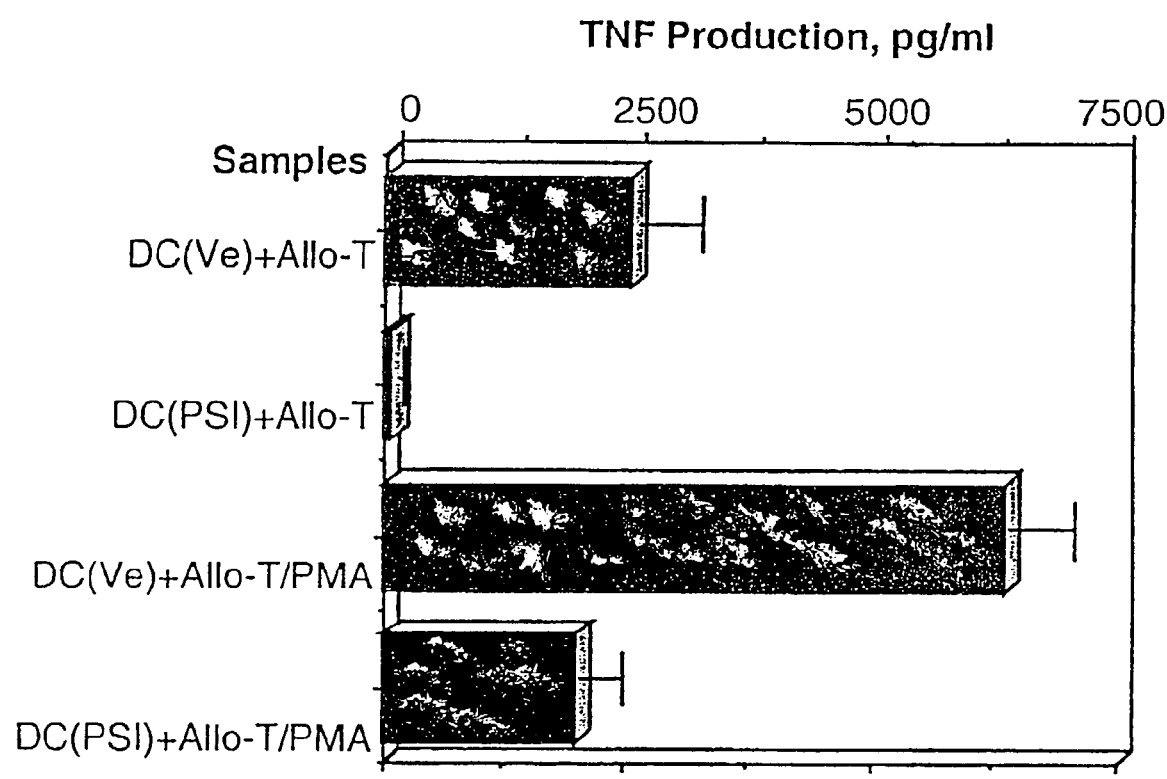
Figure 9 (page 1 of 2)

Figure 9 (page 2 of 2)
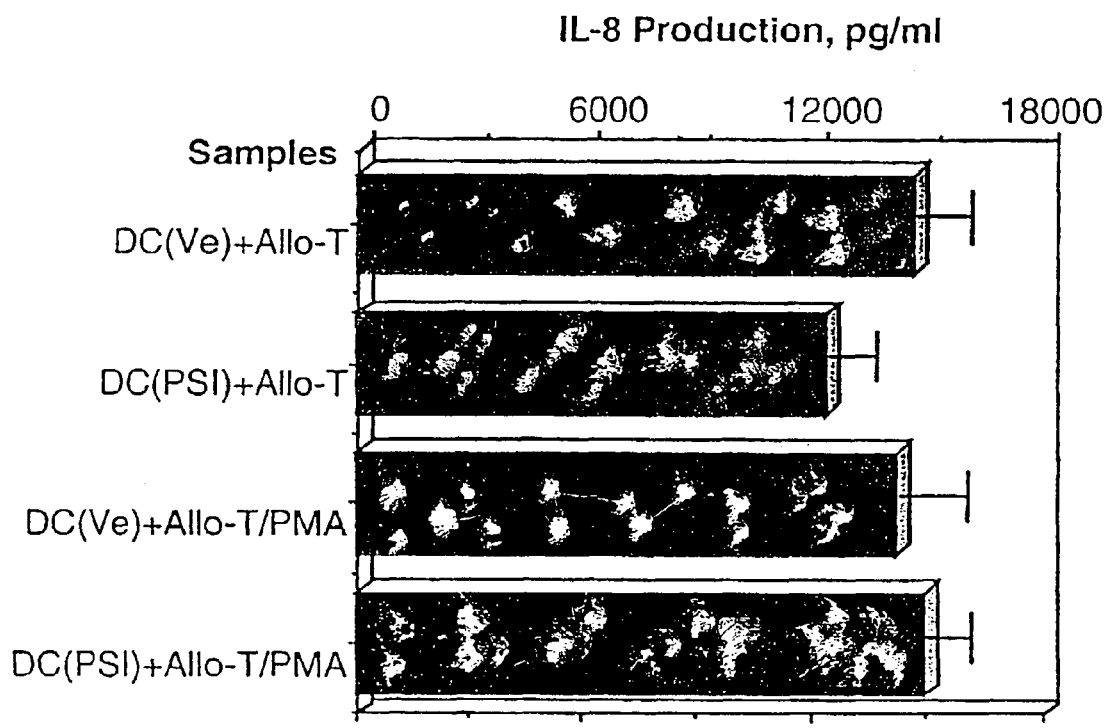
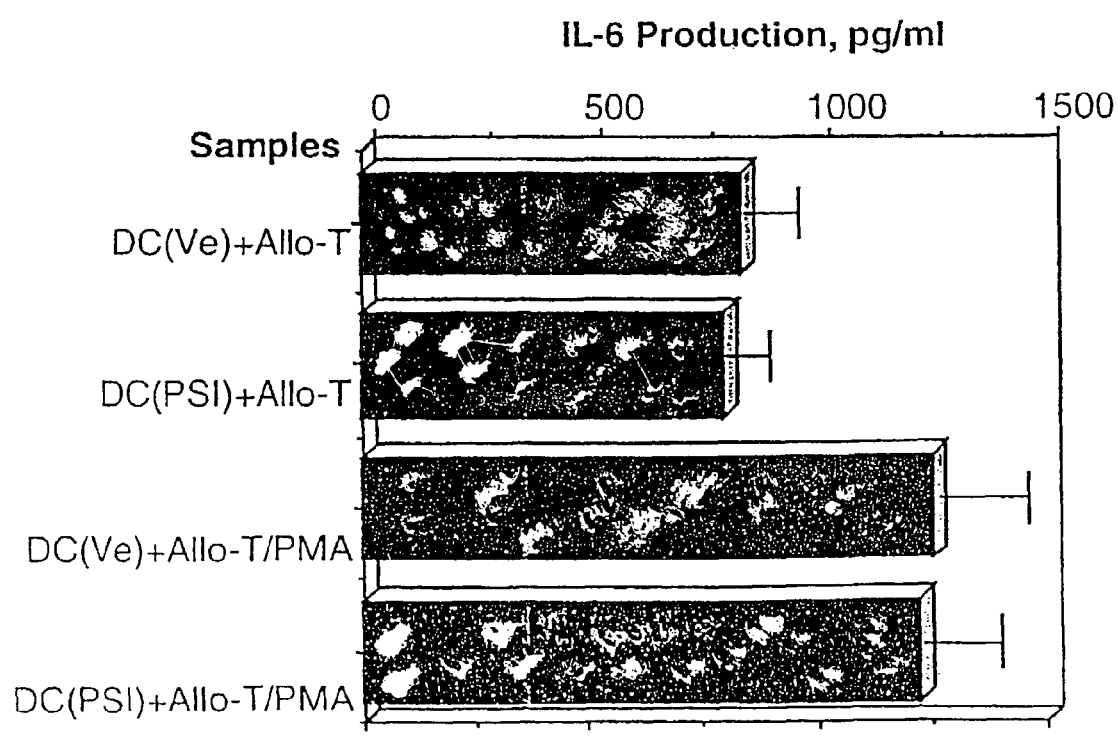

Overexpression of MyD88-lpr intoimmature dendritic cells induces NF-κB activation Overexpression of MyD88lpr enhances expression of CD80 and CD86 in immature DC

Activation of p38 MAPK in human macrophages by blocking MyD88

(a) Macrophages
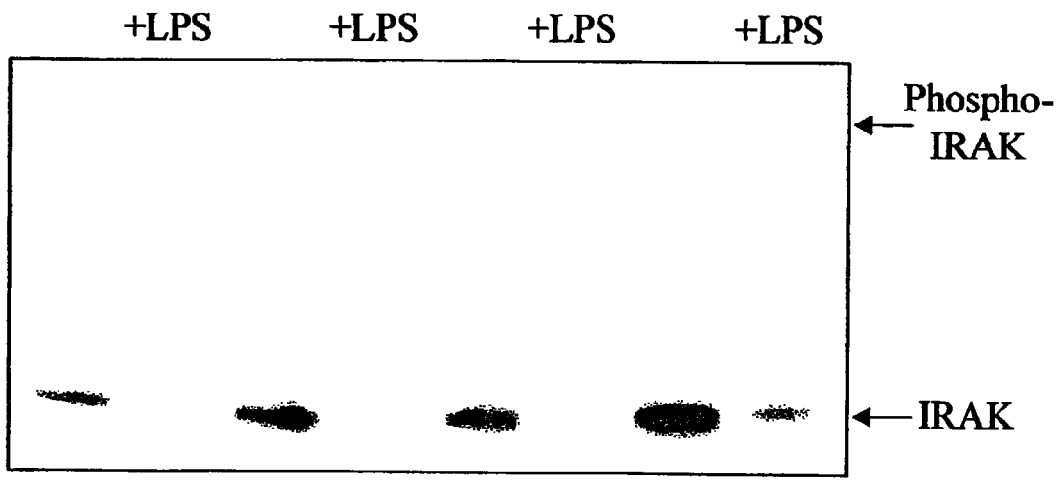
(b) HELA
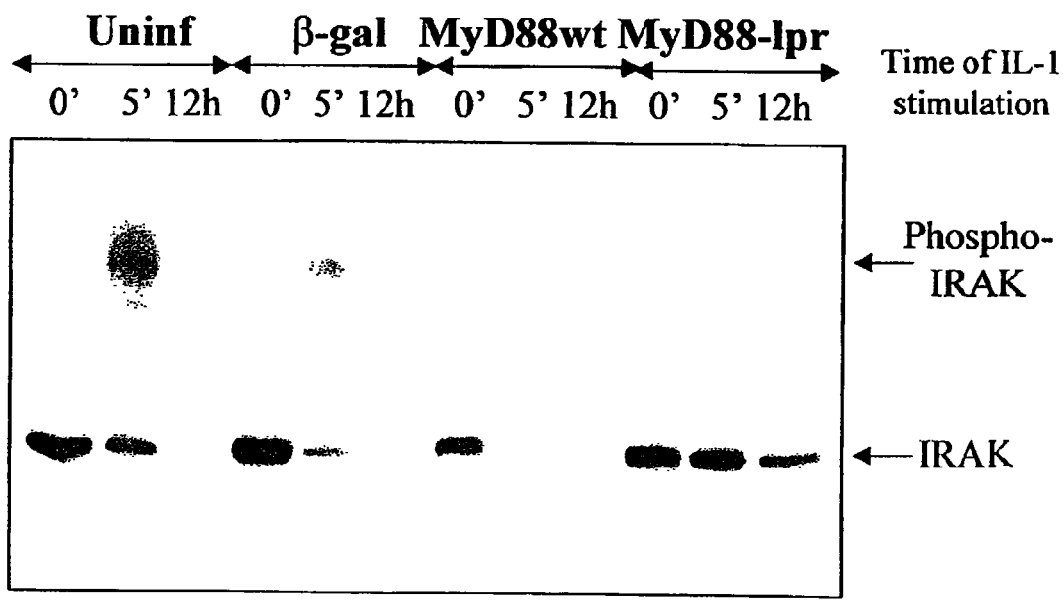
Figure 18

Overexpression of dominant negative MyD88 induces IκBα phosphorylation in human macrophages

Macrophage cytokine production after 2 days overexpression

|            | TNFα (pg/ml)      | IL-6 (pg/ml) | IL-8 (pg/ml) |
|------------|-------------------|--------------|--------------|
| Uninfected | <20               | <50          | 1000-3000    |
| Ad0        | <20               | <50          | 1000-3000    |
| AdMyD88wt  | <20               | <50          | 1000-3000    |
| AdMyD88-lpr| 40-500 (max 1000) | 500-1500     | 10000-15000  |

Time-course of macrophage cytokine production after infection with AdMyD88-lpr

|     | TNFα (pg/ml) | IL-6 (pg/ml) | IL-8 (pg/ml) |
|-----|--------------|--------------|--------------|
| 0h  | <20          | <70          | 1700         |
| 4h  | <20          | <70          | 2200         |
| 24h | 170          | 490          | 14200        |
| 48h | 70           | 750          | 13500        |

Figure 20

ACTIVATION AND INHIBITION OF THE IMMUNE SYSTEM

This application is a national phase application of International Patent Appln. No. PCT/GB00/04925 filed Dec. 22, 2000, which designated the United States and was published in English.

The invention relates to the activation and inhibition of the immune system by using inducers and inhibitors of NF-κB, and to the use of such inducers and inhibitors to treat transplant rejection, autoimmune disease, allergy, infectious disease and cancer.

Antigen presentation is a critical step in the initiation of the immune response, and dendritic cells (DC) are acknowledged to be the most potent antigen presenting cells for naïve T cells. This is partly due to their high expression of MHC and costimulatory molecules (Hart (1997) *Blood* 90, 3245-3287). However, little is known about the biochemical pathways which regulate antigen presenting function, partly due to the difficulty in transfecting DC. Using an inhibitor of IκB degradation, PSI that produces an effective inhibition of NF-κB activation, the inventors show here abrogation of the capacity of DC to induce a mixed lymphocyte reaction. The mechanism suppressed DC function and diminished antigen presentation involved downregulation of multiple steps, including costimulatory molecules (CD86 and CD80), HLA class II (DQ>DR) as well as cytokines such as IL-12. Moreover, T cell exposed to such DC were unable to be stimulated by subsequent encounters with normal DC. These results point out NF-κB as an effective target for blocking antigen presentation.

Dendritic cells are of major importance in the presentation of antigen to naive T cells in the primary immune response. They are bone marrow derived cells which were first described in the early 1970's by Steinman and Cohn (1973) *J. Exp. Med* 179, 1109. Studies on dendritic cells were initially hampered by the difficulty in isolating them in sufficient numbers, but this problem was overcome in part by the realisation that a subset of DC could be generated in vitro by culture of CD34+ cells or human monocytes with GM-CSF and IL-4. These cultured DC have the phenotype of immature DC, and can be matured into high MHC, high CD80/86 expressing cells through incubation with TNFα or LPS (Bender et al (1996) *J. Immunol. Methods* 196, 121; Romani et al (1996) *J. Immunol. Methods* (1996) 196, 137; Reddy et al (1997) *Blood* 90, 3640).

DC can also be derived from a post colony-forming unit CD14+ intermediate in the peripheral blood. DC migrate to peripheral sites in skin, mucosa, spleen and thymus. They have been implicated in a variety of clinically important processes, including allograft rejection, atopic disorders, autoimmunity and anti-tumour immunity.

DC can be cultured ex vivo from CD34+ stem cells or CD14+ peripheral blood monocytes using cytokines, principally GM-CSF, IL-4 and TNFα Scabolsc et al (1995) *J. Immunol.* 154, 5651-5661. DC from both these sources are immunocompetent and can take up exogenously presented antigen, process it and then present it to cytotoxic T-cells (Grabbe et al (1995) *Immunology Today* 16, 117-121; Girolomoni & Ricciardi-Castagnoli (1997) *Immunology Today* 18, 102-104). DC can transfer antigen-specific tumour immunity generated in vivo (Kwak et al (1995) *Lancet* 345, 1016-1020) and autologous DC pulsed with tumour antigen ex vivo can induce a measurable anti-tumour effect (Hsu et al (1996) *Nature Medicine* 2, 52-58). DC can be effectively pulsed using a crude tumour membrane lysate, purified peptides or peptide fragments. The ex vivo expansion of autologous dendritic cells from patients, loading with a peptide antigen and reinfusion as adoptive immunotherapy, is described in, for example, WO/00/26249.

The importance of antigen presentation in the generation of immune response was confirmed by demonstration that blocking antigen presentation downregulates immune responses and is useful in treating animal models of disease. Thus antibody to murine MHC class II has been used to treat experimental allergic encephalomyelitis (Smith et al (1994) *Immunology* 83, 1), and blocking the CD80/86 costimulatory molecules with antibodies or CTLA4-Ig fusion protein is beneficial in transplants or animal models of arthritis (Lu et al (1999) *Gene Ther.* 6, 554-563). This has led to a search of new ways of downregulating antigen presentation which may be useful in human diseases or in transplantation.

NF-κB has been speculated as being involved in the immune system. This is summarised in, for example, the paper by Baeueurle P. A. and Henkel T. (Annual Reviews in Immunology, 1994, Vol. 12, pages 141-179). However, no-one has shown that NF-κB is indeed crucial in the activation and inhibition of the immune system, as the effects of activating or inactivating NF-κB on antigen representing cells were not amenable to study previously. The inventors, for the first time, have demonstrated the key role of NF-κB in the immune response.

The activation of the transcription factor NF-κB like proteins results from post-translational modification permitting translocation of the preformed transcription factor from the cytoplasm to the nucleus. This translocation is controlled by the phosporylation and degradation of an inhibitor protein called IκB, which forms a complex with NF-κB, and thereby holds it in the cytoplasm. Stimulation of the cell by appropriate signals leads to modification of IκB which in turn results in its dissociation and/or degradation from NF-κB.

Binding of the IκB protein to NF-κB masks the nuclear localisation signal (NLS) of NF-κB. Upon stimulation of the cell with specific agents, which depend on the cell type and stage of cell development, IκB is modified in a way that disables binding to NF-κB, leading to dissociation of NF-κB from IκB.

NF-κB is a heterodimeric protein consisting of a 50 kD subunit (p50) and a 65 kD subunit (p65). The cDNAs for p50 and p65 have been cloned and have been shown to be homologous over a region of 300 amino acids.

Recently an additional member of the NF-κB family, Rel B, has been cloned as an immediate early response gene from serum-stimulated fibroblasts.

Both p50 and p65 are capable of forming homodimers, although with different properties: whereas p50 homodimers have strong DNA binders affinity but cannot transactivate transcription, the p65 homodimers can only weakly bind to DNA but are capable of transactivation. P50 is synthesised as the amino-terminal part of the 110 kD precursor (p 110), which has no DNA binding and dimerisation activity. The carboxyl-terminal part contains eight ankyrin repeats, a motif found in several proteins involved in cell cycle control and differentiation.

Five IκB family members have been identified: IκBα, IκBβ, p105/IκBγ, p110/IκBΔ and IκBε (Baeuerle and Baltimore, Cell 1996, Vol. 87, pages 13-20). All IκB-like family members contain multiple ankyrin repeats, which are essential for inhibition of NE-κB activation.

The inventors have found that many of the key features of the inflammatory response in human macrophages and in the rheumatoid synovium were dependent on the transcription factor NF-κB. The inventors have studied the proteosome inhibitory drug PSI, which was initially described as an inhibitor of the chymotrypsin-like activity of the proteosome. It was found that the production of many proinflammatory mediators, such as TNFα, IL-6, IL-2 were dependent on NF-κB (inhibitable by AdvIκBα disclosed in PCT/GB98/02753) whereas the anti-inflammatory cytokines and mediators, namely IL-10, IL-1 receptor antagonist, IL-11 were not affected. This suggested to us that NF-κB segregated accurately between these two classes of mediators, and so raised the question, in view of the close relationship of the inflammatory and immune systems of what the role of NF-κB might be in the induction of immunity.

The inventors first investigated the effect of the proteosome inhibitory drug PSI, which does not require the use of gene therapy. This is known to inhibit IκB degradation and hence NF-κB activation on the immunostimulatory function of dendritic cells, which is the key early event on the generation of a primary immune response.

They report that PSI treatment of mature, monocyte derived DC inhibited their capacity to induce T cell proliferation in the mixed lymphocyte response. To elucidate the mechanism of this effect, cell surface analysis, cytokine assays and co-cultures were performed, which suggested that blocking NF-κB permits immunosuppressive mechanisms to become operational in the interaction between the dendritic cells and the T cells.

Furthermore, the inventors have demonstrated that the changes result in an anergic response. That is, they result in the inability to produce an immune response, even after removal of the original inhibiting compound.

The inventors have also realised that NF-κB can also be used as a target to induce or modulate an immune response. This is unexpected, as it has been shown Feuillard et al (1996) *Eui. J Immunol* 26, 2547-2551; Granelli-Piperno et al (1995) *Proc Natl. Acad. Sci. USA* 92, 10944-10948 the NF-κB is already activated in DC, and hence further activation would not have been expected to be beneficial.

A first aspect of the invention provides a method of inhibiting antigen presentation or inducing an anergic response in a mammal, such as a human, comprising administering a pharmaceutically-effective dose of an intracellular inhibitor of APC, such as DC, function.

By "intracellular inhibitor of APC function" we include any suitable inhibitor of antigen presenting cell function. By "APC function" we include the ability to present antigen, the ability to express MHC Class II, the ability to express cell surface molecules such as costimulatory molecules including CD80 and CD86, the ability to produce cytokines and the ability to induce anergy rather than activation. Typically the inhibitor of APC function is an inhibitor of DC function. Preferably, the inhibitor is an inhibitor of intracellular signalling within the APC. By "intracellular signalling within the APC" we include communication between the membrane and the nucleus, signalling which controls gene expression (including expression of CD80 and CD86) and control of cytoskeletal organisation. Inhibition of intracellular signalling include, for example, an inhibitor of NF-κB as described in more detail below.

For the avoidance of doubt, cytokines and molecules containing CPG motifs are not intracellular inhibitors of APC function since they act extracellularly. Clearly, the inhibitors are ones that do not kill the cell.

A further aspect of the invention provides a method of inhibiting antigen presentation or inducing an anergic response in a mammal comprising administering a pharmaceutically-effective dose of an inhibitor of NF-κB.

By pharmaceutically-effective dose, we mean an amount sufficient to induce the desired response in a mammal. This amount can be determined by routine clinical and experimental trials known in the art.

By mammal, we mean any mammal but especially a human.

Anergy is a form of immunological tolerance in which lymphocytes, in this case T lymphocytes after exposure to antigen in an inappropriate setting become refractory to subsequent optional immunogenic stimulus, usually the immunogenic dose of antigen in the context of activated antigen presenting cells (see Roitt, I., Broskoff, J. and Male, D. (1998, 5th edition) Immunology, Mosby, London). Thus, the invention provides methods in which a tolerogenic response is induced in a mammal.

Antigen presentation describes the display of antigen as peptide fragments bound to MHC molecules on the surface of a cell; T cells recognise antigen only when it is presented in this way.

A further aspect of the invention provides a method of treating an allergy or an autoimmune disease comprising administering a pharmaceutically-effective dose of an intracellular inhibitor of APC, such as DC, function to induce an anergic response in a mammal.

A further aspect of the invention provides a method of treating an allergy or an autoimmune disease comprising administering a pharmaceutically-effective amount of an inhibitor of NF-κB to induce an anergic response in a mammal. The autoimmune disease may be any autoimmune disease such as rheumatoid arthritis, type I diabetes, multiple sclerosis, Crohn's disease, Hashimoto's thyroiditis, coeliac disease, myasthenia gravis, pemphigus vulgaris, systemic lupus erythromatosus and Graves disease.

Allergies which may be treatable by the method described herein include allergies to the following allergens: Fel d 1 (the feline skin and salivary gland allergen of the domestic cat *Felis domesticus*—the amino acid sequence of which is disclosed in WO 91/06571), Der p I, Der p II, Der fI or Der fII (the major protein allergens from the house dust mite dermatophagoides—amino acid sequences disclosed in WO 94/24281).

The invention is applicable substantially to any allergy, including those caused by allergens present in any of the following: grass, tree and weed (including ragweed) pollens; fungi and moulds; foods eg fish, shellfish, crab lobster, peanuts, nuts, wheat gluten, eggs and milk; stinging insects eg bee, wasp and hornet and the chirnomidae (non-biting midges); spiders and mites, including the house dust mite; allergens found in the dander, urine, saliva, blood or other bodily fluid of mammals such as cat, dog, cows, pigs, sheep, horse, rabbit, rat, guinea pig, mouse and gerbil; airborne particulates in general; latex; and protein detergent additives.

Allergies to proteins from the following insects may also be treated: housefly, fruit fly, sheep blow fly, screw worm fly, grain weevil, silkworm, honeybee, non-biting midge larvae, bee moth larvae, mealworm, cockroach and larvae of *Tenibrio molitor* beetle.

A further aspect of the invention provides a method of preventing transplant rejection in a mammal, such as a human, comprising administering a pharmaceutically-effective dose of an intracellular inhibitor of APC, such as DC, function to induce an anergic response in a mammal.

A further aspect of the invention provides a method of preventing transplant rejection comprising administering a pharmaceutically-effective amount of NF-κB inhibitor to induce an anergic response.

The invention further relates to inhibitor of APC function such as NF-κB inhibitors for use as a medicament, to induce an anergic response, to inhibit the rejection of transplanted tissue, or as anti-autoimmune disease agents or to treat allergy.

The invention also provides a NF-κB inhibitor for use in the manufacture of a medicament to treat transplant rejection, allergy or an auto-immune disease.

Preferably the NF-κB inhibitor is an inhibitor of proteolysis, for example a proteosome inhibitor. The inhibitor may be PSI, available from Calbiochem. This is known as an inhibitor of proteosomes (Traechner, et al., EMBO J. (1994), Vol. 13, pages 5433-41; Griscavage, et al., PNAS (1996), Vol. 93, pages 3308-12; Bondeson, et al., J Immunol. (1999), Vol. 162, pages 2939-45). ALLN (Jobin, et al., Hepatology (1998), Vol. 27, pages 1285-95); Lactacystin (Delic, et al. (1998), Vol 77, pages 1103-07); MG-132 (Jobin, et al. Supra); C-LFF and Calpain Inhibitors (Neauparfant and Hiscott, Cytokine & Growth Factor Reviews (1996), Vol. 7 pages 175-190); or CVT-134 (Lum, et al., Biochem. Pharmacol (1998), Vol. 55, pages 1391-97) may also be used as inhibitors.

Other inhibitors include: Caffeic acid phenethyl ester (Natarajan, et al., PNAS (1992), Vol. 93 pages 9090-95); Pyrrolidine dithiocarbonate (Schreck, et al., J. Exp. Med. (1992), Vol. 175, pages 1181-94); Lovastatin (Guijarro, et al., Nephrol Dial Transplant (1996), Vol. 11, pages 990-996); Aselastine HCL (Yoneda, Japan. J. Pharmacol. (1997), Vol. 73, pages 145-153); Tepaxalin (Kazmi, et al., J Cell. Biochem. (1995), Vol. 57, pages 299-310); (−)-epi gallocatechin-3-gallate (Lin & Lin, Mol. Pharmacol. (1997), Vol. 52, pages 465-472); deoxyspergualin (Tapper, et al., J Immunol. (1995), Vol. 155, pages 2427-36); Phenyl-N-tert-butylnitrone (Kotake, et al., Biochem. Biophys Acta (1998), Vol. 1446, pages 77-84; Quercutin (Sato, et al., J Rheumatol. (1997), Vol 24, pages 1680-84); Cucumin (Chan, Biochem, Pharmacol. (1998), Vol. 55, pages 965-973); or E3330 (Goto, et al., Mol. Pharmacol (1996), Vol. 49, pages 860-873).

As is clear from the examples of NF-κB inhibitors and activators indicated herein, it is preferred that the inhibitor or activator enters the cell and acts within the cell, ie acts as an intracellular NF-κB inhibitor or activator, for example an intracellular modulator of intracellular signalling events leading to NF-κB inhibition or activation.

In another embodiment of the invention, NF-κB may be inhibited by inhibitors of NF-κB, ie that act directly on the level (quantity), cellular location or activity of NF-κB. For example, the inhibitor may be a naturally occuring regulator of NF-κB that interacts directly with NF-κB, such as an IκB.

Preferably the inhibitor is an IκB, especially IκBA is described in, for example, paper by Makarov, Gene Therapy, 1997, Vol. 4, pages 846-852, and in PCT/GB98/02753. Other inhibitors of NF-κB include antisense cDNA or oligonucleotides encoding for any of the known NF-κB subunits, e.g. p50, p65, Rel B. Bondeson et al (1999) *Proc. Natl. Acad. Sci. USA* 96, 5668 describes an IκB-encoding adenovirus.

The inhibitor may also be a ribozyme which selectively destroy mRNA encoding NF-κB, or an antisense molecule which prevents transcription of NF-κB or an antibody or antibody—like molecule which blocks NF-κB action. These inhibitors are described in more detail below. It will be appreciated that inhibitors of APC, such as DC function, may also comprise ribozymes or antisense molecules or antibodies or antibody-like molecules which, for example, inhibit intracellular signalling within the APC.

It will be appreciated that inhibitors of inhibitors of NF-κB may act as inducers of NF-κB. Thus, antibodies or antisense molecules or ribozymes that block IκBα function or expression may act as inducers of NF-κB. The utility of such inducers is described below.

Ribozymes which may be encoded in the genomes of the viruses or virus-like particles herein disclosed are described in Cech and Herschlag "Site-specific cleavage of single stranded DNA" U.S. Pat. No. 5,180,818; Altman et al "Cleavage of targeted RNA by RNAse P" U.S. Pat. No. 5,168,053, Cantin et al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

Preferably the inhibitor is encoded by a nucleic acid sequence, for example within a vector, such as an adenovirus. The nucleic acid sequence encoding the inhibitor is preferably operatively linked to regulatory elements necessary for expression of said sequence. Such vectors may be used for gene therapy to enable the nucleic acid sequence encoding the inhibitor to be inserted into the body of a mammal. Methods of gene therapy, such as by using an adenovirus, are known in the art. The vector may also comprise a nucleic acid sequence encoding an antigenic molecule.

Preferably the vector construct used is AdvIκBα, disclosed in PCT/GB98/02753.

"Operatively linked" refers to juxtaposition such that the normal function of the components can be performed. Thus, a coding sequence "operatively linked" to regulatory elements refers to a configuration wherein the nucleic acid sequence encoding the inhibitor (or inducer, which is useful as described in more detail below), of NF-κB can be expressed under the control of the regulatory sequences.

"Regulatory sequences" refers to nucleic acid sequences necessary for the expression of an operatively linked coding sequence in a particular host organism. For example, the regulatory sequences which are suitable for eukaryotic cells are promotors, polyadenylation signals, and enhancers.

"Vectors" means a DNA molecule comprising a single strand, double strand, circular or supercoiled DNA. Suitable vectors include retroviruses, adenoviruses, adeno-associated viruses, pox viruses and bacterial plasmids. Retroviral vectors are retroviruses that replicate by randomly integrating their genome into that of the host. Suitable retroviral vectors are described in WO 92/07573.

Adenovirus is a linear double-standard DNA Virus. Suitable adenoviral vectors are described in Rosenfeld et al, Science, 1991, Vol. 252, page 432.

Adeno-associated viruses (AAV) belong to the parvo virus family and consist of a single strand DNA or about 4-6 KB.

Pox viral vectors are large viruses and have several sites in which genes can be inserted. They are thermostable and can be stored at room temperature. Safety studies indicate that pox viral vectors are replication-defective and cannot be transmitted from host to host or to the environment.

Vectors comprising nucleic acid encoding an NF-κB inhibitor (or inducer, as described below) may be introduced into a mammal in the form of liposomes in a manner known in the art. Alternatively, liposomes may be used in the form of aerosols in order to access the body by means of the mucus membrane or lung. Such techniques are known in the art.

Immunoliposomes (antibody-directed liposomes) are especially useful in targeting to cell types which over-express a cell surface protein for which antibodies are available, as is possible with dendritic cells or precursors, for example using antibodies to CD1, CD14 or CD83 (or other dendritic cell or precursor cell surface molecule, as indicated above). For the preparation of immuno-liposomes MPB-PE (N-[4-(p-male-imidophenyl)butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the DNA or other genetic construct of the invention for delivery to the target cells, for example, by forming the said liposomes in a solution of the DNA or other genetic construct, followed by sequential extrusion through polycarbonate membrane filters with 0.6 µm and 0.2 µm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immunoliposomes may be injected, for example intraperitoneally or directly into a site where the target cells are present, for example subcutaneously. Naked DNA encoding an inhibitor of NF-κB, in the form of a DNA vaccine, may also be used as an inhibitor of NF-κB.

As noted above, an alternative inhibitor is the use of antisense nucleic acid to an NF-κB sequence, for example Rel B. Such an anti-sense nucleic acid comprises a nucleic acid sequence which is capable of binding to an NF-κB nucleic acid sequence, inhibiting transcription of the NF-κB sequence. Methods of producing anti-sense nucleic acid per se are known in the art.

Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise a sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A)addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci.* (*USA*) 85(15), 5507-11). The Goodchild study showed that oligonucleotides that were most effective were complementary to the poly(A) signal; also effective were those targeted at the 5' end of the RNA, particularly the cap and 5' untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

Typically, antisense oligonucleotides are 15 to 35 bases in length. For example, 20-mer oligonucleotides have been shown to inhibit the expression of the epidermal growth factor receptor mRNA (Witters et al, *Breast Cancer Res Treat* 53:41-50 (1999)) and 25-mer oligonucleotides have been shown to decrease the expression of adrenocorticotropic hormone by greater than 90% (Frankel et al, *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

The anti-sense nucleic acid may be encoded by a suitable vector, for example of the type discussed above.

The inhibitor may alternatively be an anti-NF-κB vaccine or an antibody against NF-κB or fragment thereof such as an Fv. The vaccine or antibody may be against any suitable part of NF-κB providing it results in the inhibition of NF-κB. Preferably the antibody is a monoclonal antibody. Methods of producing vaccines and antibodies are known in the art. Alternatively, the antibody may be a suitable antibody fragment, such as an Fab or (Fab)$_2$ fragment or Fv, which still retains its anti-NF-κB activity. The antibody may be linked to polypeptide sequences that permit entry into cells, ie, the antibody (particularly antibody fragment) may be joined to a moiety that facilitates uptake of the antibody by a cell, for example a DC. For example, the antibody may be linked to a lipophilic molecule or polypeptide domain that is capable of promoting cellular uptake of the molecule or the interacting polypeptide, as known to those skilled in the art. Thus, the moiety may derivable from the Antennapedia helix 3 (Derossi et al (1998) *Trends Cell Biol* 8, 84-87), or from sequences of HIV, generally tat, that permit entry into cells. Such sequences are known and include the penetration peptide and the sequences of HIV generally engineered tat that permit entry into cells. Alternatively, the cDNA encoding such antibodies (preferably antibody fragments) could be delivered as a vector as described above.

A further aspect of the invention provides a method of stimulating antigen presentation or of stimulating an immune response in a mammal, such as a human, comprising administering a pharmaceutically effective amount of an intracellular inducer of APC, such as DC, function.

By "intracellular enhancer of APC function" we include any suitable enhancer of antigen presenting cell function. Typically, the enhancer is an enhancer of DC function. Preferably, the enhancer is an enhancer of intracellularly signalling within the APC.

The terms "APC function" and "intracellular signalling within the APC" are as defined above.

For the avoidance of doubt, cytokines and molecules containing a CPG motif are not intracellular inducers or enhancers of APC function since they act extracellularly.

A further aspect of the invention provides a method of stimulating antigen presentation or of stimulating an immune response in a mammal by administering a pharmaceutically-effective amount of an inducer of NF-κB. Preferably the method is used to treat (including prophylactically) infectious diseases or cancers by stimulating the immune system of the mammal. Infectious diseases include prion-related diseases, including spongiform encephalopathies. The method may be used to treat (including prophylachically) diseases or conditions characterised by aberrant types and/or aberrantly high levels of (harmful) molecules, for example polypeptides, in the body, for example levels of inflammatory mediators (for example cytokine) associated with chronic inflammation; breakdown products of cells or connective tissue matrix, for example fibronectin fragments; β-amyloid polypeptide (associated with Alzheimer's disease). Stimulating an immune response against such molecules may aid removal of the molecules from the body, thereby helping in resolution or prevention of the condition.

It is preferred if the cancer antigen is, or has at least one epitope present in, any of the following:
i) normal cellular proteins that are expressed at abnormally high levels in tumours; eg cyclin D1 in a variety of tumours; cyclin E in breast cancer; mdm 2 in a variety of tumours; EGF-R, erb-B2, erb-B3, FGF-R, insulin-like growth factor receptor, Met, myc, p53 and BCL-2 are all expressed in various tumours.
ii) normal cellular proteins that are mutated in tumours; eg Ras mutations in a variety of tumours; p53 mutations in a variety of tumours; BCR/ABL translocation in CML and ALL; CSF-1 receptor mutations in AML and MDS; APC mutations in colon cancer; RET mutations in MEN2A, 2B and FMTC; EGFR mutations in gliomas; PML/RARA translocation in PML; E2A-PBX1 translocation in pre B leukaemias and in childhood acute leukaemias.
iii) virally encoded proteins in tumours associated with viral infection; eg human papilloma virus proteins in cervical cancer; Epstein-Barr virus proteins in B cell lymphomas and Hodgkin's lymphoma; HTLV-1 proteins in adult T cell leukaemia; hepatitis B and C virus proteins in hepatocellular carcinoma; herpes-like virus proteins in Kaposi's sarcoma.
iv) HIV encoded proteins in HIV infected patients.

Thus, the above cancer-associated antigens can be divided into three main categories: (i) normal self antigens expressed at high levels in tumour cells; (ii) mutated self antigens expressed in tumour cells; (iii) viral antigens expressed in tumours associated with viral infection. Category (i) is preferred.

Three subtypes are included in category (i):
a) normal cellular proteins that are overexpressed;
b) proteins that are expressed in a tissue-specific fashion in normal cells but also in tumours; and
c) proteins that are embryonic antigens, silent in most adult tissues but aberrantly expressed in tumours.

Examples of b) and c) are:
b) tissue-specific differentiation antigens as targets for tumour-reactive CTL such as GATA-1, IKAROS, SCL (expressed in the haematopoietic lineage and in leukaemias); and
immunoglobulin constant regions (for treatment of multiple myeloma); and
c) Wilms-tumour antigen 1 (WT1) for treatment of leukaemias and Wilms tumour and carcinoembryonic antigens (CEA a foetal protein) for liver and intestinal tumours.

In one embodiment, the cancer—associated antigen may be provided by a crude extract of a tumour sample.

Overexpression of oncogene-encoded proteins in human tumours and mutated oncogenes expressed in human tumours are described in Stauss & Dahl (1995) *Tumour Immunology*, Dalgleish/Browning, Chapter 7, incorporated herein by reference.

Thus, it is preferred if the patient to be treated has cancer; more preferably any one of breast cancer; bladder cancer; lung cancer; prostate cancer; thyroid cancer, leukaemias and lymphomas such as CML, ALL, AML, PML; colon cancer; glioma; seminoma; liver cancer; pancreatic cancer; bladder cancer; renal cancer; cervical cancer; testicular cancer; head and neck cancer; ovarian cancer; neuroblastoma and melanoma.

CML is chronic myelocytic leukaemia; ALL is acute lymphoblastic leukaemia; AML is acute myelocytic leukaemia; and PML is promyelocytic leukaemia.

Alternatively, the patient have or be at risk of any disease caused by a pathogen, particularly a bacterium, yeast, virus, trypanosome and the like. It is preferred if the disease is caused by a chronic infection with a pathogen. It is also preferred if the pathogen is one which is not readily cleared by the host immune system.

It is preferred if the disease is a viral infection; more preferably a disease caused by any one of HIV, papilloma virus, Epstein-Barr virus, HTLV-1, hepatitis B virus, hepatitis C virus, herpes virus or any virus that causes chronic infection. It is particularly preferred if the virus is HIV.

Abnormally elevated amounts of a hormone produced by cells occur in some diseases such as certain types of thyroid disease. Thus, the method of the invention may be used to promote ablation of cells producing the elevated amounts of the hormone. The antigen may be the hormone the biosynthetic enzymes involved in synthesis of the hormone, which may be overproduced by the cell.

Patients with a bacterial infection, particularly an infection that causes chronic infection may also be usefully treated. The bacterial infection may be an intracellular infection. Thus, the method may be useful in treating tuberculosis.

The inventors have realised that the pivotal role of NF-κB allows it to be stimulated to produce an increase in the immune response within the mammal, for example human.

A further aspect of the invention provides an NF-κB inducer for use as a medicament, in particular as an immune response stimulant. The NF-κB inducer may be used as an anti-infectious disease agent or as an anti-cancer agent or in treating diseases or conditions characterised by aberrant types and/or aberrantly high levels of (harmful) molecules as discussed above.

Increasing the immune response in patients having an infectious disease or cancer or condition characterised by aberrant types and/or aberrantly high levels of molecules in the body will help to treat the patient by increasing the body's own immune response against the infectious disease or cancer or condition.

A further aspect of the invention provides an NF-κB inducer for use in the manufacture of a medicament to stimulate an immune response. Preferably the inducer is used to treat an infectious disease or a cancer or a condition as defined above.

Preferred NF-κB inducers include MEKKI, NIK, IKK1, IKK2, TRAF2, TRAF5, TRAF6, TAK, TPL-2 or Rel B or other NF-κB subunits e.g. p65 or cRel. Fragments and muteins of such inducers capable of inducing an NF-κB may also be used. The inducers may be encoded by suitable vectors, as described above for NF-κKB inhibitors, and introduced into the cells of a patient to be treated.

A preferred NF-κB inducer may be a dominant negative mutant of MyD88 (ie capable of inhibiting signalling by wild-type MyD88 molecules, for example in a cell in which wild-type and inhibitory MyD88 molecules are present). The inhibition may arise from blocking interaction of endogenous wild-type MyD88 with a binding partner of the endogenous MyD88, for example a Toll-Like Receptor (TLR). The dominant negative mutant may be MyD881pr (Burns et al (1998) *J Biol Chem* 273(20), 12203-12209) or a fragment of MyD88 lacking a death domain (see Burns et al (1998) and references reviewed therein). The MyD88 (myeloid differentiation protein) is considered to have a modular organisation consisting of an N-terminal death domain (DD) separated by a short linker from a C-terminal Toll domain (reviewed in Burns et al (1998)). The N-terminal DD is related to a motif of approximately 90 amino acids that is considered to mediate protein-protein interactions with other DD sequences forming either homo- or heterodimers (Boldin et al (1995) *J Biol Chem* 270, 387-391).

The inhibitory MyD88 molecule may be a MyD88 molecule that is less able than MyD88, preferably substantially unable, to bind to a DD, for example the DD of MyD88 or of IRAK. For example, the inhibitory MyD88 may be less able than MyD88, preferably substantially unable, to dimerise via the DD. The inhibitory MyD88 molecule may be a truncated version of MyD88, for example a MyD88 molecule in which all or part of the domain termed the Death Domain is deleted. It may be a mutated MyD88 molecule, for example a MyD88 molecule that is mutated in the DD, for example with a non-conservative mutation. For example, it may be mutated at the position equivalent to Phe56 of full length mouse MyD88, for example to Asn. It may be the mutated MyD88 molecule termed MyD881pr, as noted above in which the N terminal 53 amino acids of My D88 are also absent Burns et al (1998) *J. Biol. Chem.* 273, 12203-12209. MyD881pr has a point mutation (F56N; mouse sequence numbering) when compared with wild-type MyD88, for example mouse wild-type MyD88. This point mutation is in the DD and prevents dimerisation of the DD (Burns et al (1998)). The mutation corresponds to the 1pr$^{cp}$ mutation known to abolish cytotoxic signalling of Fas, probably by disrupting the conformation of the DD domain (Nagata (1994) *Semin Immunol* 6, 3-8; Huang et al (1996) *Nature* 384, 638-641).

The constructs for the wild-type MyD88 and dominant negative MyD88 (MyD88-1pr) has been published (Burns K. et al J. Biol Chem 1998) but MyD88-1pr is wrongly described as a single amino acid mutation in its death domain, where Phe$^{56}$ is mutated to Asn. This mutation corresponds to the 1pr$^{cp}$ mutation present in the death domain of Fas ligand which abolishes its downstream signalling by disrupting the conformation of the death domain. Actually, in addition to the point mutation there is a deletion in its N-terminal domain of 53 amino acids (1-159 base pairs of the genebank sequence are missing). This deletion results in part of the death domain missing.

It is preferred that the inhibitory MyD88 comprises a functional Toll domain, ie a Toll domain that is capable of interacting with a Toll domain, for example the Toll domain of a wild-type MyD88, for example wild-type human or mouse MyD88 or a TLR It is preferred that the inhibitory MyD88 comprises the full-length MyD88 Toll domain. A full-length Toll domain may be necessary for Toll-Toll domain interaction.

Methods of measuring protein-protein interactions (and their enhancement or disruption) will be well known to those skilled in the art. Suitable methods of measuring DD and Toll-Toll interactions are also described in Burns et al (1998).

Suitable methods may include, for example, yeast two-hybrid interactions, co-purification, ELISA, co-immunoprecipitations, fluorescence resonance energy transfer (FRET) techniques and surface plasmon resonance methods. Thus, a MyD88 molecule may be considered capable of binding to or interacting with a DD or Toll domain if an interaction may be detected between the said MyD88 polypeptide and a polypeptide comprising a DD or Toll domain by ELISA, co-immunoprecipitation or surface plasmon resonance methods or by a yeast two-hybrid interaction or copurification method. The preferred method is surface plasmon resonance.

Preliminary work indicates that MEKKI can induce NF-κB and enhance APC such as DC function. It is preferred that the inducer is capable of inducing NF-κB in DC or precursors thereof. Thus, inducers or enhancers of APC function may be useful in vaccine production. Similarly, inhibitors of APC function may be useful in preventing cells recognising a particular antigen and inducing an anergic state.

Thus, the invention provides a molecule comprising (1) a portion (modulating portion) comprising or encoding an intracellular modulator, for example an intracellular inhibitor or an intracellular enhancer of antigen-presenting cell (APC), such as DC, function and (2) a portion comprising or encoding an antigenic molecule (antigenic portion). In particular, the invention provides a polynucleotide encoding an antigen and a modulator, for example an inhibitor or an enhancer of DC function. Preferably, the molecule is or comprises a DNA vaccine encoding an antigen and an enhancer of APC, such as DC, function. The modulator, for example enhancer of APC, such as DC, function may be an intracellular signalling molecule or derivative thereof which retains or has enhanced intracellular signalling activity. It is preferred if the derivative is one which retains or enhances DC function. It is preferably an activator/inducer of NF-κB. It may be NF-κB or a component thereof The DNA vaccine may comprise a recombinant polynucleotide comprising a portion encoding the enhancer of APC, such as DC function and a portion encoding an antigenic molecule. Alternatively, the antigenic molecule may be encoded on a separate polynucleotide molecule; this is less preferred.

It will be appreciated that preferred inhibitors as described may be used.

Preferred enhancers are MEKK and a dominant negative mutant of My D88, for example My D881pr.

It will be appreciated that the preferred enhancers/inducers as described above may be used in the vaccines of the invention.

The antigenic molecule may comprise more than one copy of one or more epitopes. For example, it may comprise a single copy of a single epitope-forming amino acid sequence, for example a sequence of between about 8 and 30 amino acids, preferably about 10 to 18 amino acids, still more preferably about 15 amino acids in length. It may comprise multiple copies of such an epitope-forming sequence, or single or multiple copies of at least two different epitope-forming sequences. The antigenic sequences may be concatenated to form a domain-like structure, or may be disposed at different points in a carrier polypeptide. The polynucleotide may encode one or several different antigenic molecules, each of which may have one or more antigenic portions or epitopes.

The invention also includes DNA vaccines encoding an inducer of NF-κB for use in the invention. Such vaccines could include DNA sequences incorporating an antigen of interest derived from a pathogen, e.g. hepatitis A, B, C, etc, HIV, HTLV, influenza, tuberculoses, malaria or alternatively a cancer specific antigen or aberrant molecules such as β-amyloid, as discussed above, or a prion. In addition, such vaccines would also include an activator of NFκB, possibly two or more activators of NFκB for maximum effect. Both antigen and activator would be under the control of suitable promoter sequences to regulate expression of antigen and activators. An alternative method of stimulating an immune response may be to provide a vector comprising a nucleic acid sequence encoding an NF-κB inducer operatively linked to regulatory elements necessary for expressing said sequence. The vector may comprise an inducible promoter to enable an increased immune response to be produced by the increased activation of NF-κB.

The use of recombinant polyepitope vaccines for the delivery of multiple CD8 CTL epitopes is described in Thomson et al (1996) *J. Immunol.* 157, 822-826 and WO 96/03144, both of which are incorporated herein by reference. In relation to the present invention, it may be desirable to include in a single vaccine, a peptide (or a nucleic acid encoding a peptide) wherein the peptide includes, in any order, one or more antigenic amino acid sequences (for example each of between about 8 and 18 amino acids in length), for example derived from a tumour-associated antigen, and a CD4 T cell-stimulating epitope (such as from tetanus toxoid). Such "bead-on-a-string" vaccines are typically DNA vaccines.

The antigenic molecule may comprise an epitope present on transformed or cancerous cells (ie a tumour-associated antigen or epitope, for example the MAGE-1 antigen produced by a high proportion of human melanoma tymours (van der Bruggen et al (1991) *Science* 254, 1643)). Alternatively, it may comprise an epitope present on a pathogenic organism, for example a virus, or on a cell (preferably a human cell) infected by a pathogenic organism, for example a virally-infected cell, as noted above.

The epitope may be a T-cell epitope ie an epitope that is capable of inducing a T-cell response (TH-1 response), preferably a CD8+ cytotoxic T-cell response, but alternatively a CD4+ helper T-cell response (TH-2 response) as well known to those skilled in the art. A cytotoxic T-cell response may be undesirable in certain cases, for example when the antigen is a mycobacterial antigen (for example *Mycobacterium tuberculosis* or *M. leprae* antigen).

The inhibitor or inducer or antigen may be a peptidomimetic compound, for example a peptidomimetic compound corresponding to a polypeptide inhibitor or inducer discussed above.

The term "peptidomimetic" refers to a compound that mimics the conformation and desirable features of a particular peptide as a therapeutic agent, but that avoids potentially undesirable features. For example, morphine is a compound which can be orally administered, and which is a peptidomimetic of the peptide endorphin.

Therapeutic applications involving peptides may be limited, due to lack of oral bioavailability and to proteolytic degradation. Typically, for example, peptides are rapidly degraded in vivo by exo- and endopeptidases, resulting in generally very short biological half-lives. Another deficiency of peptides as potential therapeutic agents is their lack of bioavailability via oral administration. Degradation of the peptides by proteolytic enzymes in the gastrointestinal tract is likely to be an important contributing factor. The problem is, however, more complicated because it has been recognised that even small, cyclic peptides which are not subject to rapid metabolite inactivation nevertheless exhibit poor oral bioavailability. This is likely to be due to poor transport across the intestinal membrane and rapid clearance from the blood by hepatic extraction and subsequent excretion into the intestine. These observations suggest that multiple amide bonds may interfere with oral bioavailability. It is thought that the peptide bonds linking the amino acid residues in the peptide chain may break apart when the peptide drug is orally administered.

There are a number of different approaches to the design and synthesis of peptidomimetics. In one approach, such as disclosed by Sherman and Spatola, *J. Am. Chem. Soc.,* 112: 433 (1990), one or more amide bonds have been replaced in an essentially isoteric manner by a variety of chemical functional groups. This stepwise approach has met with some success in that active analogues have been obtained. In some instances, these analogues have been shown to possess longer biological half-lives than their naturally-occurring counterparts. Nevertheless, this approach has limitations. Successful replacement of more than one amide bond has been rare. Consequently, the resulting analogues have remained susceptible to enzymatic inactivation elsewhere in the molecule. When replacing the peptide bond it is preferred that the new linker moiety has substantially the same charge distribution and substantially the same planarity as a peptide bond.

Retro-inverso peptidomimetics, in which the peptide bonds are reversed, can be synthesised by methods known in the art, for example such as those described in Mézière et al (1997) *J. Immunol.* 159 3230-3237. This approach involves making pseudopeptides containing changes involving the backbone, and not the orientation of side chains. Retro-inverse peptides, which contain NH—CO bonds instead of CO—NH peptide bonds, are much more resistant to proteolysis.

In another approach, a variety of uncoded or modified amino acids such as D-amino acids and N-methyl amino acids have been used to modify mammalian peptides. Alternatively, a presumed bioactive conformation has been stabilised by a covalent modification, such as cyclisation or by incorporation of γ-lactam or other types of bridges. See, eg. Veber et al, *Proc. Natl. Acad. Sci. USA,* 75:2636 (1978) and Thursell et al, *Biochem. Biophys. Res. Comm.,* 111:166 (1983).

A common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

One approach to the synthesis of cyclic stabilised peptidomimetics is ring closing metathesis (RCM). This method involves steps of synthesising a peptide precursor and contacting it with a RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Polypeptides in which one or more of the amino acid residues are chemically modified, before or after the polypeptide is synthesised, may be used as antigen providing that the function of the polypeptide, namely the production of a specific immune response in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the polypeptide from in vivo metabolism.

A further aspect of the invention provides a kit of parts or composition of chimaeric molecule, comprising (1) an intracellular modulator, for example intracellular inhibitor or intracellular enhancer, of APC, such as DC, function and (2) and antigenic portion comprising or encoding an antigenic molecule.

A further aspect of the invention comprises a kit of parts, composition or a chimaeric molecule, for example chimaeric polypeptide, comprising a NF-κB inhibiting or activating/inducing portion and an antigenic portion, as defined above.

Either or both portions in these aspects of the invention may further comprise a translocating portion and/or a cell binding portion. The cell binding portion is preferably capable of binding to a dendritic cell or precursor thereof. The translocating portion may aid in internalisation of the molecule or at least the antigenic portion and preferably the signalling inhibiting or enhancing portion. Thus, exogenously applied peptides may be linked to a HIV tat peptide. This may direct them into the MHC Class I pathway for presentation by CTL (see, for example, Kim et al (1997) *J. Immunol.* 159, 1666-1668. Chimaeric molecules which may be adapted in accordance with the present invention are described in WO95/31483.

Dendritic cells may be characterised by expression of the CD80, CD86, CD40, CD1a, HLA-DR and/or CD83 cell surface molecules. Immature dendritic cells may be CD34+ or $CD14^+$. Thus, the cell binding portion may be capable of binding to one or more of these cell surface molecules (for example, an antibody capable of binding to such a molecule).

Immature DCs show increased antigen capture and processing. They show high intracellular MHC Class I and II' increased endocytosis and phagocytosis; high CCR1, CCR5 and CCR6; low CCR7; high CD68; low CD40, CD54, CD80, CD83, and CD86; and no DC-LAMP.

Mature DCs show increased antigen processing. They show high surface MHC Class I and II; low endocytosis and phagocytosis; low CCR1, CCR5 and CCR6; high CCR7; low CD68; high CD40, CD54, CD58, CD80, CD83 and CD86; high DC-LAMP; and high p55 fascin.

Such a cell binding portion may be useful in directing any inhibitor or activator as herein described, for example nucleic acid, DNA vaccine or antibody, to an APC such as a DC or immature DC.

Preferably, the polynucleotide or DNA vaccine is capable of expressing the encoded antisense molecule or polypeptide(s) in the patient, still more preferably in an APC such as a DC or immature DC of the patient. The antisense molecule or polypeptide(s), for example NF-κB inhibitor or inducer/activator, or antigen, as appropriate, may be expressed from any suitable polynucleotide (genetic construct) as is described herein and delivered to the patient. Typically, the genetic construct which expresses the antisense molecule or polypeptide comprises the said polypeptide coding sequence operatively linked to a promoter which can express the transcribed polynucleotide (eg mRNA) molecule in a cell of the patient, which may be translated to synthesise the said polypeptide. Suitable promoters will be known to those skilled in the art, and may include promoters for ubiquitously expressed, for example housekeeping genes or for tissue-specific genes, depending upon where it is desired to express the said polypeptide (for example, in dendritic cells or precursors thereof). Preferably, a dendritic cell or dendritic precursor cell-selective promoter is used, but this is not essential, particularly if delivery or uptake of the polynucleotide is targeted to the selected cells ie dendritic cells or precursors.

Promoters that may be selective for dendritic cells may be promoters from the CD36 or CD83 genes.

Targeting the vaccine to specific cell populations, for example antigen presenting cells, may be achieved, for example, either by the site of injection, use of targeting vectors and delivery systems, or selective purification of such a cell population from the patient and ex vivo administration of the peptide or nucleic acid (for example dendritic cells may be sorted as described in Zhou et al (1995) *Blood* 86, 3295-3301; Roth et al (1996) *Scand. J. Immunology* 43, 646-651). In addition, targeting vectors may comprise a tissue- or tumourspecific promoter which directs expression of the antigen at a suitable place.

As noted above, it may be desirable to use an inducible promoter. It will be appreciated that it may be desirable to be able to regulate temporally expression of the polypeptide(s) (for example NF-κB inhibitor or activator/inducer) in the cell. Thus, it may be desirable that expression of the polypeptide(s) is directly or indirectly (see below) under the control of a promoter that may be regulated, for example by the concentration of a small molecule that may be administered to the patient when it is desired to activate or repress (depending upon whether the small molecule effects activation or repression of the said promoter) expression of the polypeptide. It will be appreciated that this may be of particular benefit if the expression construct is stable ie capable of expressing the polypeptide (in the presence of any necessary regulatory molecules) in the said cell for a period of at least one week, one, two, three, four, five, six, eight months or more. A preferred construct of the invention may comprise a iregulatable promoter. Examples of regulatable promoters include those referred to in the following papers: Rivera et al (1999) *Proc Natl Acad Sci USA* 96(15), 8657-62 (control by rapamycin, an orally bioavailable drug, using two separate adenovirus or adeno-associated virus (AAV) vectors, one encoding an inducible human growth hormone (hGH) target gene, and the other a bipartite rapamycin-regulated transcription factor); Magari et al (1997) *J Clin Invest* 100(11), 2865-72 (control by rapamycin); Bueler (1999) *Biol Chem* 380(6), 613-22 (review of adeno-associated viral vectors); Bohl et al (1998) *Blood* 92(5), 1512-7 (control by doxycycline in adeno-associated vector); Abruzzese et al (1996) *J Mol Med* 74(7), 379-92 (reviews induction factors e.g., hormones, growth factors, cytokines, cytostatics, irradiation, heat shock and associated responsive elements). Tetracycline—inducible vectors may also be used. These are activated by a relatively—non toxic antibiotic that has been shown to be useful for regulating expression in mammalian cell cultures. Also, steroid-based inducers may be useful especially since the steroid receptor complex enters the nucleus where the DNA vector must be segregated prior to transcription.

This system may be further improved by regulating the expression at two levels, for example by using a tissue-specific promoter and a promoter controlled by an exogenous inducer/repressor, for example a small molecule inducer, as discussed above and known to those skilled in the art. Thus, one level of regulation may involve linking the appropriate polypeptide-encoding gene to an inducible promoter whilst a further level of regulation entails using a tissue-specific promoter to drive the gene encoding the requisite inducible transcription factor (which controls expression of the polypeptide (for example NF-κB inhibitor or inducer/activator-encoding gene) from the inducible promoter. Control may further be improved by cell-type-specific targeting of the genetic construct.

The methods or constructs of the invention may be evaluated in, for example, APCs such as dendritic cells generated in vitro, as known to those skilled in the art, before evaluation in whole animals. Suitable methods are described in Example 1.

The genetic constructs of the invention can be prepared using methods well known in the art.

A further aspect of the invention provides vectors, vaccines and antibodies for use in the invention.

The vaccines and vectors of the invention (therapeutic molecules of the invention) may be formulated with suitable pharmaceutically-acceptable carriers, fillers or other additives. They may be administered by any suitable means such as intra-muscularly, intra-veinally, orally, anally, intra-nasally, etc. Subcutaneous or intramuscular administration may be preferred. It will be appreciated that an inducer, for example small molecule inducer as discussed above may preferably be administered orally.

It may be desirable to locally perfuse an area comprising target cells with the suitable delivery vehicle comprising the therapeutic molecule, for example genetic construct, for a period of time; additionally or alternatively the delivery vehicle or therapeutic molecule can be injected directly into accessible areas comprising target cells, for example subcutaneously. Methods of delivering genetic constructs, for example adenoviral vector constructs to cells of a patient will be well known to those skilled in the art.

In particular, an adoptive therapy protocol may be used or a gene gun may be used to deliver the construct to dendritic cells, for example in the skin.

An adoptive therapy approach may include the steps of (1) obtaining antigen presenting cells or precursors thereof, preferably dendritic cells or precursors thereof, from the patient; (2) contacting said antigen presenting cells with a NF-κB inhibitor or inducer/activator as described herein, and optionally antigen to which an immune response is required, or chimaeric molecule or polynucleotide as discussed above, ex vivo; and (3) reintroducing the so treated antigen presenting cells into the patient.

Suitably, the dendritic cells are autologous dendritic cells which are pulsed with polypeptide(s), for example a NF-κB activator and an antigen. T-cell therapy using autologous dendritic cells pulsed with peptides from a tumour associated antigen is disclosed in Murphy et al (1996) *The Prostate* 29, 371-380 and Tjua et al (1997) *The Prostate* 32, 272-278.

In a further embodiment the antigen presenting cells, such as dendritic cells, are contacted with a polynucleotide which encodes the NF-κB inhibitor or activator/inducer. The polynucleotide may be any suitable polynucleotide and it is preferred that it is capable of transducing the dendritic cell thus resulting in respectively activation or inhibition of antigen presentation by the antigen presenting cell.

Conveniently, the polynucleotide may be comprised in a viral polynucleotide or virus, as noted above. For example, adenovirus-transduced dendritic cells have been shown to induce antigen-specific antitumour immunity in relation to MUC1 (see Gong et al (1997) *Gene Ther.* 4, 1023-1028). Similarly, adenovirus-based systems may be used (see, for example, Wan et al (1997) *Hum. Gene Ther.* 8, 1355-1363); retroviral systems may be used (Specht et al (1997) *J. Exp. Med.* 186, 1213-1221 and Szabolcs et al (1997) *Blood* 90, 2160-2167); particle-mediated transfer to dendritic cells may also be used (Tuting et al (1997) *Eur. J. Immunol.* 27, 2702-2707); and RNA may also be used (Ashley et al (1997) *J. Exp. Med.* 186, 1177-1182).

The APCs, such as dendritic cells, may be derived from the patient (ie autologous dendritic cells) or from a healthy individual or individuals (MHC matched or mismatched), treated in vitro as indicated above, followed by adoptive therapy, ie introduction of the so-manipulated dendritic cells in vivo, which may then activate CTL responses. By "healthy individual" we mean that the individual is generally in good health, preferably has a competent immune system and, more preferably, is not suffering from any disease which can be readily tested for, and detected.

Thus, the methods of the invention include methods of adoptive immunotherapy.

It is preferred if between about $10^3$ and $10^{11}$ DCs are administered to the patient; more preferably between $10^6$ and $10^7$ DCs.

The APCs such as DCs may be administered by any convenient route. It is preferred if the DCs are administered intravenously. It is also preferred if the DCs are administered locally to the site of the disease (such as a tumour or local viral or bacterial infection). Local administration is particularly preferred for cancer. Conveniently, the DCs are administered into an artery that supplies the site of the disease or the tissue where the disease is located.

The cells (or vaccine) may be given to a patient who is being treated for the disease by some other method. Thus, although the method of treatment may be used alone it is desirable to use it as an adjuvant therapy.

The APCs, such as DCs, or vaccine may be administered before, during or after the other therapy.

When the disease to be treated is a cancer it is preferable if the cancer has been, is being or will be treated with a conventional therapy or surgery as well as with the method of the invention. Conveniently, depending on the therapy, the cancer is treated by radiotherapy or by chemotherapy.

When the disease to be treated is an infection by a pathogen it is preferable if the infection has been, is being or will be treated with a conventional therapy or surgery.

If the patient to be treated has HIV infection it is preferable if the method of the invention is used as an adjuvant to other treatment, for example treatment with a reverse transcriptase inhibitor such as AZT or 3TC or combination therapy for example HART (highly active retroviral therapy).

When the method of the invention is used to treat a solid tumour it is preferred if the APCs such as DCs or vaccine are administered as the first post-surgery treatment.

When the method of the invention is used to treat leukaemia it is preferred if the APCs such as DCs or vaccine are administered after radiotherapy or chemotherapy. It is also preferred if leukaemia patients are also treated with the DCs in combination with bone marrow transplantation.

Cancer therapy, for example adoptive immunotherapy may be most effective in the control or elimination of minimal residual disease rather than in the reduction of bulk disease. It is conceivable that immunotherapy may temporarily increase the dimensions of bulk disease due to influx of cytotoxic T lymphocytes. Extent and bulk of disease may be monitored following therapy but not used as a formal endpoint. Patients are followed up in the routine manner in the long term to ensure that no long term adverse events are manifest.

Further delivery or targeting strategies may include the following. Ballistic compressed air driven DNA/protein coated nanoparticle penetration (for example using a BioRad device) of cells in culture or in vivo may be used Constructs for delivery should preferably have cell-type specific promoters.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind well known to those skilled in the art. Nasal sprays may be a useful format.

The dose of the construct, for example, is dependent on the size of the construct and the purpose for which is it administered. In general, the range is calculated based on the surface area of tissue to be treated. The effective dose of construct may be dependent on the size of the construct and the delivery vehicle/targeting method used and chemical composition of the oligonucleotide but a suitable dose may be determined by the skilled person, for example making use of data from the animal and in vitro test systems indicated above.

The construct, for example, may be administered to the patient systemically for both therapeutic and prophylactic purposes. The construct, for example may be administered by any effective method, as described above, for example, parenterally (eg intravenously, subcutaneously, intramuscularly) or by oral, nasal or other means which permit the construct, for example, to access and circulate in the patient's bloodstream. Construct administered systemically preferably are given in addition to locally administered construct, but also have utility in the absence of local administration.

It is believed that uptake of the nucleic acid and expression of the encoded polypeptide by dendritic cells may be the mechanism of priming of the immune response; however, dendritic cells may not be transfected but are still important since they may pick up expressed peptide from transfected cells in the tissue.

It is preferred if the vaccine, such as DNA vaccine, is administered into the muscle. It is also preferred if the vaccine is administered onto or into the skin.

As noted above, the invention provides a kit of parts or composition or a chimaeric molecule, comprising (1) a modulating portion comprising or encoding a NF-κB inhibitor or inducer and (2) an antigenic portion comprising or encoding an antigenic molecule.

In relation to any previous aspect of the invention, particularly a vaccine as previously described, or such a kit, chimaeric molecule or composition, the antigenic molecule preferably comprises an epitope present on transformed or cancerous cells or on a pathogenic organism, or on a cell infected by a pathogenic organism.

Thus, the invention provides a vaccine effective against cancer, or cancer or tumour cells, or against a pathogenic organism or cell infected with a pathogenic organism, comprising an effective amount of an NF-κB inducer or other inducer of APC function as described above or polynucleotide encoding an NF-κB inducer or other inducer of APC function. The vaccine preferably further comprising an antigen or polynucleotide encoding an antigen, having an epitope present on the cancer or tumour cells, or the pathogenic organism or cell infected with a pathogenic organism. The vaccine is preferably a nucleic acid vaccine.

A further aspect of the invention provides a pharmaceutical composition comprising a NF-κB inducer, NF-κB inhibitor, vaccine, molecule, polynucleotide, kit of parts, composition or chimaeric molecule of any of the preceding aspects of the invention and a pharmaceutically acceptable carrier.

The invention further provides a vaccine, molecule, polynucleotide, kit of parts, composition or chimaeric molecule of any preceding aspect of the invention for use in medicine. The invention still further provides the use of a vaccine, molecule, polynucleotide, kit of parts, composition or chimaeric molecule of any of the preceding aspects of the invention in the manufacture of a medicament for the treatment of a patient in need of modulation of antigen presentation.

It will be clear that the invention provides a method of killing target cells in a patient which target cells aberrantly express a first epitope, the method comprising the steps of (1) obtaining APCs, such as dendritic cells, from said patient; (2) contacting said APCs, such as dendritic cells, with an enhancer of APC, such as DC, function ex vivo; (3) optionally contacting said cells with the said epitope or with a polynucleotide or expression vector encoding the said epitope and (4) reintroducing the so treated APCs such as dendritic cells, into the patient.

It will also be clear that the invention provides a method of killing target cells in a patient which target cells aberrantly express a first epitope, the method comprising the steps of (1) obtaining dendritic cells from said patient; (2) contacting said dendritic cells with a NF-κB inducer ex vivo; (3) optionally contacting said cells with the said epitope or with a polynucleotide or expression vector encoding the said epitope and (4) reintroducing the so treated dendritic cells into the patient.

The target cells may be cancer cells.

The invention also provides methods of inhibiting or stimulating the maturation and activation of dendritic cells in vivo or in vitro comprising administering an effective amount of an inhibitor or inducer of NF-κB.

The inhibitors or inducers may be as defined above.

For the avoidance of doubt, wherever the term "dendritic cell" or "dendritic cells" are used the term includes any suitable antigen presenting cell unless the context suggests otherwise. It is preferred that the antigen presenting cell is a dendritic cell.

Preferred embodiments of the invention will now be described.

DESCRIPTION OF THE DRAWINGS

Figures Legends

FIG. 1. Cell viability of DC treated with PSI. Mature DC was either left untreated, or treated with various doses of PSI for 4 h. After wash, cells were cultured in RPMI 1640 supplemented as described without monocyte condition medium. 6 days after treatment, cells were resuspended in PBS containing 10 μg/ml. Of propidium iodide PI and analysed on FACS scan.

FIG. 7. Reduced expression of surface antigens on allo-lymphocytes by PSI pre-treated DC. Lymphocytes were cultured for 6 days as the same conditions with allo-MLR experiment using vehicle treated DC (green line), or PSI (1 μM) treated DC (red line). Each lymphocytes were phenotyped with MoAbs, CD3, CD25 (PE conjugated; Pharmingen), (CD54) (PE conjugated; Serotec), CD50 (FITC conjugated; Serotec) and analysed by FACScan.

FIG. 8. Cytokine production of allo-lymphocytes co-cultured with vehicle treated or PSI treated DC. Mature DC was treated with vehicle or PSI (1 μM) as described above. Allo-lymphocytes and each DC were plated at 2×$10^5$ cells per well on a 96 well plate and stimulated with PMA (10 nM) or left unstimulated for 49 hr. Supernatants were analysed for IL-2, IL-4, and interferon-γ by ELISA.

FIG. 9. Cytokine productions of DC treated with vehicle or PSI. Mature DC was treated with vehicle or PSI (1 μM) as described above. Each DC and allo-lymphocytes were plated at 2×$10^5$ cells per well on a 96 well plate and stimulated with PMA (10 nM) or left unstimulated for 48 hr. Supernatants were analysed for IL-6, IL-8, IL-12 and TNFα by ELISA.

Immature DC were generated from peripheral blood monocytes after 5 days of culture with 50 ng/ml GM-CSF and 10 ng/ml IL-4. Then, they were left uninfected, or infected in serum-free medium with a control adenovirus without insert (Ad0), and an adenovirus encoding the dominant negative form of MyD88 (Adlpr). After 48 h, graded doses of dendritic cells were cultured with 1×10⁵ allogeneic T cells and proliferation was measured at day 6. expression of dominant negative MyD88 enhances the allogeneic T cell proliferation, a finding that is indicative of increased DC antigen presentation.

Figure 16:
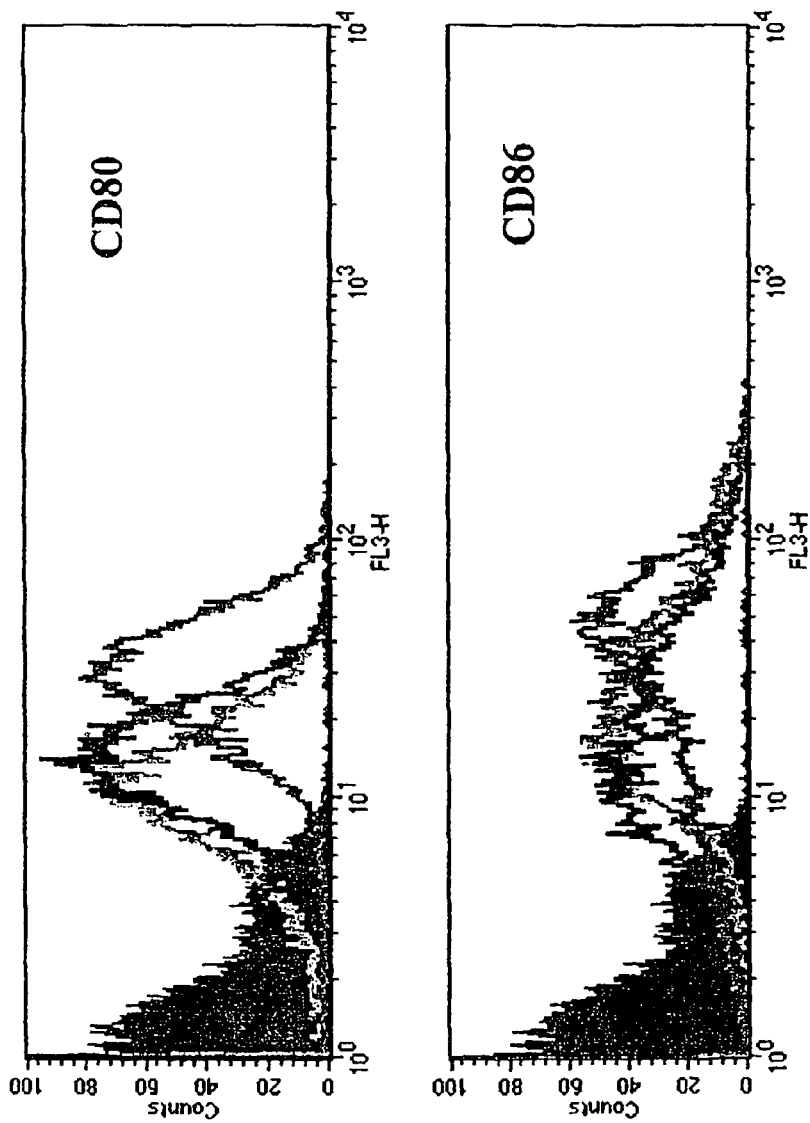

FIG. 16: Expression of dominant-negative MyD88 in dendritic cells enhances the expression of costimulatory molecules (CD80, CD86) Immature DC were generated from peripheral blood monocytes after 5 days of culture with 50 ng/ml GM-CSF and 10 ng/ml IL-4. Then, they were left uninfected, or infected in serum-free medium with a control adenovirus encoding GFP, and with an adenovirus encoding dominant negative MyD88 (Adlpr). After 48 h, dendritic cells were collected and stained for CD80 and CD86, two very important costimulatory molecules required for efficient antigen-presenting function. expression of the dominant negative form of MyD88 enhanced CD80 and CD86 cell surface expression, which is indicative of enhanced dendritic cell antigen-presenting function.

Figure 17:
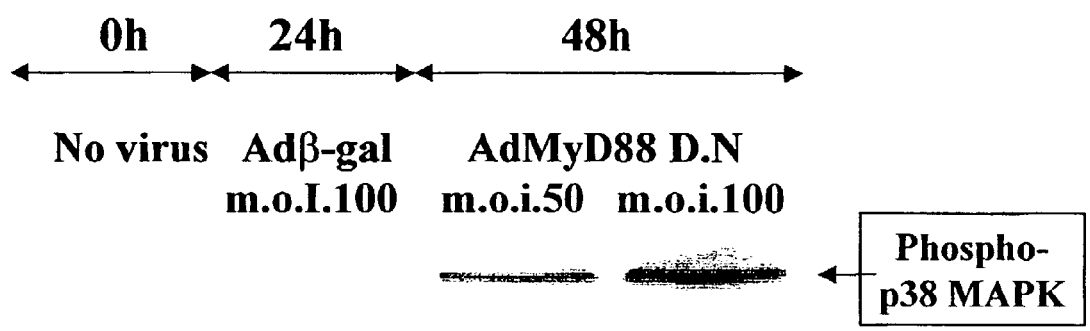

FIG. 17: Expression of dominant-negative MyD88 in macrophages induces p38 MAPK phosphorylation Human macrophages were differentiated from peripheral blood monocytes by addition of 100 ng/ml M-CSF for 2-3 days in 5% FCS RPMI. Then, they were left uninfected, infected in serum-free medium with a control adenovirus encoding β-gal, or infected with an adenovirus encoding dominant negative MyD88 (Adlpr). An moi of 100 (or 50 in one case) was used as shown. After 6, 24 and 48 h, cells were lysed and extracts assayed for p38 MAPK activity using western blotting and phospho-p38 MAPK-specific antibodies. Unexpectedly, expression of dominant-negative MyD88 induces p38 MAPK activity in human macrophages.

FIG. 18: Expression of dominant-negative MyD88 in macrophages induces IRAK phosphorylation Human macrophages were differentiated from peripheral blood monocytes by addition of 100 ng/ml M-CSF for 2-3 days in 5% FCS RPMI. HELA cells cultured in 5% FCS DMEM were also used Both cell types were left uninfected, infected in serum-free medium with a control adenovirus encoding β-gal, an adenovirus encoding wild-type MyD88 or an adenovirus encoding dominant negative MyD88 (AdMyD88lpr). An moi of 100 was used. After 5 min or 12 h, cells were lysed and extracts assayed for IRAK and phospho-IRAK using western blotting. In HELA cells, expression of dominant negative MyD88 (MyD88-1pr) was found to inhibit IL-1-induced activation of IRAK. Unexpectedly, however, expression of dominant-negative MyD88 induces IRAK activity in human macrophages that is not increased by the addition of LPS. This finding suggests that MyD88 activity is also required for an inhibitory signal in macrophages (but not HELA cells) that inhibits IRAK phosphorylation, and its blockade results in the activation of IRAK.

Figure 19:
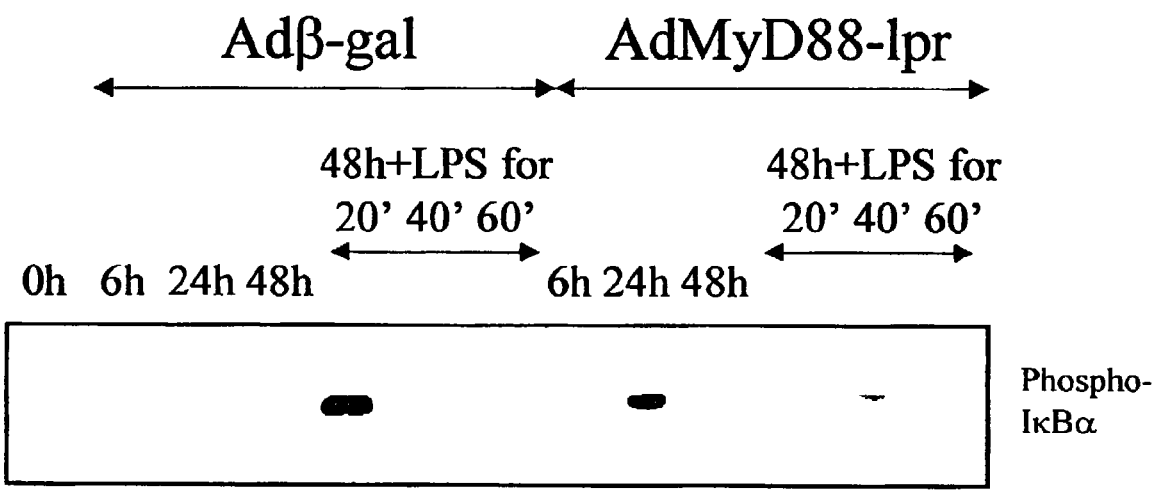

FIG. 19: Expression of dominant-negative MyD88 in macrophages induces IκBα phosphorylation Human macrophages were differentiated from peripheral blood monocytes by addition of 100 ng/ml M-CSF for 2-3 days in 5% FCS RPMI. Cells infected in serum-free medium with a control adenovirus encoding β-gal or an adenovirus encoding dominant negative MyD88 (Adlpr). An moi of 100 was used. After 24 h, cells were lysed and extracts assayed for phospho-IκBα using western blotting. Unexpectedly, expression of dominant-negative MyD88 induces IκBα phosphorylation in human macrophages.

FIG. 20: Expression of dominant-negative but not wild-type MyD88 in macrophages induces TNFα, IL-6 and IL-8 production in the absence of any stimulus.

Human macrophages were differentiated from peripheral blood monocytes by addition of 100 ng/ml M-CSF for 2-3 days in 5% FCS RPMI. Then, they were left uninfected, infected in serum-free medium with a control adenovirus encoding β-gal, infected with an adenovirus encoding wild-type MyD88 or infected with an adenovirus encoding dominant negative MyD88 (Adlpr). An moi of 100 was used. (a) After 48 h, supernatants were collected and assayed for TNFα, IL-6 and IL-8 cytokine production in the absence of any further stimulation. Cytokine production could be detected in cells encoding dominant negative MyD88 but not cells encoding wild-type MyD88 or control cells. This suggested that blocking MyD88 activity in macrophages, as in dendritic cells but not HSF or HUVEC, results in the activation of cells and the release of inflammatory cytokines. (b) At 0 h, 4 h, 24 h and 48 h of expression, supurnatants were collected and assayed by ELISA for TNF, IL-6 and IL-8. Only the results from cells encoding dominant negative MyD88 (MyD88-1pr) are shown as control cells or cells encoding wild-type MyD88 had background levels of cytokine production.

Materials and Methods

1. Reagents

Human recombinant GM-CSF and TNFα were kind gifts of Dr Glenn Larsen (GI) and Dr D Tracey (BASF), respectively. Human recombinant IL-4 was purchased from R&D Systems (Minneapolis, USA). PMA, LPS and Ionomycin were obtained from Sigma Chemical Co. (St Louis, USA). The proteasome inhibitor Cbz-Ile-Glu(O-terr-butyl-Ala-ceremal (PSI) was The proteasome inhibitor Cbz-Ile-Glu(O-terr-butyl-Ala-ceremal (PSI) was obtained from Calbiochem (Nottingham, UK). M-CSF was obtained from the Genetics Institute (Boston, USA).

2. Preparation of Peripheral Blood Mononuclear Cells

Peripheral blood mononuclear cells (PBMC) were obtained by density centrifugation of leukopheresis residues from healthy volunteers (North London Blood Transfusion Service, Colindale, UK). Heparinised residues were diluted 2× with HBSS and 25 ml were carefully layered over equal volumes of Ficoll-Hypaque lymphoprep (Nycomed, Oslo, Norway) in 50 ml sterile tubes prior to centrifugation for 30 minutes at 2000 rpm at room temperature. After centrifugation, the interface layer was collected and washed twice with HBSS (centrifuged for 10 minutes at 2000 rpm). PBMC were then collected and resuspended in 30 ml of RPMI containing 5% FCS.

3. Isolation of Peripheral Blood T Cells and Monocytes and Culture of HeLa Cells Peripheral blood T cells and monocytes were obtained from PBMC after cell cell separation in a Beckman JE6 elutriator. Elutriation was performed in RPMI containing 1% FCS (elutriation medium). Lymphocyte and monocyte purity was assessed by flow cytometry using fluorochrome-conjugated anti-human monoclonal antibodies against CD45, CD3, CD14 and CD19 (Becton Dickinson, Oxford, UK). T lymphocyte fractions typically contained ~80% CD3-expressing cells, ~6% CD19-expressing cells and <1% CD14-expressing cells. Monocyte fractions routinely consisted of >85% CD14-expressing cells, <0.5% CD19 cells and <3% of CD3-expressing cells. HeLa cells were maintained in 5% FCS, 1% penicillin/streptomycin DMEM.

4. Differentiation of Monocytes with M-CSF for Adenoviral Infection

To optimize adenoviral infection, freshly elutriated monocytes were cultured at 1×10⁶ cells/ml in 10 cm petri dishes (Falcon, UK) with 100 ng/ml of M-CSF (Genetics Institute, Boston, USA). After 2-3 days they were washed with PBS to remove non-adherent cells and the remaining adherent monocytes were incubated with 10 ml of cell dissociation solution (Sigma, UK) for 1 h at 37° C. The cell suspension was washed twice in RPMI containing 5% FCS and cell viability (90%) was assessed by trypan blue exclusion. Cells at this stage were 99% CD14 positive by FACS staining and were cultured at $1 \times 10^6$/ml, in 24-well or 48-well flat-bottomed tissue culture plates (Falcon, UK) for further experiments.

5. Differentiation of Monocytes to Dendritic Cells

Freshly elutriated monocytes were cultured at $1 \times 10^6$ cells/ml in 10 cm petri dishes (Falcon, UK) in 5% FCS RPMI supplemented with 50 ng/ml GM-CSF and 10 ng/ml IL-4 for 5-6 days. At day 3, cytokines were replenished. This method presents several advantages as compared to differentiation of dendritic cells directly from blood or bone marrow precursors. Besides being easy and giving high numbers of cells, it generates a homogenous population of cells with a stable "immature DC" phenotype. This phenotype can be pushed to maturation by addition of TNFα (10 ng/ml), LPS (100 ng/ml) or monocyte-conditioned medium (50% v/v) for a further 2-3 days to the DC.

6. Monocyte Conditioned Medium

Ig-coated plates (100 mm, Falcon) were prepared immediately before use by the addition of 5 ml of human gamma-globulin (10 mg/ml, Sigma Chemical Co.) for 10 min. The plates were washed three times with RPMI 1640 medium (serum free) before use. Elutriated monocytes ($3 \times 10^7$) were layered on the Ig-coated plates for 1 hr in 7 ml volumes. Non-adherent cells were washed off, and gamma-globulin adhered cells were incubated in fresh complete RPMI 1640 medium at 37° C. for 24 hr.

7. Adenoviral Vectors and their Propagation

Recombinant, replication-deficient adenoviral vectors encoding E. coli β-galactosidase (Adβ-gal) or having no insert (Ad0) were provided by Drs A. Byrnes and M. Wood (Oxford University, UK). The GFP-expressing adenovirus (AdGFP) was generated by double recombination of AdTrack with AdEasy-1 adenoviral plasmid provided by Prof. B. Vogelstein (The Howard Huges Medical Institute, Baltimore, Md.). AdMyD88wt and AdMyD881pr were generated from plasmids provided by Dr Xu (University of Texas, Southwestern) and Dr K. Burns (Lausanne, Switzerland). In particular, pAdTrackCMV was used for AdMEKK-1wt, whereas for AdMyD88wt and AdMyD881pr, a pAdTrack.CMV vector derivative, termed AdTrack.CMVKS17, was used. pAdTrack.CMVKS17 was constructed by removing the EcoRI site of AdTrack.CMV as well as its multiple cloning site (MCS), and by inserting the larger multiple cloning site of the vector pBCSK(+) (Stratagene). Recombinant viruses were generated in BJ5183 bacterial cells transformed by the heat-shock method with 1 µg of linearised pAdTrack.CMV-MEKK1wt, AdTrack.CMVKS17-MyD88wt or AdTrack.CMVKS17-My881pr constructs and 100 ng of replication-deficient adenoviral vector pAdEasy-1. Positive recombinant clones were selected through their resistance to kanamycin. Following selection, DNA extracted was used for virus propagation in the 293 human embryonic kidney cells. Viruses were purified by ultracentrifugation through two caesium chloride gradients, as described in He et al. (He T. C. et al. (1998). Science 281: 1509-12). Titres of viral stocks were determined by plaque assay, in HEK 293 cells, after exposure for 1 hour in serum free DMEM medium (Gibco BRL) and subsequently overlayed with an (1.5%) agarose/($2 \times$DMEM with 4% FCS) mixture (v/v 1:1) and incubated for 10-14 days. (He T. C. et al. (1998). Science 281: 1509-12).

9. Adenoviral Infection of Cells

M-CSF-differentiated macrophages and immature or mature dendritic cells were collected, counted and replated. Then, they were infected in serum-free RPMI with replication-deficient adenoviruses overexpressing the gene of interest. A multiplicity of infection of 100 for macrophages and immature DC, and 300, for mature DC, was used. After 2 h, the virus was removed and cells were cultured in complete medium for an additional 1-2 days to allow overexpression of the protein of interest. Then, they were used in further experiments.

10. Establishment of Antigen-Specific T Cell Lines

Green fluorescent protein was purchased from Clontech. To establish antigen-specific polyclonal T cell lines, $1 \times 10^6$ PBMC/ml were cultured with antigen (1 µg/ml for green fluorescent protein or 5 µg/ml for tetanus toxoid) for 7 days and then with IL-2 at 20 ng/ml for another 10-14 days. Every 4 days IL-2 was replenished. This resulted in the expansion of antigen-specific T cells and cell death of most other cell populations present in PBMC. After 17-21 days of culture, a restimulation step was included by culturing the T cells with autologous irradiated PBMC at a 1:1 ratio and fresh antigen in the absence of IL-2. After 4 days IL-2 was added for another 10-14 days. This restimulation cycle was repeated at least 4 times before use of antigen-specific T cells in further experiments.

11. Proliferation Assays of Antigen-Specific T Cells

To assess the specificity of antigen-specific T cell lines, $1 \times 10^5$ of antigen-specific T cells were cultured with $1 \times 10^5$ autologous irradiated PBMC and various concentrations of antigen in 96-well flat-bottomed microtiter plates. After 3 days, cells were pulsed with [$^3$H]Thymidine overnight and harvested the following day.

To measure dendritic cell-induced antigen-specific T cell proliferation, $1 \times 10^5$ antigen-specific T cells were cultured with graded doses of irradiated or mitomycin-treated dendritic cells that were unpulsed, pulsed with antigen, uninfected or adenovirus-infected. [$^3$H]-Thymidine incorporation was measured after 2 days. All antigen-specific proliferation assays were done in triplicates.

12. Mixed Lymphocyte Reaction (MLR)

To assay the immunostimulatory capacity of non-irradiated or irradiated (3000 rad from a $^{137}$Cs source) DC, uninfected, adenovirus-infected, LPS-treated or monocyte-conditioned medium-treated DC were cultured in graded doses with $1 \times 10^5$ of allogeneic elutriated T cells in quadruplicate in a 96-well flat-bottom microtiter plate (Falcon). Proliferation was measured on day 5 by thymidine incorporation after a 16 h pulse with [$^3$H] thymidine (0.5 µCi/well; Amersham Life Science, UK).

13. Cytokine Analysis

Cells were pre-treated with vehicle or 1 µM of PSI for 4 h, or infected with adenoviral vectors for 2 h. PSI-treated DC were then directly used in experiments whereas infected cells were further cultured for 2 days to allow overexpression of the relevant protein to occur. 24 h after stimulation of the cells, culture supernatants were collected and kept frozen. Cytokine levels in cell culture supernatants were measured by standard 2 or 3 layer sandwich ELISA techniques using specific monoclonal and polyclonal antibodies for TNFα, IL-4, IL-6, IL-8, IL-12 and IFNγ. Antibody pairs and standards for these assays have been purchased from Pharmingen, with the exception of IL-12 reagents that were gifted from the Genetics Institute (Boston, USA).

14. Immunofluorescence Staining and Flow Cytometry

For FACS staining, cells were first harvested. For adherent cells where surface receptors need to be intact, a warm 2%

EDTA in PBS solution was used for 20 min at 37° C. After cells were in solution, they were washed once and then resuspended in ice-cold FACS washing buffer. All subsequent incubations were performed at 4° C. For each analysis, $5 \times 10^5$ cells were incubated with the relevant antigen-specific antibody or isotype control for 30 min and then washed twice with FACS washing buffer. Cells were then examined by flow cytometry. cells were ready for analysis on a FACScan flow cytometer (Becton and Dickinson) by using the CellQuest (Becton Dickinson). Directly conjugated monoclonal antibodies to HLA-DR, HLA-A,B,C, CD80, CD86, CD3, CD14 and CD25 were purchased by Pharmingen, San Diego, USA).

15. Preparation of Cytosolic Protein Extracts

Cytosolic extracts were prepared to investigate biochemical events involved in signal transduction by western blotting. Adherent cells were scraped from the tissue culture plate/flask into fresh PBS and harvested by centrifugation (13000 g for 10 seconds at 4° C.). Non-adherent cells were similarly pelleted by centrifugation and washed once with fresh PBS. After discarding the supernatants, an appropriate quantity of ice-cold hypotonic lysis buffer (Whiteside S. T. et al (1992). Nucleic Acids Res 20:1531-8) was added, depending on the number of cells to be lysed (50-100 µl per $1 \times 10^6$ cells). After incubation on ice for 10 minutes, lysates were centrifuged (13000 g, 5 minutes, 4° C.) in order to remove nuclei and cell debris. The cleared lysates were then removed to fresh tubes, frozen and stored at −20° C. for subsequent estimation of protein concentration and use in western blotting.

16. Preparation of Nuclear Protein Extracts

Nuclear protein extracts were prepared to study the NF-κB activation and translocation from the cytosol to the nucleus and its DNA-binding ability. After lysis of cells in hypotonic lysis buffer (see section), nuclei were pelleted by centrifugation (13000 g for 5 minutes at 4° C.), washed once in hypotonic lysis buffer to remove contaminating cytosolic proteins, and then resuspended in hypertonic extraction buffer for 1-2 hours at 4° C. under agitation. Hypotonic lysis buffer prevents leaching of proteins out of the nucleus during lysis, whereas hypertonic extraction buffer makes the nuclear membrane porous, allowing nuclear proteins to escape into solution.

After centrifugation (13000 g for 10 minutes at 4° C.) supernatants containing the nuclear protein were removed to fresh tubes and stored at −70° C. This method of nuclear extracts preparation is based on that of Whiteside S. T. et al (1992). Nucleic Acids Res 20:1531-8.

17. Immunoprecipitation

To immunoprecipitate IRAK, cytosolic extracts were incubated with 3 µg of anti-IRAK antibody for 1 h at 4° C. under gentle shaking. Then, 50 µl of 50% slurry protein G sepharose (Amersham) were added and left for another 2 h shaking. Subsequently, IRAK bound to protein G sepharose was collected, washed four times, resuspended in Western Blot loading buffer, boiled for 5 min and then immediately used for Western blotting.

18. Protein Concentration Assay

Before using cytosolic or nuclear extracts in any further experimental procedure (e.g. western blotting, electrophoretic mobility shift assays), it was necessary to determine their protein concentration in order to ensure that equivalent amounts of protein were present in each sample. Protein concentrations were assessed by the Bradford assay. Briefly, 200 µl of appropriately diluted extracts were added in triplicates in a 96-well tissue culture plate along with 20 µl of a series of BSA concentrations (Sigma, UK) ranging from 10-1000 µg/ml to be used as a standard. 200 µl of Bradford reagent were then added to each well, and absorbance was measured at 595 nm in a spectrophotometer (Multiscan Bichromatic, Labsystems). From the linear standard curve formed by the range of BSA concentrations, protein amounts in the cytosolic and nuclear extracts were determined.

19. Western Blotting and Electrophoretic Mobility Shift Assay

Cytosolic proteins were separated by SDS-PAGE on a 10% (w/v) polyacrylamide gel, followed by electrotransfer onto nitrocellulose membranes. IκBα and IRAK were detected by using antibodies purchased from Santa Cruz Biotechnology (Santa Cruz, USA) and Upstate Biotechnology (USA), respectively, whereas the phosphorylated forms of IκBα, p38 and p42/44 MAPK were detected by antibodies from New England Biolabs.

Results

1. PSI Inhibits the Immunostimulatory Function of DC

PSI is an inhibitor of proteosome activity and as such is capable of inhibiting induced IκB degradation and subsequent NF-κB activation. We used PSI to examine the function of NFκB in dendritic cell (DC) activity particularly in relation to antigen presentation and activation of T cells. We have previously shown that PSI is capable of inhibiting NFκB activation at concentrations up to 1 µM. To test the effect of PSI on DC viability mature DC were incubated with concentrations of PSI, ranging from 0.1 µM to 5 µM. Concentrations of >5 µM showed some toxicity (FIG. 1), as judged by propidium iodide (PI) staining method and so functional studies were only performed over the 0.1 to 2 µM range, using 1 µM in most experiments. To assess the role of NFκB in DC function, mature DC were incubated with 0.3 µM, 0.5 µM or 1 µM PSI for 3 hours and the cells washed. As PSI is an activated peptide that binds irreversibly to the proteosomes, the function of the DC can be assessed over the 6 day period of the MLR despite the short period of drug exposure.

Figure 2:
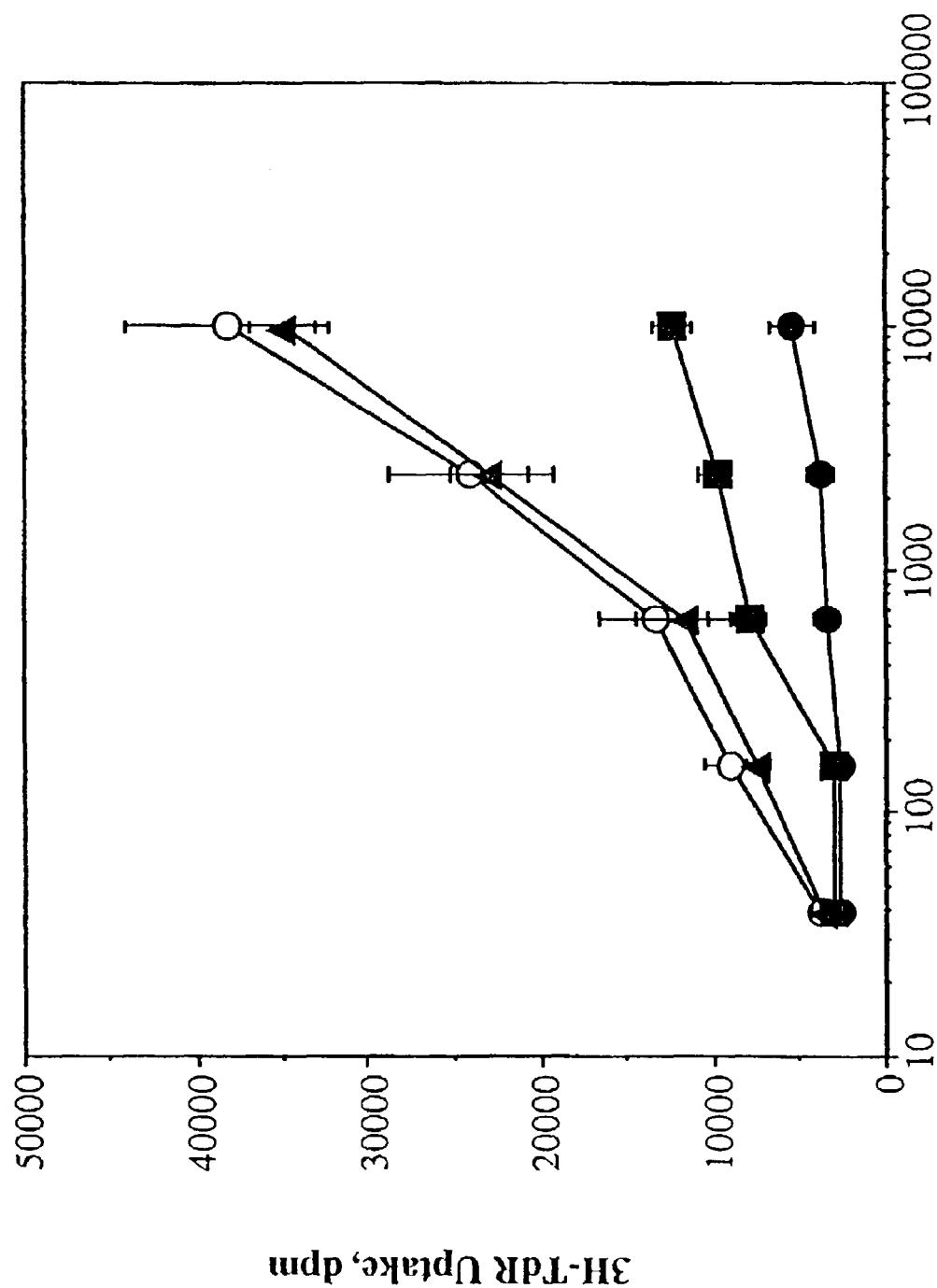
FIG. 2. Immunostimulatory capacity of DC treated with the proteosome inhibitor Cbz-Ile-Glu(O-tert-bytyl)-Ala-leucinal (PSI). Mature DC was treated with PSI (0.1 μM: ▲), (0.5 μM: ■), (1, μM: ●) or without PSI (○) for 4 h. After wash, different numbers of each category of DC and $10_5$ cells of allo-lymphocytes were plated on a 96 well plate. Proliferation was determined at day 6 using $^3$H-TdR uptake assay. (Each point represents mean+/−SEM from five separate experiments).

Exposure of T cells to PSI treated DC (PSI-DC) in an allogeneic MLR assay had profound effect on the response of the lymphocytes that was titratable with PSI concentration. It was found that while pretreatment of DCs with PSI at 0.1 µM had no detectable effect, 0.5 µM and 1 µM resulted in a failure of the T cells to proliferate in response to activation (FIG. 2).

Figure 3:
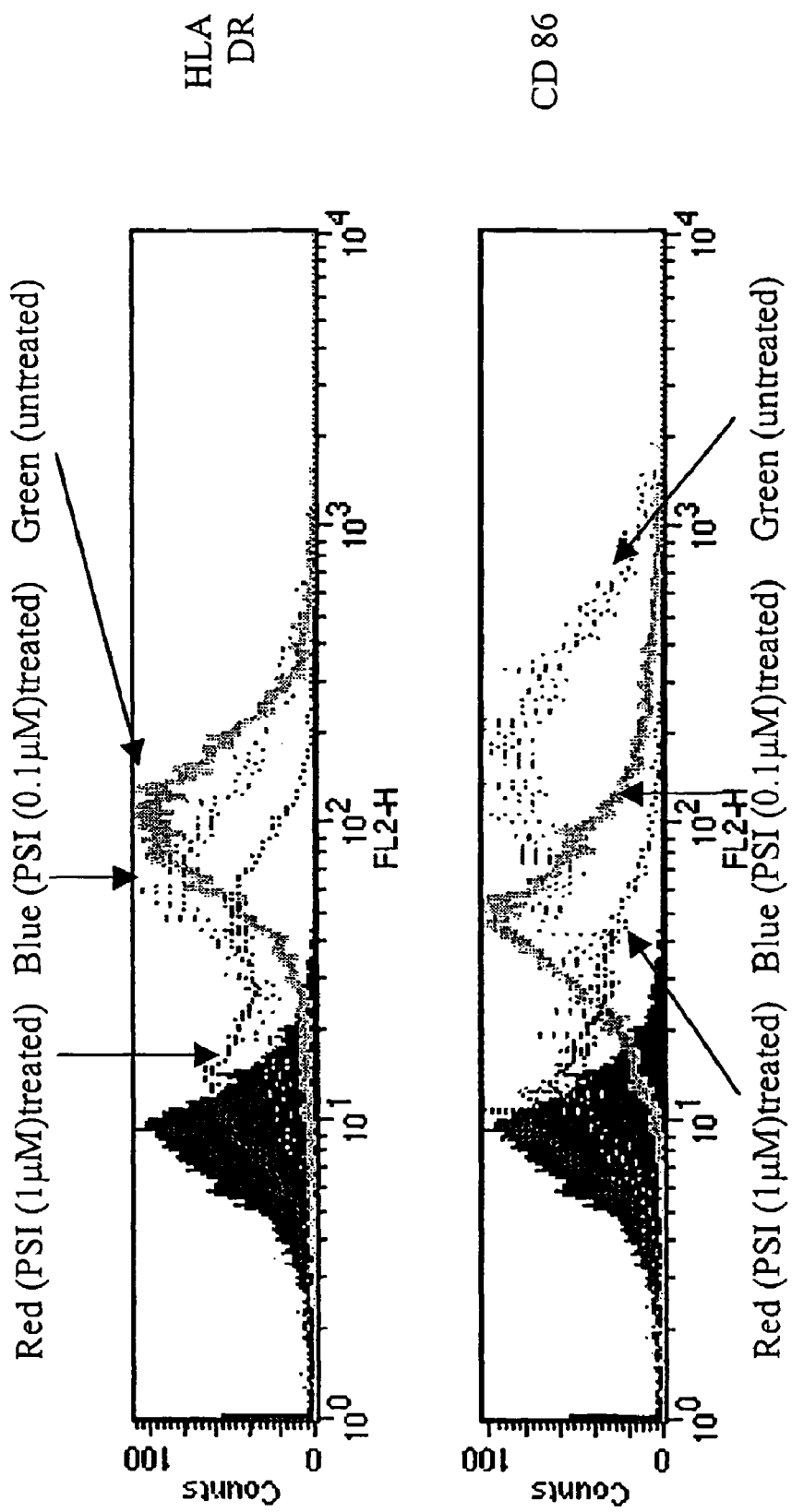
FIG. 3. Effect of PSI on the expression of surface antigens was studied using monoclonal antibodies, HLA-DR, CD86 (PE conjugated); Pharmingen, San Diego, Calif.). on day 6 after PSI treatment, populations of untreated (green line), PSI (0.1 μM) treated (blue dotted line), PSI (1 μM) treated (red dotted line) were phenotyped with the MoAbs listed above and analysed on FACScan (Becton Dickinson).

2. PSI Reduces the Surface Expression of Molecules Involved in Antigen Presentation T cells in the MLR recognise HLA class II antigens, of which HLA-DR is the most abundant and so its expression was assessed, 6 days after PSI treatment. A minimal effect (by FACS) on DR was noted at 0.1µ PSI, but a major reduction was found at 1 µM (FIG. 3). CD86 is the major costimulatory molecule expressed on DC, and its expression was also reduced, to virtually background levels at 1 µM PSI (FIG. 3).

3. Inhibited MLR with PSI Treated Dendritic Cells is not Rescued by IL-2 or Anti CD28 Antibody There are two broad possibilities as to the mechanism of the low proliferative response of T cells to PSI-DC. One is that these DC are not stimulatory, and the T cells are not responding for that reason. The second is that the T. cells have been actively 'switched off' by processes of tolerance or active immune regulation. To begin to discriminate between these possibilities, we attempted to stimulate the T cells with IL-2, or anti CD28 at concentrations (2-ng/ml. IL-2 or 10 µg/ml. anti CD28).

The IL-2 or anti CD28 was added at the same time when T cells and DC were plated. Proliferation was assessed at day 6, and revealed that IL-2 had a very slight effect at restoring proliferation, however this was independent of the number of DC and regardless of PSI treatment (FIG. 4a).

Figure 4:
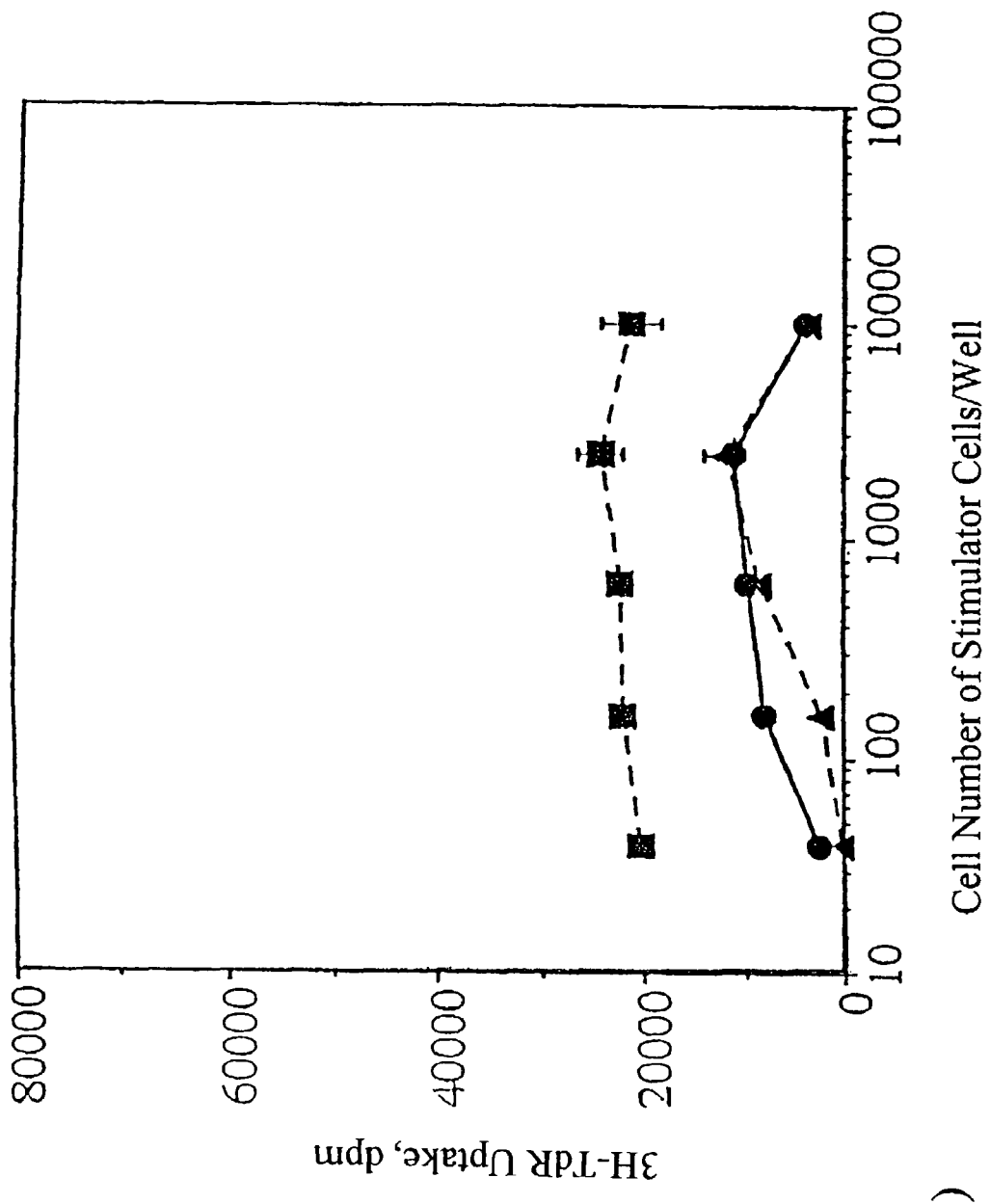
FIG. 4. Lack of recovery of proliferation response in allo-MLR. Mature DC was treated with vehicle (A) or PSI (1 μM) (B) for 4 h. After wash graded number of each treated DC and $10^5$ cells of allo-lymphocytes were plated on a 96 well plate with vehicle (○,●), 2 ng/ml. of IL-2 (□,■) or 10 g/ml. of anti CD28 Ab (Δ, ▲). Proliferation was determined at day 6 using $^3$H-TdR uptake assay. (Each point represents mean+/−SEM from three separate experiments).

The same degree of immunostimulation was seen with untreated DC (FIG. 4b). Anti CD28 had no restorative effect, which had been expected in view of the downregulation of the major CD28 ligand CD86 by PSI (FIG. 3). These results are consistent with multiple mechanisms and so led to further experiments.

4. Inhibition of the DC Induced MLR by DC Pretreated with PSI

Figure 5:
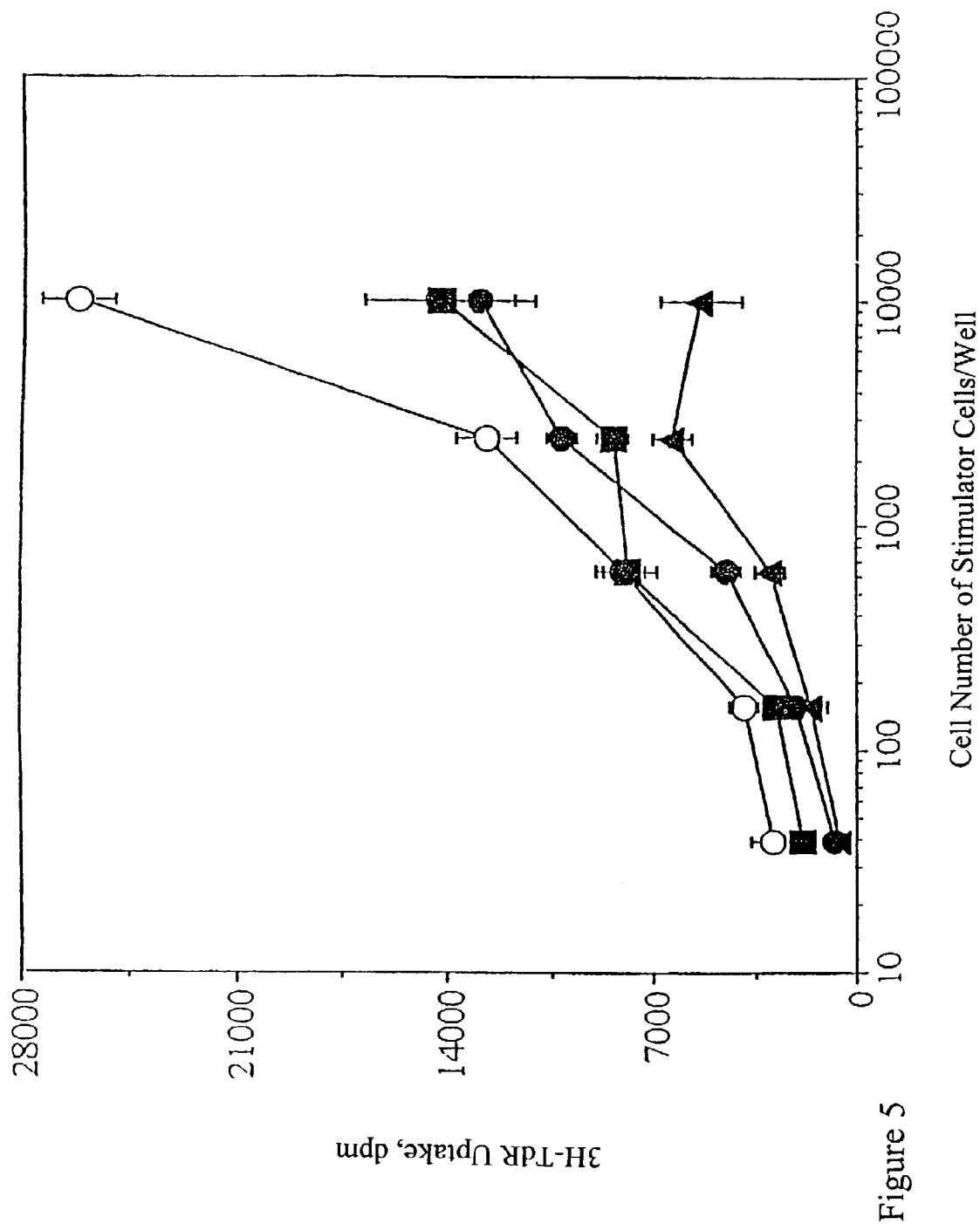
FIG. 5. PSI pre-treated DC inhibit the growing ability of lymphocytes in allo-MLR. Mature DC was treated with PSI as described above. After washing, each DC was mixed to make different compositions: vehicle treated DC only (○), ¼ number of PSI treated DC mixed with ¾ vehicle treated DC (●), ⅛ number of PSI treated DC mixed with % vehicle treated DC (■), or PSI treated DC only (▲). Graded number of each mixture and $10^5$ cells of allo-lymphocytes were plated on a 96 well plate. Proliferation was determined at day 6 by $^3$H-TdR uptake assay.
Figure 6:
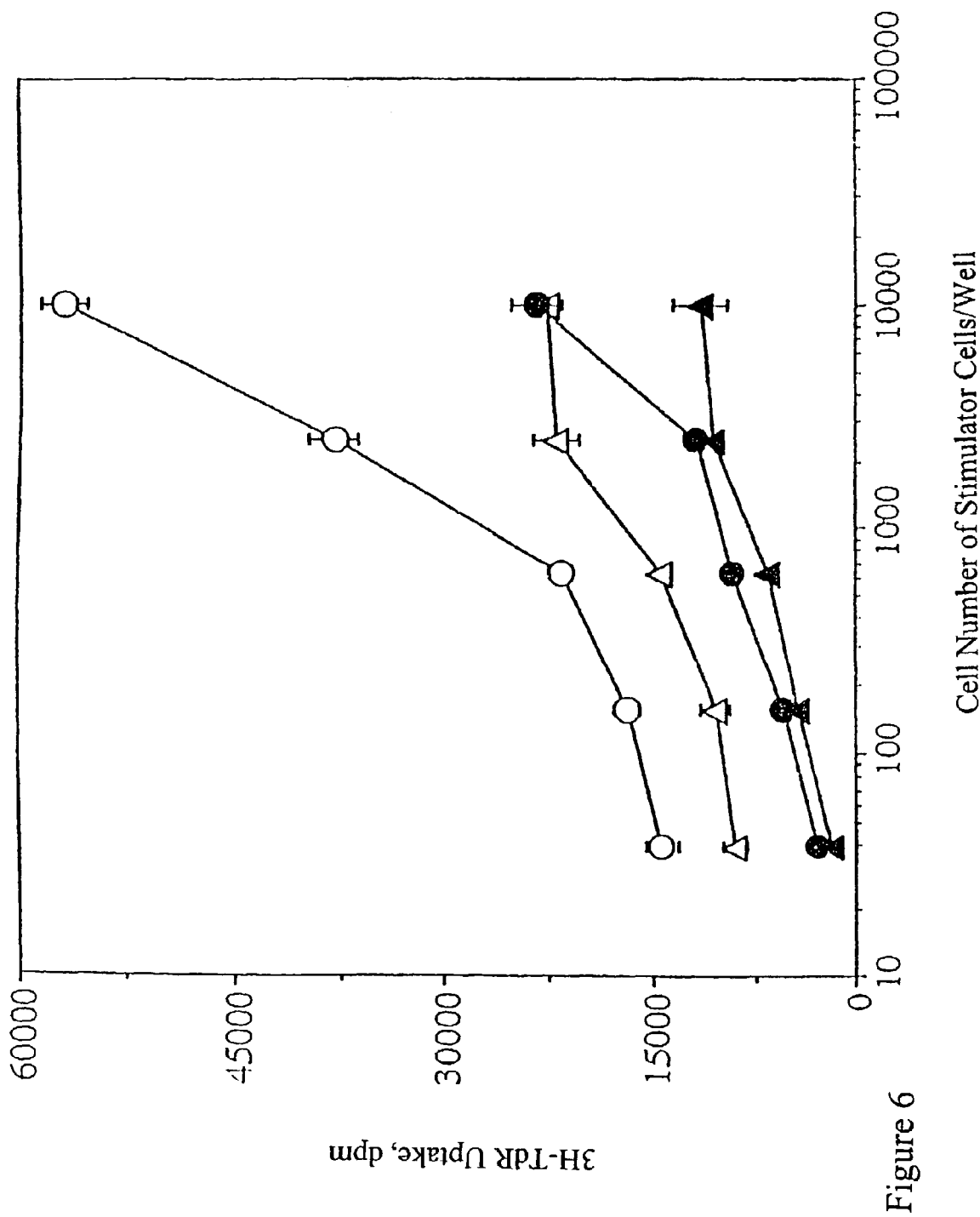
FIG. 6. Impaired response of allo-lymphocytes pre-cultured with PSI treated or non-treated DC. Lymphocytes were co-cultured with ⅟₁₀ number of PSI treated (●, ▲) or non-treated DC (○,Δ). After 2 days, each DC were removed by CD83, CD86 coated plate. Lymphocytes were cultured for another 4 days using vehicle treated DC (○,●), or PSI (1 μM) treated DC (Δ,▲). Proliferation was determined by $^3$H-TdR uptake assay. (Each point represents mean+/−SEM from three separate experiments).

A means of detecting whether PSI-DC were generating inhibitory effects is to culture T cells with a mixture of PSI treated and untreated DC. If the PSI-DC were just non-stimulatory, PSI treated DC should have minimal effects on the proliferative response. However, it was found that the presence of as little as ⅛ or ¼ PSI-DC, resulted in a 3-5 fold reduction response, as judged from the slope of the proliferative response curves (FIG. 5). Next we investigated whether exposure to PSI-DC would induce long term unresponsiveness in the T cells. T cells were exposed to normal or PSI-DC as previously described after which the T cells were collected and were treated with a DC for a second time and the proliferative response measured (FIG. 6). The T cells exposed to normal DC on both occasions responded and as expected T cells did not respond to two rounds of PSI-DC. However, T cells that had been stimulated with PSI-DC prior to normal DC also were unable to respond (FIG. 6). This would indicate that the effects of exposure to PSI-DC are prolonged and the T cells acquire a non-responsive or anergic state. As expected T cells exposed to PSI-DC on the second round after normal DC also failed to proliferate.

5. Cell Surface Antigen Analysis of T Lymphocytes Exposed to PSI Treated Dendritic Cells To probe into the mechanism of the effect of PSI treated DC, we analysed T lymphocyte after 6 days cultures. As anticipated the yields of T cells were lower. Cell surface expression of CD3 was reduced. Most dramatic, however, was the marked diminution of CD25 expression, which was virtually abolished compared to controls (FIG. 7).

Expression of molecules involved in cell surface adhesion, such as CD11a (LFA-1) and one of its receptors ICAM-1 CD54 was analysed. Both were reduced on PSI treated lymphocytes with CD54 reduced to a degree similar to CD3 whereas CD11a expression was only marginally reduced (FIG. 7).

6. Exposure to T Cells to PSI-DC Results in the Production of IL-4 but not IL-2 or IFNγ

The production of cytokines is one of the key responses by T cells to stimulation by DC with IL-2, IFNγ and IL-4 being expressed (FIG. 8). We therefore investigated what type of response occurs with exposure to PSI-DC. IL-2 and the key Th1 cytokine, IFNγ were not produced in response to PSI-DC. However, the production of IL-4 was unaffected. This data would suggest that PSI-DC are capable of delivery some signals to T cells. This would support our prior observation that PSI-DC induce a type of unresponsiveness state in the T cells which is thought to require an active signal.

7. DC Production of TNF but not IL-8 is Inhibited by PSI

We also investigated the effect of PSI on cytokine produced by the DC following on MLR. TNF and, to a lesser extent, IL-6 expression was inhibited from PSI-DC during the MLR. In contrast IL-8 production was unaffected (FIG. 9). Like results on the T cell this shows the discriminatory nature of PSI treatment, and indicates that NFκB has a role in TNF and IL-6 expression but not that of IL-8.

8. Activating DC with MEKK1 Results in Enhanced MLR Response

Figure 10:
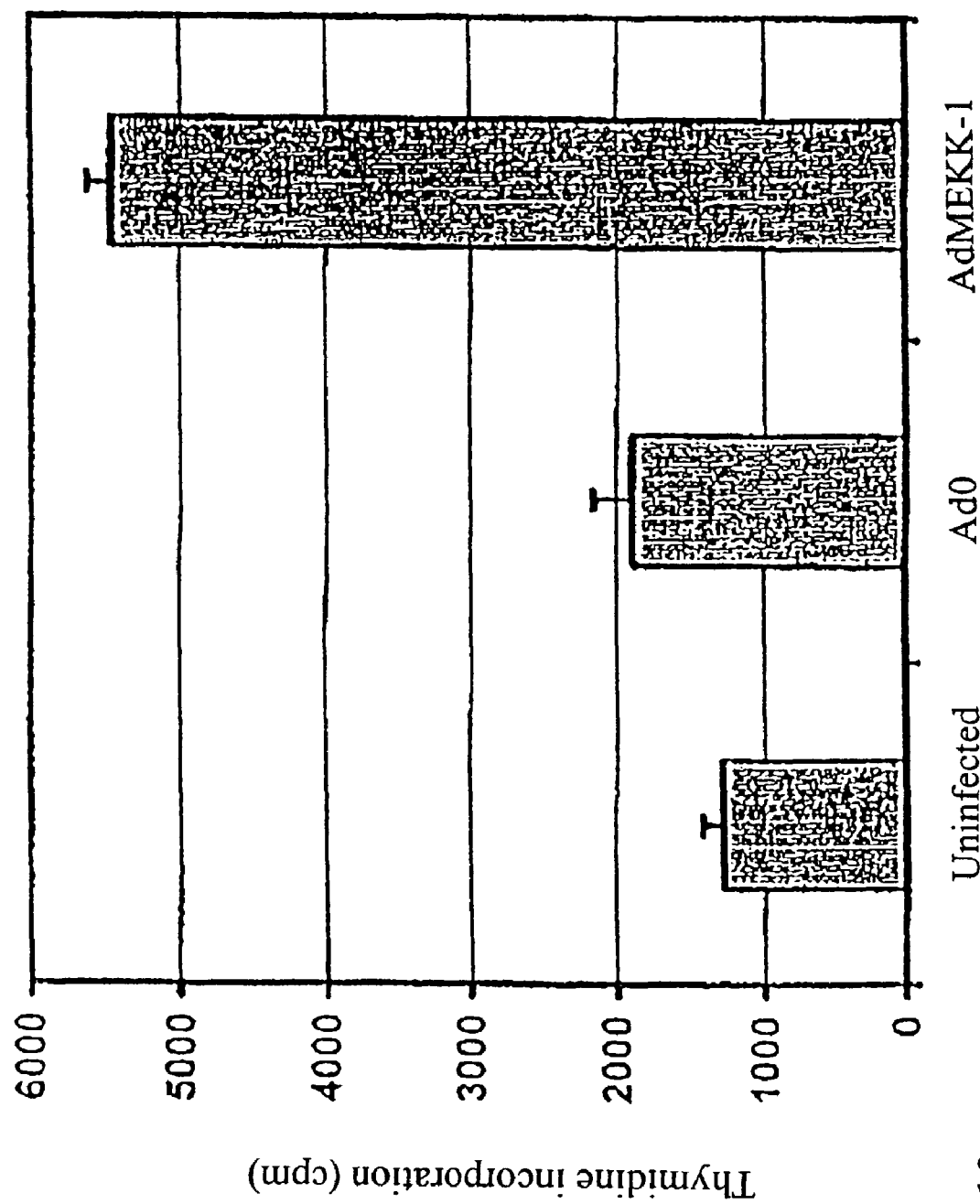
FIG. 10. Expression of MEKK-1 greatly enhances monocyte-derived dendritic cells antigen-presentation in the allogeneic MLR. Briefly, dendritic cells were generated by culturing peripheral blood monocytes with 50 ng/ml. GM-CSF and 10 mg/ml. IL-4. At day 5, they were infected for 2 hours with an adenovirus without insert or encoding MEKK-1 (m.o.i. 100:1), or were left uninfected. After 2 days, $10^4$ dendritic cells were cultured with $10^5$ purified allogeneic T cells for 5 days in 96-well flat-bottomed plates, plused overnight with 0.5 μCi/well and harvested the following day. Dendritic cells encoding MEKK-1 were 4-fold more powerful in inducing T cell proliferation than uninfected DC, whereas this was not true for dendritic cells infected with an adenovirus without insert.

Since inhibition of NFκB inhibits the function of DC, the effect of potentially activating DC using NFκB stimulating MEKK was investigated. Activating encoding MEKK1 was used to infect DC at m.o.i. of 150:1. When used in an MLR such MEKK1 DC was 4-fold more active than normal DC (FIG. 10).

9. Myd881pr Activates NF-κB

Figure 11:
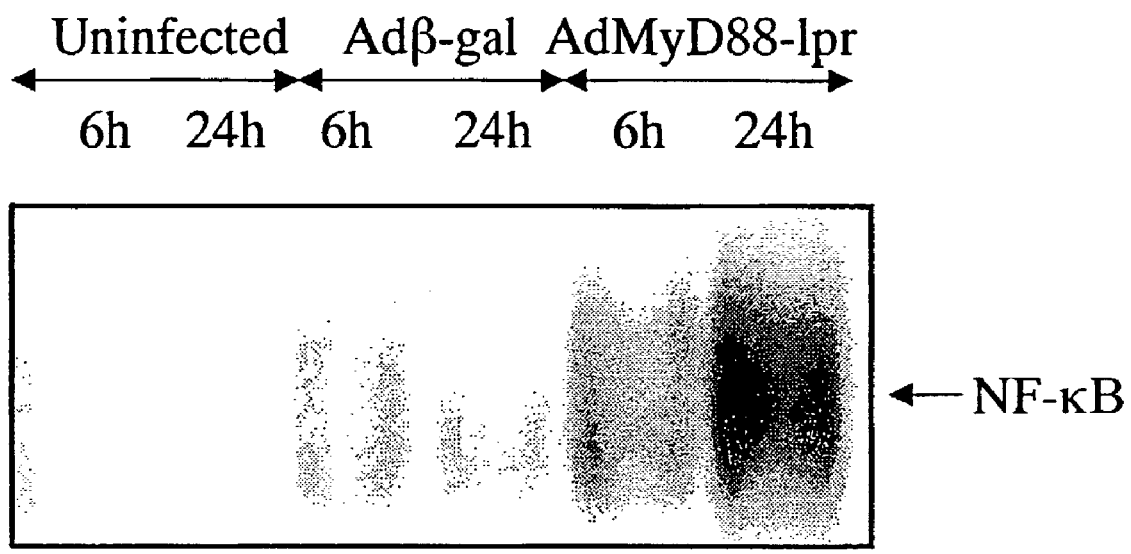
FIG. 11: Expression of dominant negative inhibitor of MyD88 (MyD881pr) in dendritic cells induces NF-κB activation Immature DC were generated from peripheral blood monocytes after 5 days of culture with 50 ng/ml GM-CSF and 10 ng/ml IL-4. Then, they were left uninfected, or infected in serum-free medium with a control adenovirus without insert (Ad0) and an adenovirus encoding dominant-negative MyD88 (AdMyD88-1pr). A multiplicity of infection of 100 was used. After 6 h and 24 h expression, cells were lysed and their nuclear extracts examined for NF-κB DNA-binding activity by EMSA. Surprisingly, expression of MyD881pr could induce on its own NF-κB activation which is totally in contrast with what has been previously found.

We have found that a potent inducer of NF-κB is a mutein of Myd88 that contains a deletion of the first 53 amino acids and a point mutation Phe56Asn termed Myd881pr. Myd881pr is normally inhibiting to Toll related receptor signalling, for example, IL-1 receptors (1). However, we have observed that introduction of Myd881pr, by adenoviral vectors, into immature DC induces a potent activation of nuclear NF-κB activity that is detectable six hours after infection with Admyd88 and more strongly, at 24 hours post-infection (FIG. 11).

10. Myd881pr induces TNF production by immature DC

Figure 12:
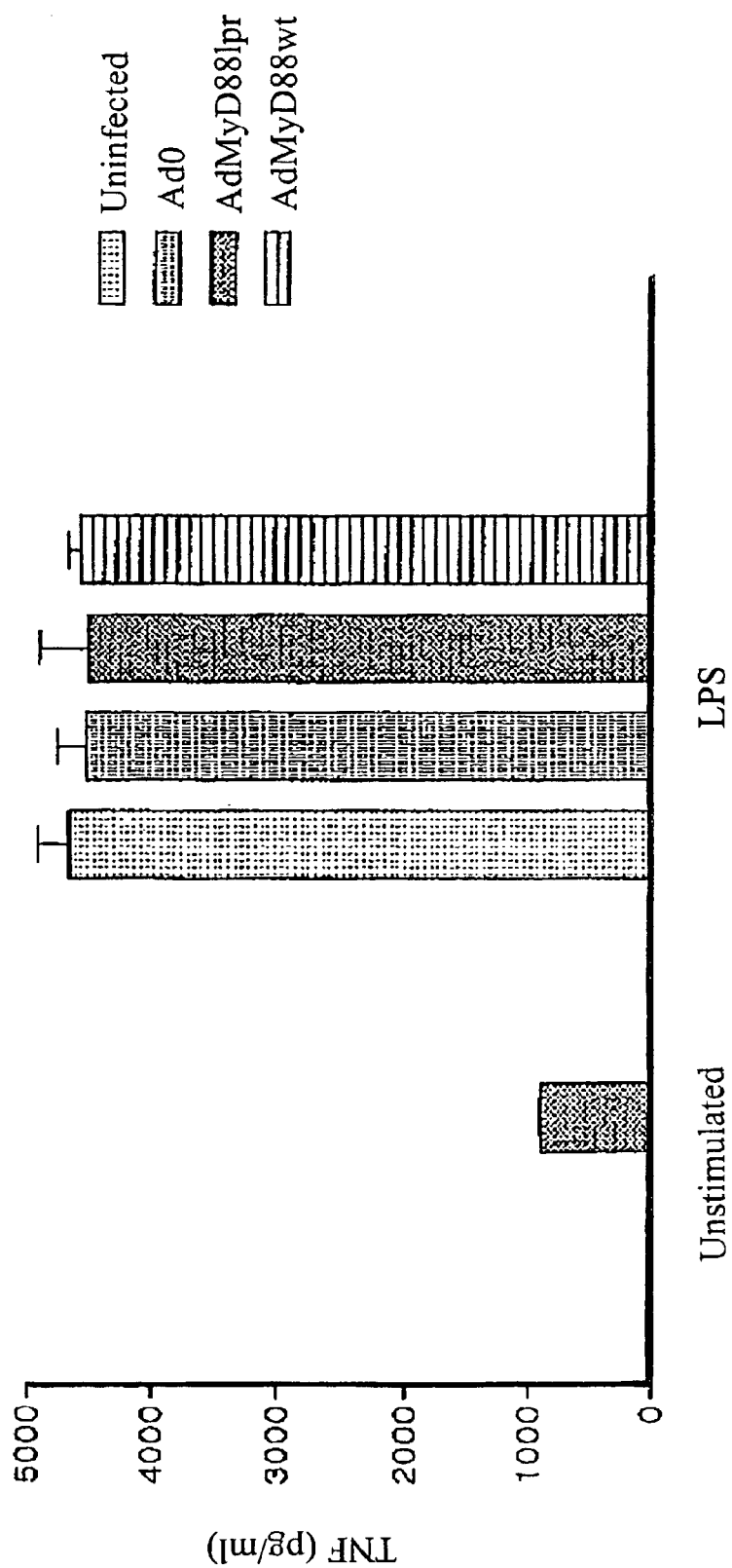
FIG. 12: Expression of dominant negative (inhibitor) but not wild-type MyD88 induces TNFα production on its own and does not inhibit LPS-induced TNFα production in dendritic cells Immature DC were generated from peripheral blood monocytes after 5 days of culture with 50 ng/ml GM-CSF and 10 ng/ml IL-4. Then, they were left uninfected, or infected in serum-free medium with with a control adenovirus encoding β-gal (Adβ-gal), an adenovirus encoding dominant-negative MyD88 (Adlpr) and an adenovirus encoding wild-type MyD88 (AdMyD88wt). Adtoll has been shown to be non-functional and should be ignored. A multiplicity of infection of 100 was used. After 24 h, cells were stimulated with 100 ng/ml LPS. Surprisingly, expression of dominant negative MyD88 could induce dendritic cell TNFα production on its own, in the absence of additional stimulation. Moreover, it could not inhibit LPS-induced TNFα production, a finding that is in contrast to previous findings.
Figure 13:
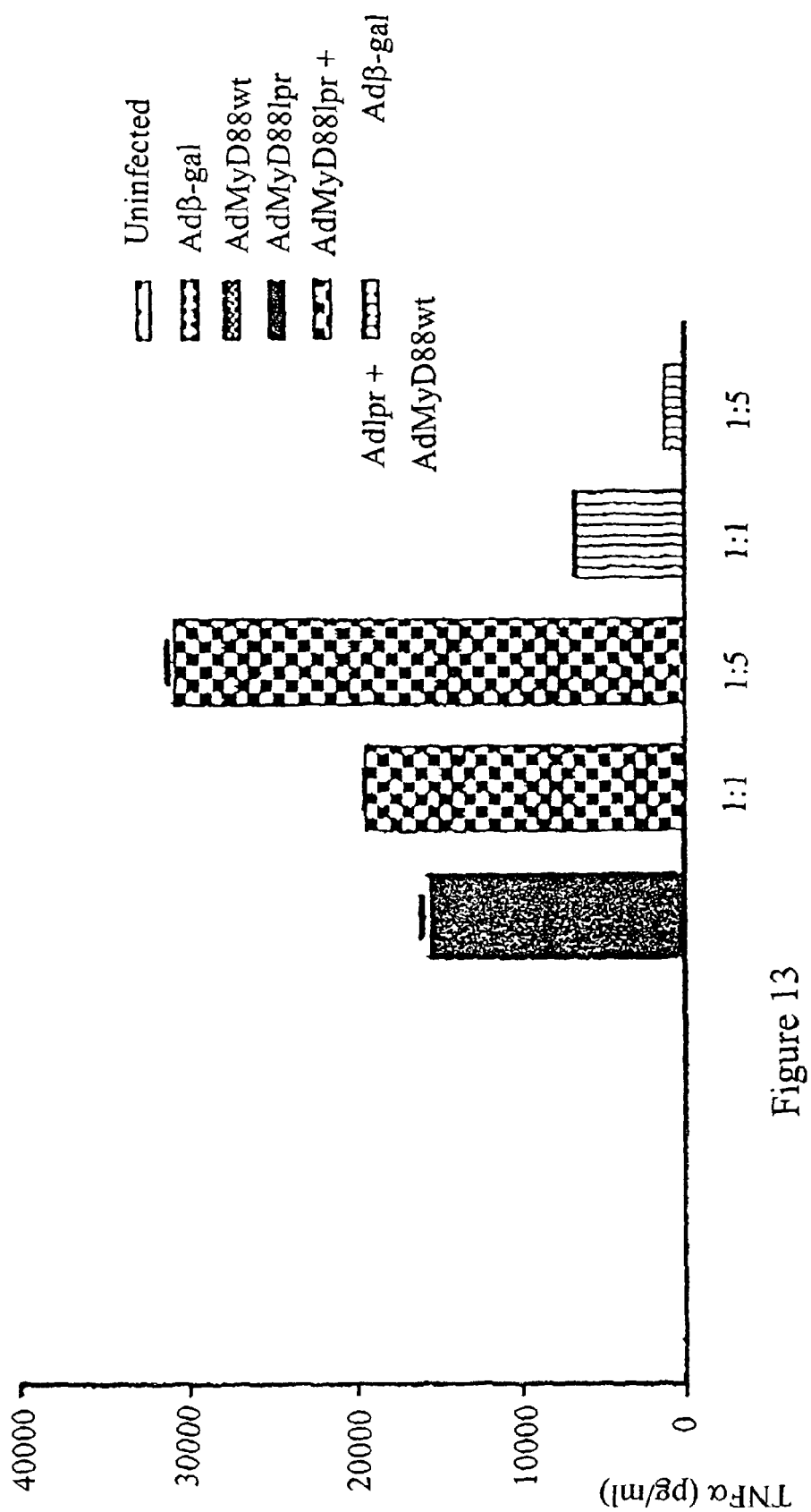
FIG. 13: Expression of wild-type MyD88 abrogates the MyD88-1pr(dominant-negative)-induced TNFα production in dendritic cells Immature DC were generated from peripheral blood monocytes after 5 days of culture with 50 ng/ml GM-CSF and 10 ng/ml IL-4. Then, they were left uninfected, or infected in serum-free medium with a control adenovirus encoding β-gal (Adβ-gal), an adenovirus encoding wild-type MyD88 (AdMyD88wt) and an adenovirus encoding dominant-negative MyD88 (AdMyD881pr). In some cases, double infection by Adlpr and Adβ-gal or AdMyD88wt at ratios 1:1 and 1:5 was used. A multiplicity of infection of 100 was used for single infections. After 24 h, supernatants were removed and analysed. Surprisingly, expression of dominant negative MyD88 could induce dendritic cell TNFα production on its own, in the absence of additional stimulation. Wild-type Myd88 was able to inhibit TNF production induced by Myd881pr.

As with MEKK1, we were interested to see if Myd881pr would also activate DC function. Infection of immature DC with AdMyd881pr, resulted in the spontaneous production of TNF by the cells 24 hours post infection. Moreover, Myd881pr had no inhibiting effect on LPS-induced TNF production. Myd88wt did not induce TNF production in DC (FIG. 12)

11. Myd881pr enhances antigen presentation by DC

Figure 14:
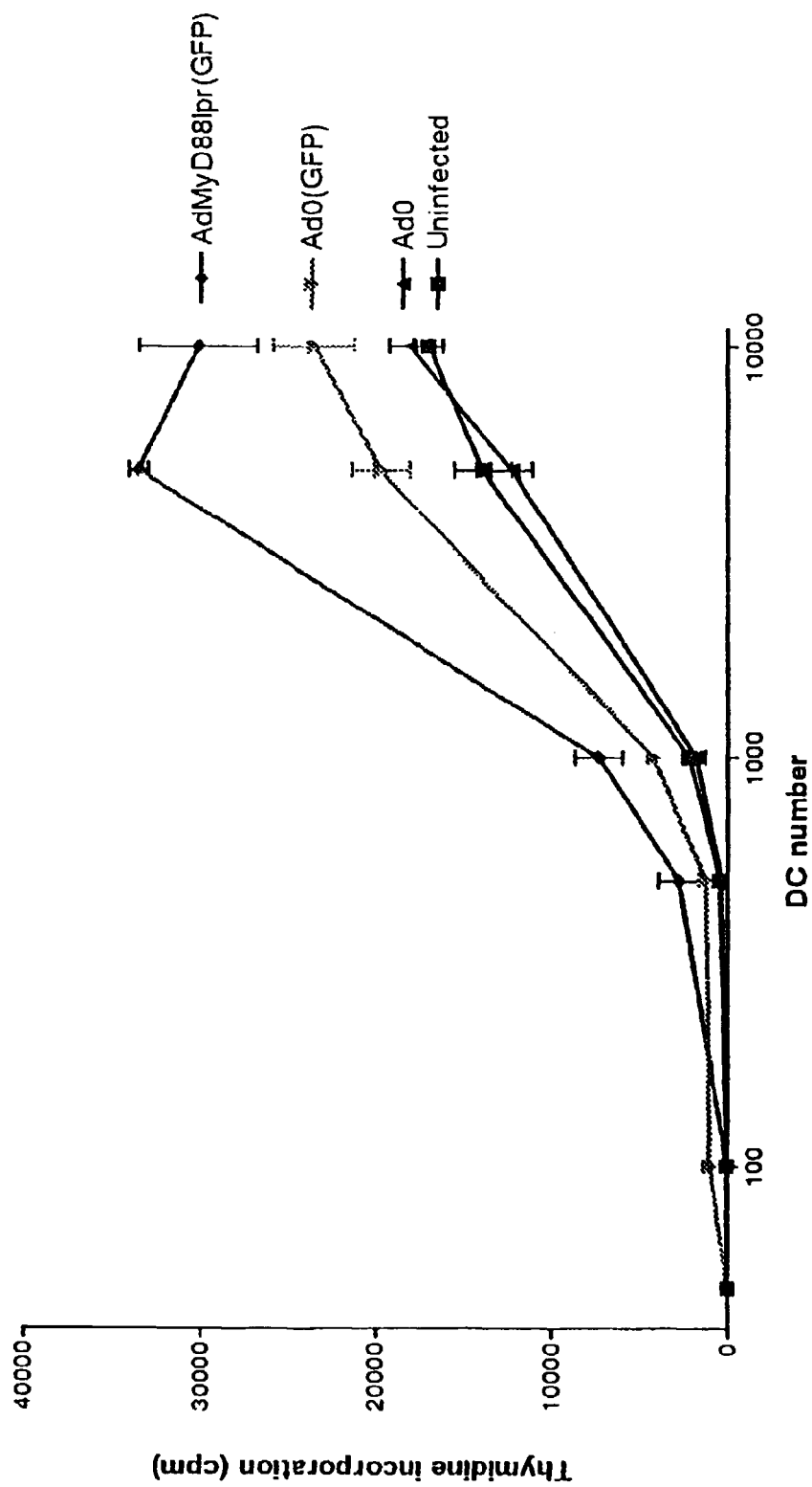
FIG. 14: Expression of dominant-negative MyD88 in dendritic cells enhances antigen-specific T cell proliferation Immature DC were generated from peripheral blood monocytes after 5 days of culture with 50 ng/ml GM-CSF and 10 ng/ml IL-4. Then, they were left uninfected, or infected in serum-free medium with a control adenovirus without insert (Ad0), an adenovirus encoding green fluorescent protein as a prototype antigen (AdGFP), and an adenovirus encoding GFP linked together with the dominant negative MyD88 (AdGFP-1pr). After 48 h, graded doses of dendritic cells were cultured with 2×$10^4$ antigen-specific T cells and proliferation was measured at day 3. Delivery of the antigen GFP to dendritic cells induced antigen-specific T cell proliferation that was enhanced by expression of dominant negative MyD88. This is in agreement with our unexpected result that inhibition of MyD88 activity in dendritic cells, induces dendritic cell activation.

Since inhibition of NF-κB inhibits the function of DC, the effect of potently activating DC using the NF-κB stimulating Myd881pr was investigated. Immature DC were infected with AdMyd881pr (that also expresses GFP), Ad0 or AdGFP (Green Fluorescent Protein). After 24 hours, various concentrations of infected DC were cultured with $2\times10^4$ GFP antigen-specific T cells and response measured as proliferation of the T cells at three days. Delivery of GFP to dendritic cells induced an antigen specific T cell proliferation that was enhanced by Myd881pr (FIG. 14). This result is in agreement with activation of NF-κB and TNF production by Myd881pr shown in the previous figures (FIGS. 11 and 12).

12. Myd881pr Also Enhances DC Induced Allogenic Mixed Lymphocyte Reaction (MLR)

Figure 15:
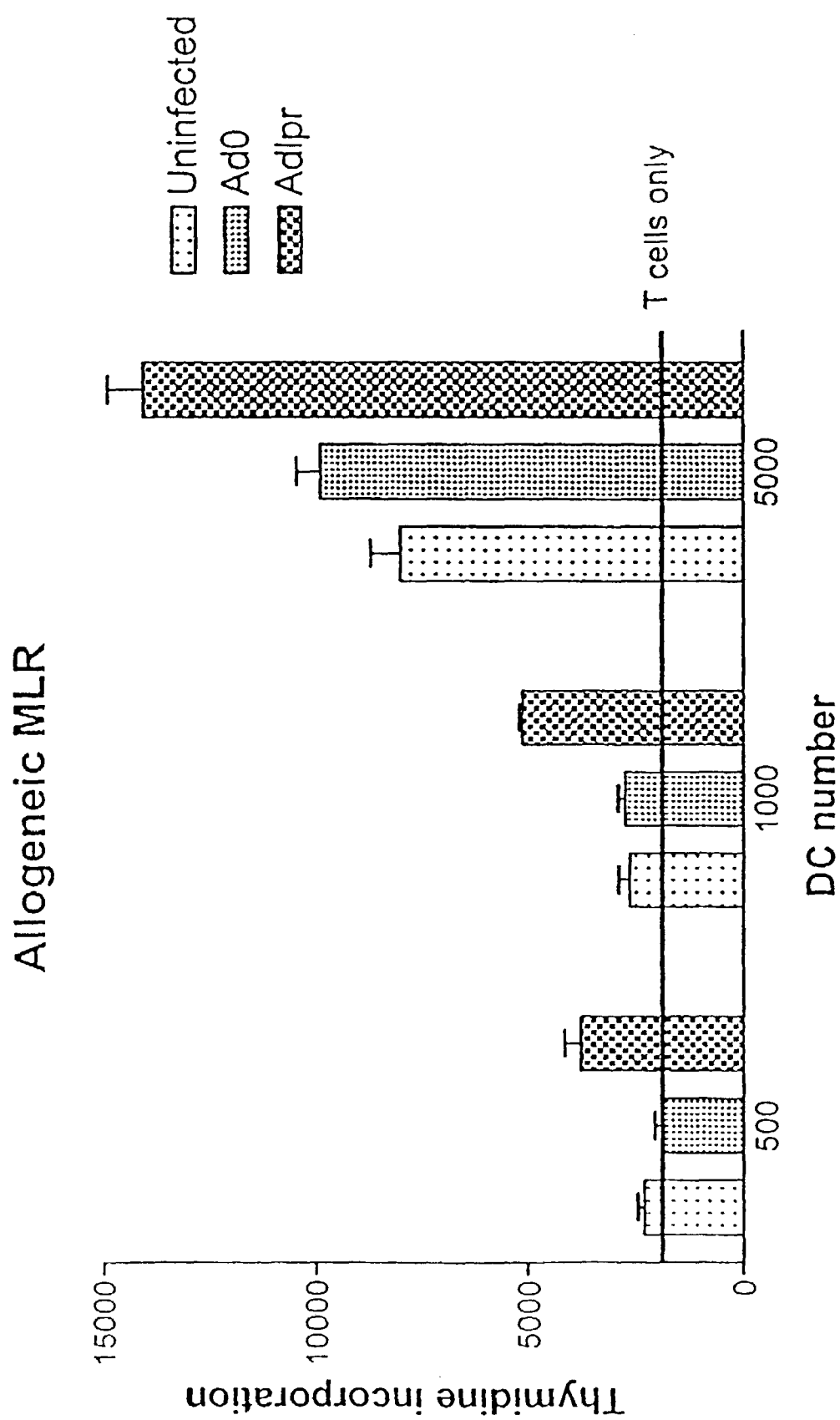
FIG. 15: Expression of dominant-negative MyD88 in dendritic cells enhances the allogeneic mixed lymphocyte reaction (MLR)

Another test of the effect of activity NF-κB function on DC was to investigate the MLR response. Immature DC were infected with Ad0 and Admyd881pr and, after 48 hours, graded doses of the infected DC were cultured with $10^5$ allogenic T cells and responses measured as proliferation after six days of culture. Infection with AdMyd881pr enhanced the MLR response over that of Ad0 or uninfected cells. This was most notable at lower DC numbers where the response of the controls was only equal to T cells only, where the Myd881pr expressing DC response was higher (FIG. 15).

13. Myd881pr Expression Enhances the Expression of Costimulating Molecules CD80 and CD86

The expression of the cell surface molecules CD80 and CD86 are important to the antigen presenting function of DC. In FIG. 16, we show that expression of Myd881pr in DC (by adenoviral infection) enhanced the expression of both CD80 and CD86, when compared with uninfected DC's, or cells infected with control virus.

14. Myd881pr Also Activates Other Signalling Molecules in Addition to NF-κB

We have shown that Myd881pr is a potent inducer of NF-κB. We also observed that this molecule could activate other signalling pathways, this time in macrophages, such as p38 MAPK, a kinase known to be involved in cell mechanisms such as the control of cytokine expression (FIG. 17). Moreover, in macrophages, Myd881pr also activated IRAK1, a key element of TLR and IL-1R signalling mechanisms (FIG. 18).

REFERENCES

1. Burns, K., F. Martinon, C. Esslinger, H. Pahl, P. Schneider, J. L. Bodmer, F. Di Marco, L. French, and J. Tschopp. 1998. MyD88, an adapter protein involved in interleukin-1 signaling. *J Biol Chem* 273, no. 20:12203.

DISCUSSION

Treatment of DC with PSI, a proteasome inhibitor, at concentrations capable of blocking the induction of NFκB, was shown to reduce the proliferative response in the MLR. This suggests that NFκB function is involved in the stimulation of unprimed T cells in the MLR. As the specificity of PSI is for the proteasome, it hence could potentially affect the function of other transcription factors, although this was not reported in the original publications describing the action of this drug (Traenckner et al (1994) EMBO J. 13, 5433-5441; Traenckner & Baeuerle (1995) J. Cell Sci. Suppl. 19, 79-84; and Haas et al (1998) J. Leukoc. Biol. 63, 395-404) Other, independent experiments to verify the role of NFκB using other approaches will be needed, and we have initiated studies using infection of DC with an adenovirus overexpressing IκBα under the control of the CMV promoter. This IκBα overexpression inhibits NFκB, and also inhibits the antigen presenting function of dendritic cells (Yoshimura et al., unpublished data), compatible with the data presented here.

The mechanism of PSI treated DC reduced immunogenicity was evaluated at different levels, and it turned out that multiple aspects of antigen presenting cell function in DC were downregulated. First, the effects on the expression of cell surface molecules by which DC stimulate T cells has been studied, and a marked reduction in the expression of HLA-DR and CD86, both molecules important for both antigen recognition and CD28 activation, was found. Reductions in DC derived cytokines such as IL-12 and TNFα, both known to be important in the early activation of T cells, were also found. In contrast the production of other cytokines such as IL-6 or IL-8 was not changed in T cell/DC cocultures. These results indicate that PSI treated DC have reduced expression of all three major classes of molecules involved in antigen presentation—the target of T cell recognition (HLA-DR) the costimulatory molecules (CD86), as well as immunostimulatory cytokines (IL-12 and TNFα).

Further questions as to the mechanism of the lack of the T cell proliferative response were addressed. It could simply be due to lack of immunogenicity of the DC, or alternatively it could be due to the induction of a form of immunological tolerance or of immune regulation. The mechanism was analysed further by coculture experiments, adding PSI treated DC to untreated DC, and analysing the effect of the mixture on unprimed T cells in the MLR. It was found that if as few as ⅛ (12.5%) PSI treated DC are added to untreated DC there is a significant reduction in the proliferation dose response curve, equivalent to 3-5 fold less active DC. This result, as well as the fact that IL-2 and anti CD28 failed to stimulate these T cells (data not shown), indicates that there is an inhibitory (immunomodulatory) effect of PSI treated DC on T cell function. Furthermore, exposure of T cells to PSI pretreated DC induced profound changes in the expression of T cell surface markers, analyzed on day 6 of coculture: there was reduced expression of CD3, virtually abolished CD25, and some reduction in ICAM-1 and LFA-1. Similar effects have been reported in a variety of tolerance models Zanders et al (1983) Nature 303, 625-627; Zanders et al (1985) J. Immunol. 15, 302-305; Park et al (1997) Eur. J. Immunol. 15, 302-305; and Waldmann & Cubbold (1998) Ann. Rev. Immunol. 16, 619-644 and so we asked whether PSI treated DC induced immunological tolerance. This was assessed by first exposing allogeneic T cells to PSI treated DC for 2 days, and then removing them, by panning with anti CD83 and anti CD86. The T cells were then exposed for 4 days to normal DC/or PSI treated DC from the same donor, and their lack of response is evidence that at least 'long lasting' (4-6 day) immunological tolerance has been induced. The formal definition of tolerance includes 'antigen specificity', that could not be formally tested in this kind of experiment, but it has later been verified in an independent series of experiments using T cell lines responsive to a soluble antigen, tetanus toxoid (Calder et al., unpublished data). However, the term 'immunological tolerance' in this context is an appropriate one, since rechallenge was performed with DC from the same donor.

In another set of experiments, the function of the T cells exposed to PSI treated DC was evaluated further. The T cell cytokine production was markedly altered. Thus IL-2 production was inhibited by more than 90%, as was IFNα production, findings that are also compatible with the induction of tolerance. IL-2 and IFNγ are 'Th1' cytokines, as it was of interest that the expression of the 'Th2' cytokine, IL-4 was not changed. This suggests that the immunosuppressive effect/tolerance induction induced by PSI treated DC may be restricted to the Th1 subset. Further studies with purified Th1 and Th2 T cells are needed to address this point.

The studies reported here, and other experiments using an adenovirus overexpressing the endogenous NFκB inhibitor IκBα (Yoshimura et al., unpublished data), indicate that NFκB has an important role in the regulation of antigen presentation. This agrees well with the earlier finding that NFκB is essential for DC maturation Rescizno et al (1998) J. Exp. Med 188, 2175-2180. It is also consistent with the concept that NFκB is the major mechanism by which innate immunity is translated into adaptive immunity. The so called 'danger signal', which activates the immune system Matzinger (1994) Ann. Rev. Immunol 12, 991-1045; Janeway et al (1196) Curr. Biol. 6, 519-522, activated via a wide variety of microbial or other noxious agents thus appears to involve the activation of NFκB. This has already been established for LPS that requires TLR4 to induce NFκB activation Chow et al (1999) J. Biol. Chem. 274, 10689-10692.

In the context of regulation of antigen presentation it is noteworthy that all 3 aspects, expression of target for T cells (MHC), costimulatory molecules (CD86) as well as inducing cytokines (IL-12, TNFα) are all regulated coordinately by NFκB. This leads to an obvious prediction, that drugs that block NFκB (such as PSI) may be useful immunosuppressive agents in vivo, depending clearly on their toxicity profile. PSI is likely to be too toxic for systemic use might nevertheless be useful for perfusing target organs, such as kidneys, to block APC function prior to transplantation. An interesting corollary of this work is that the deliberate activation of NFκB might provide a good strategy for a useful adjuvant effect for vaccines. Experiments to test that hypothesis are under way.

Further studies are underway to further analyse the exact mechanism by which PSI treated DC influence T cell function:

1. Blocking NF-κB in antigen presenting cells is inhibitory to T cell function, using PSI or other proteasome inhibitors, e.g. or other inhibitors of NF-κB, e.g. cDNA inhibitors such as IκB, antisense to NF-κB constitutes drug inhibitors such as
2. Blocking NF-κB in DC induces tolerance in T cells
3. Use of NF-κB inhibitors in ) autoimmunity
   ) transplantation
   ) allergy 4. Corollary—if NF-κB inhibition blocks antigen presentation and promotes tolerance, then NF-κB stimulation will upregulate antigen presentation. This can be achieved in a number of possible ways, activating pathways which stimulate NF-κB, in order to augment vaccination. These include using adenoviruses or other gene transfer of MEKK1, NIK, IKK2, dominant negative mutants of MyD88, TRAF2, TRAF6. These sequences could be incorporated into the same genetic construct as that encoding the antigen to which immunisation is desired. NF-κB stimulation may also be useful in modulating the immune response in an allergic patient to alter the TH1:TH2 response balance towards a TH1 response.

We believe that the results show that PSI produces an anergic state in DCs. That is the drug induces a long term state of non-responsiveness of the DCs to antigens.

The corollary to the above observations is that by activating an intracellular signalling pathway, such as NF-κB, in DC, one would activate the cell and enhance antigen presenting function. We tested this using NF-κB activating intracellular signalling molecules MEKK1 and Myd881pr. MEKK1 has been previously described as an activator of NF-κB amongst other pathways and the introduction of MEKK1 into DC using adenoviral vectors induced activation of DC function as measured by MLR.

We also observed that a mutein of Myd88, Myd881pr, normally an inhibitor of signalling by TLR and IL-1 receptors, also activated NF-κB in DC. When expressed in DC, Myd881pr enhanced DC antigen present function as measured by MLR, or using antigen specific T cells as well as inducing cytokine production. These results open the possibility that when associated with antigens, intracellular signalling molecules, such as NF-κB, can act as powerful adjuvants. This could provide a new approach to vaccine design. The fact that Myd881pr also activates p38 MAPK would imply that other signalling molecules that activate DC could also be used for this purpose.

The invention claimed is:

1. A method for enhancing antigen presentation by dendritic cells to augment T-cell dependent immune response to an antigen comprising administering to said dendritic cells
   (a) an effective amount of a vector comprising a genetic construct encoding (i) a NF-κB inducer and (ii) the antigen, or
   (b) an effective amount of a nucleic acid encoding a NF-κB inducer and a nucleic acid encoding the antigen;
   wherein the NF-κB inducer is a member selected from the group consisting of mitogen-activated protein kinase kinase kinase (MEKK1), NF-κB inducing kinase (NIK), IκB kinase 2 (IKK2), TNF receptor associated factor 2 (TRAF2), TNF receptor associated factor 5 (TRAF5), TNF receptor associated factor 6 (TRAF6), Transforming Growth Factor β activated kinase (TAK), a dominant negative mutant of Myd88, the kinase expressed by the tumor progression locus 2 gene (TP L-2), IL-1 receptor associated kinase (IRAK), Toll receptors and Rel, and
   wherein the intracellular expression of said NF-κB inducer results in enhanced antigen presentation function by said dendritic cells.

2. The method of claim 1, wherein said NF-κB inducer is mitogen-activated protein kinase kinase kinase (MEKK1) or a dominant negative mutant of MyD88.

3. The method of claim 1 wherein the nucleic acid is within a vector, the vector additionally comprising regulatory elements operatively linked to said nucleic acid and necessary for expression of said nucleic acid.

4. The method of claim 3 wherein the vector is an adenovirus or lentivirus.

5. The method of claim 1 wherein dendritic cells are exposed to the NF-κB inducer and antigen in vitro and introduced into a mammal.

6. The method of claim 1 wherein the antigen comprises an epitope present on transformed or cancerous cells or on a pathogenic organism, or on a cell infected by an organism, or a polypeptide expressed in a pathologic condition.

7. The method of claim 5 wherein said mammal is a human.

* * * * *